US010174336B2

(12) United States Patent
Mankin et al.

(10) Patent No.: US 10,174,336 B2
(45) Date of Patent: Jan. 8, 2019

(54) HERBICIDE-TOLERANT PLANTS

(75) Inventors: Scots L. Mankin, Raleigh, NC (US); Dale R. Carlson, Apex, NC (US); Rex Liebl, Cary, NC (US); Jill Stevenson-Paulik, Cary, NC (US); Maciej Pasternak, Heidelberg (DE); Annegret Welzel, Ludwigshafen (DE)

(73) Assignee: BASF Agrochemical Products B.V.

( * ) Notice: Subject to any disclaimer, the term of this patent is extended or adjusted under 35 U.S.C. 154(b) by 1203 days.

(21) Appl. No.: 13/520,391

(22) PCT Filed: Jan. 7, 2011

(86) PCT No.: PCT/US2011/020546
§ 371 (c)(1),
(2), (4) Date: Oct. 15, 2012

(87) PCT Pub. No.: WO2011/085221
PCT Pub. Date: Jul. 14, 2011

(65) Prior Publication Data
US 2013/0042366 A1 Feb. 14, 2013

Related U.S. Application Data

(60) Provisional application No. 61/293,165, filed on Jan. 7, 2010.

(51) Int. Cl.
*C12N 15/82* (2006.01)
*C12N 15/52* (2006.01)
*C12N 9/02* (2006.01)

(52) U.S. Cl.
CPC ....... *C12N 15/8274* (2013.01); *C12N 9/0077* (2013.01); *C12N 15/52* (2013.01)

(58) Field of Classification Search
None
See application file for complete search history.

(56) References Cited

U.S. PATENT DOCUMENTS

| | | | |
|---|---|---|---|
| 5,349,127 A | 9/1994 | Dean et al. | |
| 7,405,057 B2 | 7/2008 | Chappell et al. | |
| 2002/0199221 A1* | 12/2002 | Bilyeu | A01H 5/10 800/312 |
| 2006/0048240 A1* | 3/2006 | Alexandrov | C07K 14/415 800/278 |
| 2008/0148432 A1 | 6/2008 | Abad | |
| 2009/0011936 A1 | 1/2009 | Hawkes et al. | |
| 2009/0217415 A1 | 8/2009 | Dam et al. | |
| 2012/0149576 A1 | 6/2012 | Saijo et al. | |

FOREIGN PATENT DOCUMENTS

| | | |
|---|---|---|
| JP | 2009-529891 | 8/2009 |
| KR | 10-2007-0044681 | 4/2007 |
| WO | WO 2006/136596 A1 | 12/2006 |
| WO | WO 2007/103567 A1 | 9/2007 |
| WO | WO 2007/106904 | 9/2007 |
| WO | WO2008150473 A2 | 12/2008 |
| WO | WO 2009/046334 | 4/2009 |
| WO | WO-2010143743 A1 | 12/2010 |

OTHER PUBLICATIONS

GenBank Accession No. AAK63920, Putative Cytochrome P450, submitted Jun. 19, 2001.*
GenBank Accession No. XM_010231249.1, disclosing Brachypodium distachyon isoflavone 3'-hydroxylase-like mRNA and protein, submitted Nov. 14, 2014.*
Powles et al, Annu. Rev. Plant Biol. (2010) 61:317-347.*
Morant et al, Curr. Opinion Biotech (2003) 14:151-162.*
The Free Dictionary, definition of the term "crop", available at http://www.thefreedictionary.com/crop, accessed on Jun. 8, 2016.*
Catalan et al, Annals of Botany (2012) 109:385-405.*
GenBank Accession No. CM000880, submitted on Feb. 18, 2010.*
UniProt Accession No. I1GN24, integrated into UniProt on Jun. 13, 2012.*
Campbell et al, Plant Physiol. (1990) 92:1-11.*
Vogel et al, Nature (2011) 463:763-767.*
Giraldo-Canas, D., Polibotanica (2010) 30:163-191.*
Busi et al, Heredity (2011) 106:817-824.*
Grossmann et al, Weed Science (2011) 59:290-298.*
Firhauf, J., PhD Dissertation, Kansas State University (2009).*
Miller et al, Can. J. Plant Sci. (2012) 92:1319-1328.*
Garvin, D.F., J. Sci. Food Agric. (2007) 87:1177-1179.*
Abecassis et al., "Exploration of Natural and Artificial Sequence Spaces: Towards a Functional Remodeling of Membrane-Bound Cytochrome P450," Biocatel. Biotrans., 21: 55-66 (2003).
Bell et al., "Engineering Substrate Recognition in Catalysis by Cytochrome P450cam," BioChem. Soc. Trans. 31: 558-562 (2003).
Buell, R., Genbank Accession No. AAK63920.1; according to NCBI online revision history, first seen at NCBI on Jun. 19, 2001, pp. 1-2.
Chow, T-Y, Genbank Accession No. AAV44089.1; according to NCBI online revision history, first seen at NCBI on Nov. 2, 2004, pp. 1-2.
Clay, P.A., et al., "Evaluation of Various PPO Inhibitors as Defoliants for Upland Cotton," Arizona Cotton Report (9-145) 237-243 (2006).
Davies, J., "Herbicide Safeners—Commercial Products and Tools for Agrochemical Research," The Royal Society of Chemistry, 10-15 (2001).
Davydov, D.R., et al., "Allosteric P450 Mechanisms: Multiple Binding Sites, Multiple Conformers, or Both?" Expert. Opin. Drug Metab. Toxicol. 4(12): 1523-1535 (2008).
Didierjean et al., "Engineering Herbicide Metabolism in Tobacco and *Arabidopsis* with CYP76B1, a Cytochrome P450 Enzyme from Jerusalem Artichoke," Plant Physiol., 130: 179-189 (2002).

(Continued)

*Primary Examiner* — Mykola V. Kovalenko
(74) *Attorney, Agent, or Firm* — Mintz Levin Cohn Ferris Glovsky and Popeo, P.C.

(57) ABSTRACT

The present invention provides saflufenacil-tolerant plants. The present invention also provides methods for controlling the growth of weeds by applying saflufenacil to which the saflufenacil-tolerant plants of the invention are tolerant. Plants of the invention express a cytochrome P450 polypeptide, the expression of which confers, to the plants, tolerance to the saflufenacil.

2 Claims, 8 Drawing Sheets

Specification includes a Sequence Listing.

(56) References Cited

OTHER PUBLICATIONS

Grossmann, K., et al., "The Herbicide Saflufenacil (KixorTM) is a New Inhibitor of Protoporphyrinogen IX Oxidase Activity," Weed Science, 58: 1-9 (2010).
Hamdane, D., et al., "Oxygen Activation by Cytochrome P450 Monooxygenase," Photosynth. Res., 98(1-3): 657-666 (2008).
Hiei, Y., and Komari, T., "Agrobacterium-Mediated Transformation of Rice Using Immature Embryos or Calli Induced from mature Seed," Nat. Protoc. 3: 824-834 (2008).
Hong, H.P., et al., Organogenic Callus as the Target for Plant Regeneration and Transformation via Agrobacterium in Soybean (Glycine Max(L) Merr.), In Vitro Cell. Dev. Biol. Plant., 43: 558-568 (2007).
Inui, H., et al., "Herbicide Resistance in Transgenic Plants with Mammalian P450 Monooxygenase Genes," Pest management Science, 61: 286-291 (2005).
Mankin, S.L., et al., "Disarming and Sequencing of Agrobacterium Rhizogenes Strain K599 (NCPPB2659) Plasmid pRi2659," In Vitro. Cell. Dev. Biol. Plant, 43: 521-535 (2007).
Nedelkina, S., et al., "Novel Characteristics and Regulation of Divergent Cinnamate 4-Hydroxylase (CYP73A15) from French Bean: Engineering Expression in Yeast," Plant Molec. Biol., 39: 1079-1090 (1999).
Nelson, "Plant Cytochrome P450s from Moss to Poplar," Phytochem. Rev., 5: 193-204 (2006).
Nguyen, L. and R.J. Henry, "Expression of P450 Gene in Barley (*Hordeum Vulgare*)," Barley Genetics Newsletter, 36:17-27 (2006).
Nordby, J.N., et al., "A Common Genetic Basis in Sweet Corn Inbred Cr1 for Cross Sensitivity to Multiple Cyctochrome P450-Metabolized Herbicides," Weed Science, 56: 376-382 (2008).
Pan et al., "Map-based Cloning of a Novel Rice Cytochrome P450 Gene CYP81A6 That Confers resistance to Two Different Classes of Herbicides," Plant Molec. Biol., 61: 933-943 (2006).
Ryu et al., "Evaluation of the Genetic Toxicity of Synthetic Chemicals (XI)—A Synthetic Sulfonylurea Herbicides, Pyrazosulfuron-Ethyl-," Environ. Mutagens and Carcinogens, 24(1): 38-39 (2004).
Sasaki, T., Genbank Accession No. BAB19083.1; according to NCBI online revision history, first seen at NCBI on Dec. 13, 1999, pp. 1-2.
Siminszky et al., "Co-Expression of a NADPH:P450 Reductase Enhances CYP71A10-Dependent Phenylurea Metabolism in Tobacco," Pestic. Biochem. Physiol., 77: 35-43 (2003).
Siminszky, "Plant Cytochrome P450-Mediated Herbicide Metabolism," Phytochem. Rev. 5:445-458 (2006).
Tan, S., et al., "Imidazolinone-Tolerant Crops: History, Current Status and Future," Pest Management Science, 61: 246-257 (2005).
Wenjian, L., et al., "High-Performance Liquid Chromatographic Separation of Imidazolinone Herbicide Enantiomers and their Methyl Derivatives on Polysaccharide-Coated Chiral Stationary Phases," J. of Chromatog. A., 1117: 184-193 (2006).
Williams et al., "Map-Based Cloning of the NSF1 Gene of Maize," Program and Abstracts of the 48th Maize Genetic Conference (2006) p. 26.
"Brachypodium: a new moncot model plant system emerges," J. Sci. Food Agriculture, 87; pp. 1177-1179 (2007).
Putative Cytochrome [*Oryza sativa*]. [online]. Jun. 19, 2001 uploaded. NCBI Entrez Protein, Accession No. AAK63920 (GI:4488353) Retrieved from the Internet, URL:http://www.ncbi.nlm.nih.gov/protein/14488353?sat=8&satkey=2549154.
Os05g0320700 [*Oryza sativa* (japonica cultivar-group)]. [online]. Oct. 2, 2006 uploaded. NCBI Entrez Protein, Accession No. NP_001055190 (GI:115463181) Retrieved from the internet: URL:http://www.ncbi.nlm.nih.gov/protein/115463181?sat=11&satkey=5889070.
Os01g0627500 [*Oryza sativa* (japonica cultivar-group)].[online]. Oct. 2, 2006 uploaded. NCBI Entrez Protein, Accession No. NP_00104362 (GI:115438705) Retrieved from the internet: URL:http://www.ncbi.nlm.nih.gov/protein/115438705?sat=11&satkey=5870025.
Os03g0760200 [*Oryza sativa* Japonica Group].[online]. Oct. 2, 2006 uploaded. NCBI Entrez Protein, Accession No. NP_001051342 (GI:115455483) Retrieved from the internet: URL:http://www.ncbi.nlm.nih.gov/protein/115455483?sat=11&satkey=5885219.

* cited by examiner

```
   1 MGSTHLPIVG FNASTTPSLS TLRQINSAAA AFQSSSPSRS SKKKSRRVKS IRDDGDGSVP
  61 DPAGHGQSIR QGLAGIIDLP KEGASAPDVD ISHGSEDHKA SYQMNGILNE SHNGRHASLS
 121 KVYEFCTELG GKTPIHSVLV ANNGMAAAKF MRSVRTWAND TFGSEKAIQL IAMATPEDMR
 181 INAEHIRIAD QFVEVPGGTN NNNYANVQLI VETAERTGVS AVWPGWGHAS ENPELPDALT
 241 AKGIVFLGPP ASSMNALGDK VGSALIAQAA GVPTLAWSGS HVEIPLELCL DSIPEEMYRK
 301 ACVTTADEAV ASCQMIGYPA MIKASWGGGG KGIRKVNNDD EVKALFKQVQ GEVPGSPIFI
 361 MRLASQSRHL EVQLLCDEYG NVAALHSRDC SVQRRHQKII EEGPVTVAPR ETVKELEQAA
 421 RRLAKAVGYV GAATVEYLYS METGEYYFLE LNPRLQVEHP VTESIAEVNL PAAQVAVGMG
 481 IPLWQIPEIR RFYGMDNGGG YDIWRKTAAL ATPFNFDEVD SQWPKGHCVA VRITSENPDD
 541 GFKPTGGKVK EISFKSKPNV WGYFSVKSGG GIHEFADSQF GHVPAYGETR SAAITSMSLA
 601 LKEIQIRGEI HTNVDYTVDL LNAPDFRENT IHTGWLDTRI AMRVQAERPP WYISVVGGAL
 661 YKTITTNAET VSEYVSYLIK GQIPPKHISL VHSTISLNIE ESKYTIEIVR SGQGSYRLRL
 721 NGSLIEANVQ TLCDGGLLMQ LDGNSHVIYA EEEAGGTRLL IDGKTCLLQN DHDPSRLLAE
 781 TPCKLLRFLI ADGAHVDADV PYAEVEVMKM CMPLLSPAAG VINVLLSEGQ AMQAGDLIAR
 841 LDLDDPSAVK RAEPFEGSFP EMSLPIAASG QVHKRCAASL NAARMVLAGY DHAANKVVQD
 901 LVWCLDTPAL PFLQWEELMS VLATRLPRRL KSELEGKYNE YKLNVDHVKI KDFPTEMLRE
 961 TIEENLACVS EKEMVTIERL VDPLMSLLKS YEGGRESHAH FIVKSLFEEY LSVEELFSDG
1021 IQSDVIERLR LQYSKDLQKV VDIVLSHQGV RNKTKLILAL MEKLVYPNPA AYRDQLIRFS
1081 SLNHKRYYKL ALKASELLEQ TKLSELRTSI ARNLSALDMF TEEKADFSLQ DRKLAINESM
1141 GDLVTAPLPV EDALVSLFDC TDQTLQQRVI QTYISRLYQP QLVKDSIQLK YQDSGVIALW
1201 EFTEGNHEKR LGAMVILKSL ESVSTAIGAA LKDASHYASS AGNTVHIALL DADTQLNTTE
1261 DSGDNDQAQD KMDKLSFVLK QDVVMADLRA ADVKVVSCIV QRDGAIMPME RTFLLSEEKL
1321 CYEERPILRH VEPPLSALLE LDKLKVKGYN EMKYTPSRDR QWHIYTLRNT ENPKMLHRVF
1381 PRTLVRQPSA GNRFTSDHIT DVEVGHAEEP LSFTSSSILK SLKIAKEELE LHAIRTGHSH
1441 MYLCILKEQK LLDLVPVSGN TVVDVGQDEA TACSLLKEMA LKIHELVGAR MHHLSVCQWE
1501 VKLKLVSDGP ASGSWRVVTT NVTGHTCTVD IYREVEDTES QKLVYHSTAL SSGPLHGVAL
1561 NTSYQPLSVI DLKRCSARNN KTTYCYDFPL TFEAAVQKSW SNISSENNQC YVKATELVFA
1621 EKNGSWGTPI IPMQRAAGLN DIGMVAWILD MSTPEFPSGR QIIVIANDIT FRAGSFGPRE
1681 DAFFEAVTNL ACEKKLPLIY LAANSGARIG IADEVKSCFR VGWTDDSSPE RGFRYIYMTD
1741 EDHDRIGSSV IAHKMQLDSG EIRWVIDSVV GKEDGLGVEN IHGSAAIASA YSRAYEETFT
1801 LTFVTGRTVG IGAYLARLGI RCIQRIDQPI ILTGFSALNK LLGREVYSSH MQLGGPKIMA
1861 TNGYVHLTVP DDLEGVSNIL RWLSYVPANI GGPLPITKSL DPIDRPVAYI PENTCDPRAA
1921 ISGIDDSQGK WLGGMFDKDS FVETFEGWAK TVVTGRAKLG GIPVGVIAVE TQTMMQLVPA
1981 DPGQPDSHER SVPRAGQVWF PDSATKTAQA MLDFNREGLP LPILANWRGF SGGQRDLFEG
2041 ILQAGSTIVE NLRTYNQPAF VYIPKAAELR GGAWVVIDSK INPDRIECYA ERTAKGNYLE
2101 PQGLIEIKFR SEELKECMGR LDPELIDLKA RLQGANGSLS DGRSLQKSTE ARKKQLLPLY
2161 TQIAVRFAEL HDTSLRMAAK GVIRKVVDWE DSRSFFYKRL RRRLSEDVLA KEIRGVIGEK
2221 FPHKSAIELI KKWYLASEAA AAGSTDWDDD DAFVAWRENP ENYKEYIKEL RAQRVSRLLS
2281 DVAGSSSDLQ ALPQGLSMLL DKMDPSKRAQ FIEEVMKVLK
47993292v.1
```

HERBICIDE-TOLERANT PLANTS

CROSS-REFERENCE TO RELATED APPLICATIONS

This application is a national phase of International Application PCT/US2011/020546, filed Jan. 7, 2011, which claims the benefit of priority under 35 USC § 119 to U.S. Provisional Application No. 61/293,165 filed on Jan. 7, 2010, each of which is herein incorporated by reference in its entirety.

FIELD OF THE INVENTION

The present invention relates to herbicide-tolerant plants.

BACKGROUND OF THE INVENTION

P450's form a large diverse gene family with about 246 isoforms in *Arabidopsis* and 372 identified in rice. P450s are hemoproteins that convert a broad range of substrates to more or less bioactive products. P450s are critical in numerous metabolic pathways, including lignin and pigment biosynthesis, detoxification of harmful compounds, and are considered important in the evolution of land plants. Inhibitors of P450 activity include 1-aminobenzo-triazole, tetcyclacis, piperonyl butoxide, and tridiphane.

Saflufenacil is an herbicide active ingredient (A.I.) of the pyrimidinedione chemical class. Saflufenacil is an active ingredient that is similar to flumioxazin and sulfentrazone and is readily absorbed by foliage, root, and shoot tissue of plants. It is believed that saflufenacil inhibits the pigment biosynthesis pathway at protoporphyrinogen oxidase (PPO), which causes an accumulation of photodynamic, toxic compounds that rapidly damage cell membranes and results in cell death. Herbicidal compositions can be used that have saflufenacil as the sole A.I. or that are supplemented with glyphosate to manage a wide spectrum of dicot weeds. Herbicidal compositions comprising saflufenacil have been labeled for pre-plant or pre-emergence treatment in corn, *sorghum*, wheat, barley, oats, rye, triticale, soybean, and tree/nut/vine cropping systems. Saflufenacil-containing herbicidal compositions have good foliar and residual activity on broadleaf weeds in both no-till and tilled cropping systems. However, application of saflufenacil after emergence can result in rapid and significant crop injury.

There remains a need in the art for plants or plants parts that exhibit tolerance to herbicidal compositions comprising saflufenacil.

BRIEF SUMMARY OF THE INVENTION

In one aspect, the present invention provides a plant or plant part comprising a recombinant polynucleotide encoding a CYP81A or CYP73A polypeptide, the expression of which confers to the plant or plant part tolerance to saflufenacil. In some embodiments, the recombinant polynucleotide encodes a CYP72A15 polypeptide, the expression of which confers to the plant or plant part tolerance to saflufenacil.

In some aspects, the present invention provides a seed capable of germination into a plant comprising in at least some of its cells a recombinant polynucleotide operably linked to a promoter operable in plant cells, the promoter capable of expressing a CYP81A or CYP73A polypeptide encoded by the polynucleotide, the expression of the polypeptide conferring to the plant tolerance to saflufenacil. In some embodiments, the recombinant polynucleotide encodes a CYP72A15 polypeptide, the expression of which confers to the plant tolerance to saflufenacil.

In one aspect, the present invention provides a plant cell of or capable of regenerating a plant comprising in at least some of its cells a recombinant polynucleotide operably linked to a promoter operable in plant cells, the promoter capable of expressing a CYP81A or CYP73A polypeptide encoded by the polynucleotide, the expression of the polypeptide conferring to the plant tolerance to saflufenacil, wherein the plant cell comprises the recombinant polynucleotide operably linked to a promoter. In some embodiments, the recombinant polynucleotide encodes a CYP72A15 polypeptide, the expression of which confers to the plant tolerance to saflufenacil.

In another aspect, the present invention provides a plant cell comprising a recombinant polynucleotide operably linked to a promoter operable in the cell, the promoter capable of expressing a CYP81A or CYP73A polypeptide encoded by the polynucleotide, the expression of the polypeptide conferring to the cell tolerance to saflufenacil. In some embodiments, the recombinant polynucleotide encodes a CYP72A15 polypeptide, the expression of which confers to the cell tolerance to saflufenacil.

In other aspects, the present invention provides a plant product prepared from a plant or plant part comprising in at least some of its cells a recombinant polynucleotide operably linked to a promoter operable in plant cells, the promoter capable of expressing a CYP81A, or CYP73A polypeptide encoded by the polynucleotide, the expression of the polypeptide conferring to the plant or plant part tolerance to saflufenacil. In some embodiments, the recombinant polynucleotide encodes a CYP72A15 polypeptide, the expression of which confers to the plant or plant part tolerance to saflufenacil.

In some aspects, the present invention provides a progeny or descendant plant derived from a plant comprising in at least some of its cells a recombinant polynucleotide operably linked to a promoter operable in plant cells, the promoter capable of expressing a CYP81A or CYP73A polypeptide encoded by the polynucleotide, the expression of the polypeptide conferring to the plant tolerance to saflufenacil, wherein the progeny or descendant plant comprises in at least some of its cells the recombinant polynucleotide operably linked to the promoter, the expression of the polypeptide in the progeny or descendant plant conferring to the progeny or descendant plant tolerance to the saflufenacil. In some embodiments, the recombinant polynucleotide encodes a CYP72A15 polypeptide, the expression of which confers to the plant tolerance to saflufenacil.

In other aspects, the present invention provides a method for controlling weeds at a locus for growth of a plant, the method comprising: (a) applying an herbicide composition comprising saflufenacil to the locus; and (b) planting a seed at the locus, wherein the seed is capable of producing a plant that comprises in at least some of its cells a recombinant polynucleotide operably linked to a promoter operable in plant cells, the promoter capable of expressing a CYP81A or CYP73A polypeptide encoded by the polynucleotide, the expression of the polypeptide conferring to the plant tolerance to the saflufenacil. In some embodiments, the recombinant polynucleotide encodes a CYP72A15 polypeptide, the expression of which confers to the plant tolerance to saflufenacil.

In some aspects, the present invention provides a method for controlling weeds at a locus for growth of a plant, the method comprising: applying an herbicidal composition comprising saflufenacil to the locus; wherein said locus is: (a) a locus that contains: a plant or a seed capable of producing said plant; or (b) a locus that is to be after said applying is made to contain the plant or the seed; wherein the plant or the seed comprises in at least some of its cells a recombinant polynucleotide operably linked to a promoter operable in plant cells, the promoter capable of expressing a cytochrome P450 polypeptide encoded by the polynucleotide, the expression of the polypeptide conferring to the plant tolerance to the saflufenacil. In one embodiment, the polypeptide is a CYP72A15 polypeptide or an isoform of CYP81A or CYP73A.

In other aspects, the present invention provides a method of producing a plant having tolerance to saflufenacil, the method comprising regenerating a plant from a plant cell transformed with a recombinant polynucleotide operably linked to a promoter operable in the cell, the promoter capable of expressing a CYP81A or CYP73A polypeptide encoded by the polynucleotide, the expression of the polypeptide, conferring to the plant tolerance to the saflufenacil. In some embodiments, the recombinant polynucleotide encodes a CYP72A15 polypeptide, the expression of which confers to the plant tolerance to saflufenacil.

In one aspect, the present invention provides a method of producing a progeny plant having tolerance to saflufenacil, the method comprising: crossing a first saflufenacil-tolerant plant with a second plant to produce a saflufenacil-tolerant progeny plant, wherein the first plant and the progeny plant comprise in at least some of their cells a recombinant polynucleotide operably linked to a promoter operable in plant cells, the promoter capable of expressing a CYP81A or CYP73A polypeptide encoded by the polynucleotide, the expression of the polypeptide conferring tolerance to saflufenacil. In some embodiments, the recombinant polynucleotide encodes a CYP72A15 polypeptide, the expression of which confers tolerance to saflufenacil.

In still further aspects, the present invention provides a plant or plant part comprising in of at least some of its cells a recombinant polynucleotide operably linked to a promoter operable in plant cells, the promoter capable of expressing a CYP81A or CYP73A polypeptide encoded by the polynucleotide, the expression of the polypeptide conferring to the plant or plant part tolerance to saflufenacil, wherein the plant or plant part further exhibits a second herbicide-tolerant trait. In some embodiments, the recombinant polynucleotide encodes a CYP72A15 polypeptide, the expression of which confers to the plant or plant part tolerance to saflufenacil.

BRIEF DESCRIPTION OF THE DRAWINGS

FIG. 1: *Alopecurus myosuroides* ACCase amino acid sequence GenBank accession no. CAC84161. Amino acids that can be altered in the ACCase enzymes of the invention are indicted in bold double underline.

DETAILED DESCRIPTION OF THE INVENTION

Definitions

Figure 2A:
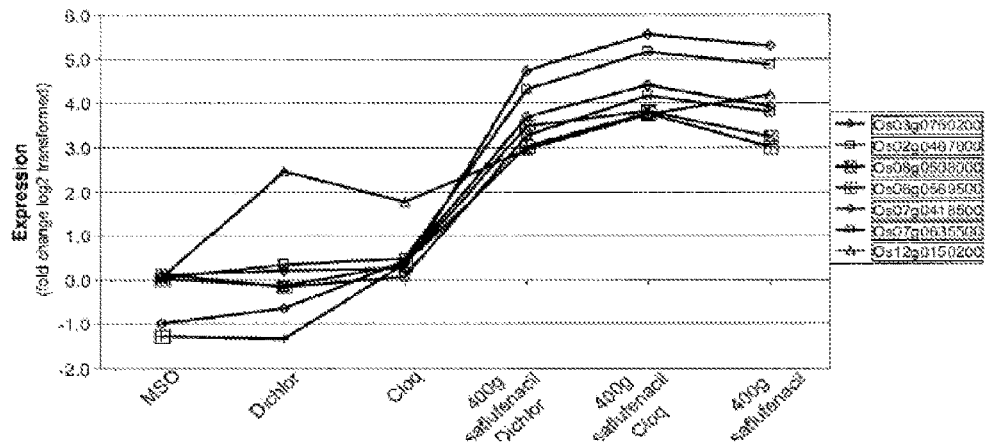
FIGS. 2A and 2B: Graphs presenting safener and saflufenacil-induced expression of rice (FIG. 2A) and maize (FIG. 2B) P450 genes. Expression of rice and maize P450 genes are shown as the fold change (log 2 transformed) over that of unsprayed check controls

As used herein, "tolerant" or "herbicide-tolerant" indicates a plant or plant part thereof capable of growing in the presence of an amount of herbicide that normally causes growth inhibition in a non-tolerant (e.g., a wild-type) plant or portion thereof. Levels of herbicide that normally inhibit growth of a non-tolerant plant are known and readily determined by those skilled in the art. Examples include the amounts recommended by manufacturers for application. The maximum rate is an example of an amount of herbicide that would normally inhibit growth of a non-tolerant plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope.

As used herein, in regard to an herbicidal composition useful in various embodiments hereof, terms such as PPO inhibitor (e.g., saflufenacil), acetohydroxyacid synthase (AHAS) inhibitor, acetyl-Coenzyme A carboxylase (ACCase) inhibitor, 5-enolpyruvyl shikimate 3-phosphate synthase (EPSPS) inhibitor, imidazolinone, sulfonylurea, and the like, refer to those agronomically acceptable herbicide active ingredients (A.I.) recognized in the art. Similarly, terms such as fungicide, nematicide, pesticide, and the like, refer to other agronomically acceptable active ingredients recognized in the art.

When used in reference to a particular mutant enzyme or polypeptide, terms such as herbicide-tolerant and herbicide-tolerance refer to the ability of such enzyme or polypeptide to perform its physiological activity in the presence of an amount of an herbicide A.I. that would normally inactivate or inhibit the activity of the wild-type (non-mutant) version of said enzyme or polypeptide. For example, when used specifically in regard to an AHAS enzyme, or AHASL polypeptide, it refers specifically to the ability to tolerate an AHAS-inhibitor. Classes of AHAS-inhibitors include sulfonylureas, imidazolinones, triazolopyrimidines, sulfonylaminocarbonyltriazolinones, and pyrimidinyloxy[thio]benzoates. In some embodiments in which an imidazolinone herbicide is to be used, the AHASL is preferably one that comprises at least one herbicide tolerance mutation located at amino acid residue position 122, 205, 574, or 653 (*Arabidopsis thaliana* AHASL numbering); and in some embodiments in which a sulfonylurea herbicide is to be used, the AHASL is preferably one that comprises at least one herbicide tolerance mutation located at amino acid residue position 197 or 574 (*Arabidopsis thaliana* AHASL numbering).

As used herein, "recombinant," when referring to nucleic acid or polypeptide, indicates that such material has been altered as a result of human application of a recombinant technique, such as by polynucleotide restriction and ligation, by polynucleotide overlap-extension, or by genomic insertion or transformation. A gene sequence open reading frame is recombinant if that nucleotide sequence has been removed from it natural text and cloned into any type of artificial nucleic acid vector. The term recombinant also can refer to an organism having a recombinant material, e.g., a plant that comprises a recombinant nucleic acid can be considered a recombinant plant.

The term "transgenic plant" refers to a plant that comprises a heterologous polynucleotide. Preferably, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been so altered by the presence of heterologous nucleic acid including those transgenic organisms or cells initially so altered, as well as those created by crosses or asexual propagation from the initial transgenic organism or cell. In some embodiments, a "recombinant" organism is a "transgenic" organism. The term "transgenic" as used herein is not intended to encompass the alteration of the genome (chromosomal or extra-chromosomal) by conventional plant breeding methods (e.g., crosses) or by naturally occurring events such as, e.g., self-fertilization, random cross-fertilization, non-recombinant viral infection, non-recombinant bacterial transformation, non-recombinant transposition, or spontaneous mutation.

As used herein, "mutagenized" refers to an organism or DNA thereof having alteration(s) in the biomolecular sequence of its native genetic material as compared to the sequence of the genetic material of a corresponding wild-type organism or DNA, wherein the alteration(s) in genetic material were induced and/or selected by human action. Examples of human action that can be used to produce a mutagenized organism or DNA include, but are not limited to, as illustrated in regard to herbicide tolerance: tissue culture of plant cells (e.g., calli) and selection thereof with herbicides (e.g., saflufenacil); treatment of plant cells with a chemical mutagen and subsequent selection with herbicide(s); or by treatment of plant cells with x-rays and subsequent selection with herbicide(s). Any method known in the art can be used to induce mutations. Methods of inducing mutations can induce mutations in random positions in the genetic material or can induce mutations in specific locations in the genetic material (i.e., can be directed mutagenesis techniques), such as by use of a genoplasty technique.

As used herein, a "genetically modified organism" (GMO) is an organism whose genetic characteristics contain alteration(s) that were produced by human effort causing transfection that results in transformation of a target organism with genetic material from another or "source" organism, or with synthetic or modified-native genetic material, or an organism that is a descendant thereof that retains the inserted genetic material. The source organism can be of a different type of organism (e.g., a GMO plant can contain bacterial genetic material) or from the same type of organism (e.g., a GMO plant can contain genetic material from another plant). As used herein in regard to plants and other organisms, "recombinant," "transgenic," and "GMO" are considered synonyms and indicate the presence of genetic material from a different source; in contrast, "mutagenized" is used to refer to a plant or other organism, or the DNA thereof, in which no such transgenic material is present, but in which the native genetic material has become mutated so as to differ from a corresponding wild-type organism or DNA.

As used herein, "wild-type" or "corresponding wild-type plant" means the typical form of an organism or its genetic material, as it normally occurs, as distinguished from, e.g., mutagenized and/or recombinant forms.

As used herein, "descendant" refers to any generation plant. In some embodiments, a descendant is a first, second, third, fourth, fifth, sixth, seventh, eight, ninth, or tenth generation plant.

As used herein, "progeny" refers to a first generation plant.

The term "seed" comprises seeds of all types, such as, for example, true seeds, caryopses, achenes, fruits, tubers, seedlings and similar forms. In the context of *Brassica* and *Sinapis* species, "seed" refers to true seed(s) unless otherwise specified. For example, the seed can be seed of transgenic plants or plants obtained by traditional breeding methods. Examples of traditional breeding methods can include cross-breeding, selfing, back-crossing, embryo rescue, in-crossing, out-crossing, inbreeding, selection, asexual propagation, and other traditional techniques as are known in the art.

Although exemplified with reference to specific plants or plant varieties and their hybrids, in various embodiments, the presently described methods using saflufenacil can be employed with a variety of commercially valuable plants. Saflufenacil-tolerant plant lines described as useful herein can be employed in weed control methods either directly or indirectly, i.e. either as crops for herbicide treatment or as saflufenacil-tolerance trait donor lines for development, as by traditional plant breeding, to produce other varietal and/or hybrid crops containing such trait or traits. All such resulting variety or hybrids crops, containing the ancestral saflufenacil-tolerance trait or traits can be referred to herein as progeny or descendant of the ancestral, saflufenacil-tolerant line(s). Such resulting plants can be said to retain the "herbicide tolerance characteristic(s)" of the ancestral plant, i.e. meaning that they possess and express the ancestral genetic molecular components responsible for the trait.

In one aspect, the present invention provides a plant or plant part comprising a recombinant polynucleotide encoding a cytochrome P450 polypeptide, the expression of which confers to the plant or plant part tolerance to saflufenacil.

In some embodiments, the cytochrome P450 polypeptide is a CYP81A isoform or a CY73A isoform polypeptide. In other embodiments, the cytochrome P450 polypeptide is CYP81A6, NSF1, CYP73A38, or CYP72A15. In one embodiment, the CYP81A isoform is CYP81A6 or NSF1.

In other embodiments, the present invention provides a plant or plant part comprising a recombinant polynucleotide encoding a cytochrome P450 polypeptide, the expression of which confers to the plant or plant part tolerance to saflufenacil, with the provisio that the P450 polypeptide is a cytochrome P450 other than NSF1. In another embodiment, the NSF1 is other than a maize NSF1.

A CYP81A6 amino acid sequence is disclosed by, e.g., GenBank Accession No. AAK63920.1, which is herein incorporated by reference in its entirety.

In one embodiment, the plant or plant part of the present invention comprises a recombinant polynucleotide encoding a CYP81A6 polypeptide, the expression of which confers to the plant or plant part tolerance to saflufenacil. In another embodiment, the CYP81A6 polypeptide is a rice polypeptide. In other embodiments, the CYP81A6 polypeptide has the amino acid sequence set forth in SEQ ID NO:1. The recombinant polynucleotide encoding the CYP81A6 polypeptide has the nucleic acid sequence set forth in SEQ ID NO:2.

An NSF1 amino acid sequence is disclosed by, e.g., GenBank Accession No. ACG28028.1, which is herein incorporated by reference in its entirety.

In one embodiment, the plant or plant part of the present invention comprises a recombinant polynucleotide encoding an NSF1 polypeptide, the expression of which confers to the plant or plant part tolerance to saflufenacil. In another embodiment, the NSF1 polypeptide is a corn polypeptide. In other embodiments, the NSF1 polypeptide has the amino acid sequence set forth in SEQ ID NO:3. The recombinant polynucleotide encoding the CYP81A6 polypeptide has the nucleic acid sequence set forth in SEQ ID NO:4.

A CYP73A38 amino acid sequence is disclosed by, e.g., GenBank Accession No. NP_001055190.1, which is herein incorporated by reference in its entirety.

In one embodiment, the plant or plant part of the present invention comprises a recombinant polynucleotide encoding a CYP73A38 polypeptide, the expression of which confers to the plant or plant part tolerance to saflufenacil. In another embodiment, the CYP73A38 polypeptide is a rice polypeptide. In other embodiments, the CYP73A38 polypeptide has the amino acid sequence set forth in SEQ ID NO:5. The recombinant polynucleotide encoding the CYP73A38 polypeptide has the nucleic acid sequence set forth in SEQ ID NO:7.

A CYP72A15 amino acid sequence is disclosed by, e.g., GenBank Accession No. NP 001043632.1, which is herein incorporated by reference in its entirety. In one embodiment, the plant or plant part of the present invention comprises a recombinant polynucleotide encoding a CYP72A15 polypeptide, the expression of which confers to the plant or plant part tolerance to saflufenacil. In another embodiment, the CYP72A15 polypeptide is a rice polypeptide. In other embodiments, the CYP72A15 polypeptide has the amino acid sequence set forth in SEQ ID NO:7. The recombinant polynucleotide encoding the CYP72A15 polypeptide has the nucleic acid sequence set forth in SEQ ID NO:8.

Additional examples, without limitation, of cytochrome P450 amino acid sequences are set forth in SEQ ID NO:9 (TaCYP709C1), SEQ ID NO:10 (Os07g0635500), SEQ ID NO:11 (Os02g0467600), SEQ ID NO:12 (Os06g0569500), SEQ ID NO:13 (Os08g050800), SEQ ID NO:14 (Os12g0150200), SEQ ID NO:15 (ZM1S60596158), SEQ ID NO:16 (ZM4s40785), and SEQ ID NO:17 (ZM1s57311919). Their corresponding nucleic acid sequences set forth in SEQ ID NO:18 (TaCYP709C1), SEQ ID NO:19 (Os07g0635500), SEQ ID NO:20 (Os02g0467600), SEQ ID NO:21 (Os06g0569500), SEQ ID NO:22 (Os08g050800), SEQ ID NO:23 (Os12g0150200), SEQ ID NO:24 (ZM1S60596158), SEQ ID NO:25 (ZM4s40785), and SEQ ID NO:26 (ZM1s57311919).

In other embodiments, the cytochrome P450 polypeptide for use according to the present invention is a functional variant having, over the full-length of the variant, at least about 80%, illustratively, at least about 80%, 90%, 95%, 98%, 99% or more amino acid sequence identity to SEQ ID NO: 1, 3, 5, 7, or 29.

In another embodiment, the cytochrome P450 polypeptide for use according to the present invention is a functional fragment of a polypeptide having the amino acid sequence set forth in SEQ ID NO: 1, 3, 5, 7, or 29.

For polynucleotides, degenerate and codon-optimized sequences that encode the cytochrome P450 polypeptides also are within the scope of the present invention.

Thus, functional variants and fragments of the cytochrome polypeptides, and nucleic acid molecules encoding them, also are within the scope of the present invention, and unless specifically described otherwise, irrespective of the origin of the P450 polypeptide and irrespective of whether it occurs naturally.

Various assays for functionality of a P450 polypeptide can be employed. For example, a functional variant or fragment of the P450 polypeptide can be assayed to determine its ability to confer saflufenacil detoxification. By way of illustration, a saflufenacil detoxification rate can be defined as a catalytic rate sufficient to provide a determinable increase in tolerance to saflufenacil in a plant or plant part comprising a recombinant polynucleotide encoding the variant or fragment of the P450 polypeptide, wherein the plant or plant part expresses the variant or fragment at up to about 0.5%, illustratively, about 0.05 to about 0.5%, about 0.1 to about 0.4%, and about 0.2 to about 0.3%, of the total cellular protein relative to a similarly treated control plant that does not express the variant or fragment.

In some embodiments, the P450 polypeptide is a functional variant or fragment of a cytochrome having the amino acid sequence set forth in SEQ ID NO:1, 3, 5, 7 or 29, wherein the functional variant or fragment has at least about 80% amino acid sequence identity to SEQ ID NO:1, 3, 5, 7 or 29. In other embodiments, the functional variant or fragment further has a saflufenacil detoxification rate defined as a catalytic rate sufficient to provide a determinable increase in tolerance to saflufenacil in a plant or plant part comprising a recombinant polynucleotide encoding the variant or fragment, wherein the plant or plant part expresses the variant or fragment at up to about 0.5% of the total cellular protein to a similarly treated control plant that does not express the variant or fragment.

In addition, one of ordinary skill in the art will further appreciate that changes can be introduced by mutation into the nucleotide sequences of the invention thereby leading to changes in the amino acid sequence of the encoded proteins without altering the biological activity of the proteins. Thus, for example, an isolated polynucleotide molecule encoding a P450 polypeptide having an amino acid sequence that differs from that of SEQ ID NO: 1, 3, 5, 7, or 29 can be created by introducing one or more nucleotide substitutions, additions, or deletions into the corresponding nucleotide sequence, such that one or more amino acid substitutions, additions or deletions are introduced into the encoded protein. Mutations can be introduced by standard techniques, such as site-directed mutagenesis and PGR-mediated mutagenesis. Such variant nucleotide sequences are also encompassed by the present invention. For example, preferably, conservative amino acid substitutions may be made at one or more predicted preferably nonessential amino acid residues. A "nonessential" amino acid residue is a residue that can be altered from the wild-type sequence of a protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif.

The proteins of the invention may be altered in various ways including amino acid substitutions, deletions, truncations, and insertions. Methods for such manipulations are generally known in the art. For example, amino acid sequence variants can be prepared by mutations in the DNA. Methods for mutagenesis and nucleotide sequence alterations are well known in the art. See, for example, Kunkel (1985) PNAS, 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be preferable.

Alternatively, variant nucleotide sequences can be made by introducing mutations randomly along all or part of a coding sequence, such as by saturation mutagenesis, and the resultant mutants can be screened to identify mutants that encode proteins that retain activity. For example, following mutagenesis, the encoded protein can be expressed recombinantly, and the activity of the protein can be determined using standard assay techniques.

In other aspects, the present invention encompasses a progeny or a descendant of a saflufenacil-tolerant plant of the present invention as well as seeds derived from the saflufenacil-tolerant plants of the invention and cells derived from the saflufenacil-tolerant plants of the invention.

In some embodiments, the present invention provides a progeny or descendent plant derived from a plant comprising in at least some of its cells a recombinant polynucleotide operably linked to a promoter operable in plant cells, the promoter capable of expressing a CYP81A or CYP73A polypeptide encoded by the polynucleotide, the expression of the polypeptide conferring to the plant tolerance to saflufenacil, wherein the progeny or descendant plant comprises in at least some of its cells the recombinant polynucleotide operably linked to the regulatory sequence, the expression of the polypeptide in the progeny or descendant plant conferring to the progeny or descendant plant tolerance to the saflufenacil. In other embodiments, the recombinant polynucleotide encodes a CYP72A15 polypeptide, the expression of the polypeptide conferring to the plant tolerance to saflufenacil.

In one embodiment, seeds of the present invention preferably comprise the saflufenacil-tolerance characteristics of the saflufenacil-tolerant plant. In other embodiments, a seed is capable of germination into a plant comprising in at least some of its cells a recombinant polynucleotide operably linked to a promoter operable in plant cells, the promoter capable of expressing a CYP81A or CYP73A polypeptide encoded by the polynucleotide, the expression of the polypeptide conferring to the plant tolerance to saflufenacil. In other embodiments, the recombinant polynucleotide encodes a CYP72A15 polypeptide, the expression of the polypeptide conferring to the plant tolerance to saflufenacil.

In some embodiments, plant cells of the present invention are capable of regenerating a plant or plant part. In other embodiments, plant cells are not capable of regenerating a plant or plant part. Examples of cells not capable of regenerating a plant include, but are not limited to, endosperm, seed coat (testa & pericarp), and root cap.

In another embodiment, the present invention provides a plant cell of or capable of regenerating a plant comprising in at least some of its cells a recombinant polynucleotide operably linked to a promoter operable in plant cells, the promoter capable of expressing a CYP81A or CYP73A polypeptide encoded by the polynucleotide, the expression of the polypeptide conferring to the plant tolerance to saflufenacil, wherein the plant cell comprises the recombinant polynucleotide operably linked to a promoter. In other embodiments, the recombinant polynucleotide encodes a CYP72A15 polypeptide, the expression of the polypeptide conferring to the plant tolerance to saflufenacil.

In other embodiments, the present invention provides a plant cell comprising a recombinant polynucleotide operably linked to a promoter operable in the cell, the recombinant polynucleotide being effective in the cell to express a CYP81A or CYP73A polypeptide encoded by the polynucleotide, the expression of the polypeptide conferring to the cell tolerance to saflufenacil. In other embodiments, the recombinant polynucleotide encodes a CYP72A15 polypeptide, the expression of the polypeptide conferring to the cell tolerance to saflufenacil.

In some aspects, the present invention provides a plant product prepared from the saflufenacil-tolerant plants hereof. In some embodiments, examples of plant products include, without limitation, grain, oil, and meal. In one embodiment, a plant product is plant grain (e.g., grain suitable for use as feed or for processing), plant oil (e.g., oil suitable for use as food or biodiesel), or plant meal (e.g., meal suitable for use as feed).

In one embodiment, a plant product prepared from a plant or plant part is provided, wherein the plant or plant part comprises in at least some of its cells a recombinant polynucleotide operably linked to a promoter operable in plant cells, the recombinant polynucleotide being effective in the cells of the plant or plant part to express a CYP81A or CYP73A polypeptide encoded by the polynucleotide, the expression of the polypeptide conferring to the plant or plant part tolerance to saflufenacil. In other embodiments, the recombinant polynucleotide encodes a CYP72A15 polypeptide, the expression of the polypeptide conferring to the plant or plant part tolerance to saflufenacil.

In some aspects, the present invention provides a method for producing a saflufenacil-tolerant plant. In one embodiment, the method comprises: regenerating a plant from a plant cell transformed with a recombinant polynucleotide operably linked to a promoter operable in the cell, the recombinant polynucleotide being effective in the cell to express a CYP81A or CYP73A polypeptide encoded by the polynucleotide, the expression of the polypeptide conferring to the plant tolerance to the saflufenacil. In other embodiments, the recombinant polynucleotide encodes a CYP72A15 polypeptide, the expression of the polypeptide conferring to the plant tolerance to saflufenacil.

Where appropriate, nucleic acid sequences may be optimized for increased expression in a transformed plant. For example, coding sequences can be provided that comprise plant-preferred codons for improved expression in a plant. See, for example, Campbell and Gowri (1990) Plant Physiol., 92:1-11 for a discussion of host-preferred codon usage. Methods also are known in the art for preparing plant-preferred genes. See, for example, U.S. Pat. Nos. 5,380,831, and 5,436,391, and Murray et al. (1989) Nucleic Acids Res. 17:477-498, herein incorporated by reference. Further, additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. Also, if desired, sequences can be readily modified to avoid predicted hairpin secondary mRNA structures. Nucleotide sequences for enhancing gene expression can also be used in the plant expression vectors. These include, for example, the introns of the maize Adh1, intron1 gene (Callis et al. Genes and Development 1:1183-1200, 1987), and leader sequences, (W-sequence) from the Tobacco Mosaic virus (TMV), Maize Chlorotic Mottle Virus and Alfalfa Mosaic Virus (Gallie et al. Nucleic Acid Res. 15:8693-8711, 1987 and Skuzeski et al. Plant Mol. Biol. 15:65-79, 1990). The first intron from the shrunken-1 locus of maize, has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize gene expression, the plant expression vectors of the invention also may contain DNA sequences containing matrix attachment regions (MARs). Plant cells transformed with such modified expression systems, then, may exhibit overexpression or constitutive expression of a nucleotide sequence of the invention.

Expression vectors may additionally contain 5' leader sequences in the expression construct. Such leader sequences can act to enhance translation. Translation leaders are known in the art and include: picornavirus leaders, for example, EMCV leader (Encephalomyo carditis 5' noncoding region) (Elroy-Stein et al. (1989) PNAS, 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Jobling et al. (1987) Nature 325:622-625); tobacco mosaic virus leader (TMV) (Gallie et al. (1989) in Molecular Biology of RNA, ed. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968.

Other methods known to enhance translation also can be utilized, for example, introns, and the like. In preparing an expression vector, the various nucleic acid fragments may be manipulated, so as to provide for the nucleic acid sequences in the proper orientation and, as appropriate, in the proper reading frame. Toward this end, adapters or linkers may be employed to join the nucleic acid fragments or other manipulations may be involved to provide for convenient restriction sites, removal of superfluous nucleic acid, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to target enhanced expression within a particular plant tissue. Such tissue-preferred promoters include, but are not limited to, leaf-preferred promoters, root-preferred promoters, seed-preferred promoters, and stem-preferred promoters. Some examples of tissue-preferred promoters are described by, e.g., Yamamoto et al. (1997) Plant J. 12(2):255-265; Kawamata et al. (1997) Plant Cell Physiol. 38(7):792-803; Hansen et al. (1997) Mol. Gen Genet. 254(3):337-343; Russell et al. (1997) Transgenic Res. 6(2): 157-168; Rinehart et al. (1996) Plant Physiol. 112(3): 1331-1341; Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco ef a/. (1993) Plant Mol Biol. 23(6): 1129-1138; Matsuoka et al. (1993) Voc Natl. Acad. ScL USA 90(20):9586-9590; and Guevara-Garcia et al. (1993) Plant J 4(3):495-505. Promoters can be modified, if necessary, for weak expression.

In some embodiments, the nucleic acids of interest can be targeted to the chloroplast for expression. In this manner, where the nucleic acid of interest is not directly inserted into the chloroplast, the expression vector will additionally contain a chloroplast-targeting sequence comprising a nucleotide sequence that encodes a chloroplast transit peptide to direct the gene product of interest to the chloroplasts. Such transit peptides are known in the art. With respect to chloroplast-targeting sequences, "operably linked" means that the nucleic acid sequence encoding a transit peptide (i.e., the chloroplast-targeting sequence) is linked to the desired coding sequence of the invention such that the two sequences are contiguous and in the same reading frame. See, for example, Von Heijne et al. (1991) Plant Mol. Biol. Rep. 9:104-126; Clark et al. (1989) J Biol. Chem. 264: 17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481. For example, a chloroplast transit peptide known in the art can be fused to the amino acid sequence of a P450 polypeptide of the invention by operably linking a chloroplast-targeting sequence to the 5'-end of a nucleotide sequence encoding the P450.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J Biol. Chem. 266(5):3335-3342); EPSPS (Archer et al. (1990) J Bioenerg. Biomemb. 22(6):789-810); tryptophan synthase (Zhao et al. (1995) J Biol. Chem. 270(11):6081-6087); plastocyanin (Lawrence et al. (1997) J Biol. Chem. 272(33):20357-20363); chorismate synthase (Schmidt et al. (1993) J Biol. Chem. 268(36):27447-27457); and the light harvesting chlorophyll a/b binding protein (LHBP) (Lamppa et al. (1988) J Biol. Chem. 263:14996-14999). See also Von Heijne et al. (1991) Plant Mol. Biol. Rep. 9:104-126; Clark et al. (1989) J Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481.

Methods for transformation of chloroplasts are known in the art. See, for example, Svab et al. (1990) Proc. Natl. Acad. ScL USA 87:8526-8530; Svab and Maliga (1993) Proc. Natl. Acad. Sci. USA 90:913-917; Svab and Maliga (1993) EMBO J. 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Numerous plant transformation vectors and methods for transforming plants are available. See, for example, An, G. et al. (1986) Plant PysioL, 81:301-305; Fry, J., et al. (1987) Plant Cell Rep. 6:321-325; Block, M. (1988) Theor. Appl. Genet. 16:161-11 A; Hinchee, et al. (1990) Stadler. Genet. Symp. 2032\2.203-2\2; Cousins, et al. (1991) Aust. J. Plant Physiol. 18:481-494; Chee, P. P. and Slightom, J. L. (1992) Gene. 118:255-260; Christou, et al. (1992) Trends. Biotechnol. 10:239-246; Halluin, et al. (1992) Bio/Technol. 10:309-314; Dhir, et al. (1992) Plant Physiol. 99:81-88; Casas et al. (1993) Proc. Nat. Acad Sd. USA 90:11212-11216; Christou, P. (1993) In Vitro Cell. Dev. Biol.-Plant; 29P: 119-124; Davies, et al. (1993) Plant Cell Rep. 12:180-183; Dong, J. A. and Mchughen, A. (1993) Plant ScL 91:139-148; Franklin, C. I. and Trieu, T. N. (1993) Plant. Physiol. 102:167; Golovkin, et al. (1993) Plant ScL 90:41-52; Guo Chin ScL Bull. 38:2072-2078; Asano, et al. (1994) Plant Cell Rep. 13; Ayeres N. M. and Park, W. D. (1994) Crit. Rev. Plant. Sci. 13:219-239; Barcelo, et al. (1994) Plant. J. 5:583-592; Becker, et al. (1994) Plant. J. 5:299-307; Borkowska et al. (1994) Acta. Physiol Plant. 16:225-230; Christou, P. (1994) Agro. Food. Ind. Hi Tech. 5: 17-27; Eapen et al. (1994) Plant Cell Rep. 13:582-586; Hartman, et al. (1994) Bio-Technology 12: 919923; Ritala, et al. (1994) Plant. Mol. Biol. 24:317-325; and Wan, Y. C. and Lemaux, P. G. (1994) Plant Physiol. 104:3748.

In some embodiments, the methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by descendent thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed. In an embodiment of the invention, the encoding nucleotide sequence is operably linked to a plant promoter, e.g. a promoter known in the art for high-level expression in a plant cell, and this construct is then introduced into a plant cell that is susceptible to saflufenacil; and a transformed plant is regenerated. In some embodiments, the transformed plant is tolerant to exposure to a level of saflufenacil that would kill or significantly injure a plant regenerated from an untransformed cell. This method can be applied to any plant species or crops.

Methodologies for constructing plant expression vectors and introducing foreign nucleic acids into plants are generally known in the art. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et ah; Bilang et a (1991) Gene 100: 247-250; Scheid et ah, (1991) MoL Gen. Genet., 228: 104-112; Guerche et ah, (1987) Plant Science 52: 111-116; Neuhause et ah, (1987) Theor. Appl Genet. 75: 30-36; Klein et ah, (1987) Nature 327: 70-73; Howell et ah, (1980) Science 208:1265; Horsch et ah, (1985) Science 227: 1229-1231; DeBlock et ah, (1989) Plant Physiology 91: 694-701; Methods for Plant Molecular Biology (Weissbach and Weissbach, eds.) Academic Press, Inc. (1988) and Methods in Plant Molecular Biology (Schuler and Zielinski, eds.) Academic Press, Inc. (1989).

Other suitable methods of introducing nucleotide sequences into plant cells include microinjection as described by, e.g., Crossway et ah (1986) Biotechniques 4:320-334, electroporation as described by e.g., Riggs et ah (1986) Proc. Natl. Acad. ScL USA 83:5602-5606, *Agrobacterium*-mediated transformation as described by e.g., Townsend et. al., U.S. Pat. No. 5,563,055, Zhao et. al., U.S. Pat. No. 5,981,840, direct gene transfer as described by, e.g., Paszkowski et. al. (1984) EMBO J. 3:2717-2722, and ballistic particle acceleration as described by, e.g., U.S. Pat. Nos. 4,945,050; 5,879,918; 5,886,244; and 5,932,782; Tomes et. al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); McCabe et ah (1988) Biotechnology 6:923-926); and Lecl transformation (WO 00/28058). Also see, Weissinger et. al., (1988) Ann. Rev. Genet. 22:421-477; Sanford et. al., (1987) Particulate Science and Technology 5:27-37 (onion); Christou et. al., (1988) Plant Physiol. 87:671-674 (soybean); McCabe et. al., (1988) Bio/Technology 6:923-926 (soybean); Finer and McMullen (1991) In Vitro Cell Dev. Biol. 27P: 175-182 (soybean); Singh et. al, (1998) Theor. Appl. Genet. 96:319-324 (soybean); Datta et. al., (1990) Biotechnology 8:736-740 (rice); Klein et. al., (1988) PNAS, 85:4305-4309 (maize); Klein et. al., (1988) Biotechnology 6:559-563 (maize); U.S. Pat. Nos. 5,240,855; 5,322,783; and 5,324,646; Tomes et. al, (1995) "Direct DNA Transfer into Intact Plant Cells via Microprojectile Bombardment," in Plant Cell, Tissue, and Organ Culture Fundamental Methods, ed. Gamborg (Springer-Verlag, Berlin) (maize); Klein et. al., (1988) Plant Physiol. 91:440-444 (maize); Fromm et. al., (1990) Biotechnology 8:833-839 (maize); Hooykaas-Van Slogteren et. al., (1984) Nature (London) 311:763-764; Bowen et. al., U.S. Pat. No. 5,736,369 (cereals); Bytebier et. al., (1987) PNAS 84:5345-5349 (Liliaceae); De Wet et. al., (1985) in The Experimental Manipulation of Ovule Tissues, ed. Chapman et. al., (Longman, N.Y.), pp. 197-209 (pollen); Kaeppler et. al., (1990) Plant Cell Reports 9:415-418 and Kaeppler et. al., (1992) Theor. Apph Genet. 84:560-566 (whisker-mediated transformation); D'Halluin et. al., (1992) Plant Cell 4:1495-1505 (electroporation); Li et. al., (1993) Plant Cell Reports 12:250-255 and Christou and Ford (1995) Annals of Botany 75:407-413 (rice); Osjoda et. al., (1996) Nature Biotechnology 14:745-750 (maize via *Agrobacterium tumefaciens*); each of which is herein incorporated by reference.

In some embodiments, polynucleotides of the present invention may be introduced into plants by contacting plants with a virus or viral nucleic acids. Generally, such methods involve incorporating a polynucleotide construct of the invention within a viral DNA or RNA molecule. It is recognized that the polypeptides of the invention may be initially synthesized as part of a viral polyprotein, which later may be processed by proteolysis in vivo or in vitro to produce the desired recombinant polypeptide. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866, 785, 5,589,367 and 5,316,931; herein incorporated by reference. The cells that have been transformed may be grown into plants in accordance with conventional ways. See, for example, McCormick et a (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, monocots and dicots. Examples of plant species of interest include, but are not limited to, corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum, T. Turgidum* ssp. *durum*), soybean (*Glycine max*), tobacco (*Nicotiana tabacum*), potato (*Solarium tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. Preferably, plants of the present invention are crop plants (for example, sunflower, *Brassica* sp., cotton, sugar, beet, soybean, peanut, alfalfa, safflower, tobacco, corn, rice, wheat, rye, barley triticale, sorghum, millet, etc.).

In other aspects, saflufenacil-tolerant plants of the present invention can be employed as saflufenacil-tolerance trait donor lines for development, as by traditional plant breeding, to produce other varietal and/or hybrid crops containing such trait or traits. All such resulting variety or hybrids crops, containing the ancestral saflufenacil-tolerance trait or traits can be referred to herein as progeny or descendant of the ancestral, saflufenacil-tolerant line(s).

In other embodiments, the present invention provides a method for producing a saflufenacil-tolerant plant. The method comprises: crossing a first saflufenacil-tolerant plant with a second plant to produce a saflufenacil-tolerant progeny plant, wherein the first plant and the progeny plant comprise in at least some of their cells a recombinant polynucleotide operably linked to a promoter operable in plant cells, the recombinant polynucleotide being effective in the cells of the first plant to express a CYP81A or CYP73A polypeptide encoded by the polynucleotide, the expression of the polypeptide conferring tolerance to saflufenacil. In other embodiments, the recombinant polynucleotide encodes a CYP72A15 polypeptide, the expression of the polypeptide conferring tolerance to saflufenacil.

For example, in the case of *Brassica* A-, B-, and C-genome saflufenacil trait(s), these can be bred into *Brassica* species having a corresponding genome, e.g.: *B. napus* (AACC), *B. juncea*. (AABB), *B. oleracea* (CC), *B. rapa* (AA), *B. nigra* (BB), *B. carinata* (BBCC), and *Raphanobrassica* varieties that are progeny of a cross between any of the foregoing and a *Raphanus* spp., e.g., *Raphanobrassica* var. 'rabbage' (RRCC) from *B. oleracea*×*Raphanus sativus* or *Raphanobrassica* var. 'raparadish' (RRAA) from *B. rapa*×*Raphanus sativus*. Among these, *B. napus, B. rapa*, and *B. juncea* are of particular interest, with *B. napus* being preferred in some embodiments.

In some embodiments, traditional plant breeding is employed whereby the saflufenacil-tolerant trait is introduced in the progeny plant resulting therefrom. In one embodiment, the present invention provides a method for producing a saflufenacil-tolerant progeny plant, the method comprising: crossing a parent plant with a saflufenacil-tolerant plant to introduce the saflufenacil-tolerance characteristics of the saflufenacil-tolerant plant into the germplasm of the progeny plant, wherein the progeny plant has increased tolerance to the saflufenacil relative to the parent plant.

In other embodiments, the method further comprises the step of introgressing the saflufenacil-tolerance characteristics through traditional plant breeding techniques to obtain a descendent plant having the saflufenacil-tolerance characteristics.

In other embodiments, saflufenacil-tolerant characteristics/traits of the present invention can be stacked with any combination of plant characteristic(s)/trait(s) of interest to provide plants with a desired combination of characteristics/traits.

In other aspects, plants of the invention include those plants which, in addition to being saflufenacil-tolerant, have been subjected to further genetic modifications by breeding, mutagenesis or genetic engineering, e.g. have been rendered tolerant to applications of specific other classes of herbicides, such as AHAS inhibitors; auxinic herbicides; bleaching herbicides such as hydroxyphenylpyruvate dioxygenase (HPPD) inhibitors or phytoene desaturase (PDS) inhibitors; EPSPS inhibitors such as glyphosate; glutamine synthetase (GS) inhibitors such as glufosinate; protoporphyrinogen-IX oxidase (PPO) inhibitors other than saflufenacil ("other PPO inhibitors") (e.g., acifluorfen, butafenacil, carfentrazone, flufenpyrethyl, fomesafen, flumiclorac, flumioxazin, lactofen, oxadiargyl, oxadiazon, oxyfluorfen, sulfentrazone); lipid biosynthesis inhibitors such as acetyl CoA carboxylase (ACCase) inhibitors; or oxynil (i.e. bromoxynil or ioxynil) herbicides as a result of conventional methods of breeding or genetic engineering, Thus, saflufenacil-tolerant plants of the invention can be made resistant to multiple classes of herbicides through multiple genetic modifications, such as resistance to both glyphosate and glufosinate or to both glyphosate and a herbicide from another class such as HPPD inhibitors, AHAS inhibitors, or ACCase inhibitors. These herbicide resistance technologies are, for example, described in *Pest Management Science* (at volume, year, page): 61, 2005, 246; 61, 2005, 258; 61, 2005, 277; 61, 2005, 269; 61, 2005, 286; 64, 2008, 326; 64, 2008, 332; *Weed Science* 57, 2009, 108; *Australian Journal of Agricultural Research* 58, 2007, 708; *Science* 316, 2007, 1185; and references quoted therein.

For example, saflufenacil-tolerant plants of the invention, in some embodiments, may be tolerant to ACCase inhibitors, such as "dims" (e.g., cycloxydim, sethoxydim, clethodim, or tepraloxydim), "fops" (e.g., clodinafop, diclofop, fluazifop, haloxyfop, or quizalofop), and "dens" (such as pinoxaden); to auxinic herbicides, such as dicamba; to EPSPS inhibitors, such as glyphosate; to other PPO inhibitors; and to GS inhibitors, such as glufosinate.

In addition to these classes of inhibitors, saflufenacil-tolerant plants of the invention may also be tolerant to herbicides having other modes of action, for example, chlorophyll/carotenoid pigment inhibitors, cell membrane disruptors, photosynthesis inhibitors, cell division inhibitors, root inhibitors, shoot inhibitors, and combinations thereof.

Such tolerance traits may be expressed, e.g.: as mutant AHASL proteins, mutant ACCase proteins, mutant EPSPS proteins, or mutant glutamine synthetase proteins; or as mutant native, inbred, or transgenic aryloxyalkanoate dioxygenase (AAD or DHT), haloarylnitrilase (BXN), 2,2-dichloropropionic acid dehalogenase (DEH), glyphosate-N-acetyltransferase (GAT), glyphosate decarboxylase (GDC), glyphosate oxidoreductase (GOX), glutathione-5-transferase (GST), phosphinothricin acetyltransferase (PAT or bar), or cytochrome P450 (CYP450) proteins having an herbicide-degrading activity. Saflufenacil-tolerant plants hereof can also be stacked with other traits including, but not limited to, pesticidal traits such as Bt Cry and other proteins having pesticidal activity toward coleopteran, lepidopteran, nematode, or other pests; nutrition or nutraceutical traits such as modified oil content or oil profile traits, high protein or high amino acid concentration traits, and other trait types known in the art.

Furthermore, in other embodiments, saflufenacil-tolerant plants are also covered which are, by the use of recombinant DNA techniques and/or by breeding and/or otherwise selected for such characteristics, rendered able to synthesize one or more insecticidal proteins, especially those known from the bacterial genus *Bacillus*, particularly from *Bacillus thuringiensis*, such as δ-endotoxins, e.g. CryIA(b), CryIA (c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such streptomycete toxins; plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (*Coeloptera*), two-winged insects (*Diptera*), and moths (*Lepidoptera*) and to nematodes (*Nematoda*).

In some embodiments, expression of one or more protein toxins (e.g., insecticidal proteins) in the saflufenacil-tolerant plants is effective for controlling organisms that include, for example, members of the classes and orders: *Coleoptera* such as the American bean weevil *Acanthoscelides obtectus*; the leaf beetle *Agelastica alni*; click beetles (*Agriotes lin-* eatus, *Agriotes obscurus, Agriotes bicolor*); the grain beetle *Ahasverus advena*; the summer schafer *Amphimallon solstitialis*; the furniture beetle *Anobium punctatum; Anthonomus* spp. (weevils); the Pygmy mangold beetle *Atomaria linearis*; carpet beetles (*Anthrenus* spp., *Attagenus* spp.); the cowpea weevil *Callosobruchus maculates*; the fried fruit beetle *Carpophilus hemipterus*; the cabbage seedpod weevil *Ceutorhynchus assimilis*; the rape winter stem weevil *Ceutorhynchus picitarsis*; the wireworms *Conoderus vespertinus* and *Conoderus falli*; the banana weevil *Cosmopolites sordidus*; the New Zealand grass grub *Costelytra zealandica*; the June beetle *Cotinis nitida*; the sunflower stem weevil *Cylindrocopturus adspersus*; the larder beetle *Dermestes lardarius*; the corn rootworms *Diabrotica virgifera, Diabrotica virgifera virgifera*, and *Diabrotica barberi*; the Mexican bean beetle *Epilachna varivestis*; the old house borer *Hylotropes bajulus*; the lucerne weevil *Hypera postica*; the shiny spider beetle *Gibbium psylloides*; the cigarette beetle *Lasioderma serricorne*; the Colorado potato beetle *Leptinotarsa decemlineata; Lyctus* beetles (*Lyctus* spp.); the pollen beetle *Meligethes aeneus*; the common cockshafer *Melolontha melolontha*; the American spider beetle *Mezium americanum*; the golden spider beetle *Niptus hololeucus*; the grain beetles *Oryzaephilus surinamensis* and *Oryzaephilus Mercator*; the black vine weevil *Otiorhynchus sulcatus*; the mustard beetle *Phaedon cochleariae*, the crucifer flea beetle *Phyllotreta cruciferae*; the striped flea beetle *Phyllotreta striolata*; the cabbage steam flea beetle *Psylliodes chrysocephala; Ptinus* spp. (spider beetles); the lesser grain borer *Rhizopertha dominica*; the pea and been weevil *Sitona lineatus*; the rice and granary beetles *Sitophilus oryzae* and *Sitophilus granaries*; the red sunflower seed weevil *Smicronyx fulvus*; the drugstore beetle *Stegobium paniceum*; the yellow mealworm beetle *Tenebrio molitor*; the flour beetles *Tribolium castaneum* and *Tribolium confusum*; warehouse and cabinet beetles (*Trogoderma* spp.); the sunflower beetle *Zygogramma exclamationis; Dermaptera* (earwigs) such as the European earwig *Forficula auricularia* and the striped earwig *Labidura riparia; Dictyoptera* such as the oriental cockroach *Blatta orientalis*; the greenhouse millipede *Oxidus gracilis*; the beet fly *Pegomyia betae*; the frit fly *Oscinella frit*; fruitflies (*Dacus* spp., *Drosophila* spp.); Isoptera (termites) including species from the familes Hodotermitidae, Kalotermitidae, Mastotermitidae, Rhinotermitidae, Serritermitidae, Termitidae, Termopsidae; the tarnished plant bug *Lygus lineolaris*; the black bean aphid *Aphis fabae*; the cotton or melon aphid *Aphis gossypii*; the green apple aphid *Aphis pomi*; the *citrus* spiny whitefly *Aleurocanthus spiniferus*; the sweet potato whitefly *Bemesia tabaci*; the cabbage aphid *Brevicoryne brassicae*; the pear psylla *Cacopsylla pyricola*; the currant aphid *Cryptomyzus ribis*; the grape phylloxera *Daktulosphaira vitifoliae*; the *citrus* psylla *Diaphorina citri*; the potato leafhopper *Empoasca fabae*; the bean leafhopper *Empoasca Solana*; the vine leafhopper *Empoasca vitis*; the woolly aphid *Eriosoma lanigerum*; the European fruit scale *Eulecanium corni*; the mealy plum aphid *Hyalopterus arundinis*; the small brown planthopper *Laodelphax striatellus*; the potato aphid *Macrosiphum euphorbiae*; the green peach aphid *Myzus persicae*; the green rice leafhopper *Nephotettix cinticeps*; the brown planthopper *Nilaparvata lugens*; the hop aphid *Phorodon humuli*; the bird-cherry aphid *Rhopalosiphum padi*; the grain aphid *Sitobion avenae; Lepidoptera* such as *Adoxophyes orana* (summer fruit tortrix moth); *Archips podana* (fruit tree tortrix moth); *Bucculatrix pyrivorella* (pear leafminer); *Bucculatrix thurberiella* (cotton leaf perforator); *Bupalus piniarius* (pine looper); *Carpocapsa pomonella* (codling moth); *Chilo suppressalis* (striped rice borer); *Choristoneura fumiferana* (eastern spruce budworm); *Cochylis hospes* (banded sunflower moth); *Diatraea grandiosella* (southwestern corn borer); *Eupoecilia ambiguella* (European grape berry moth); *Helicoverpa armigera* (cotton bollworm); *Helicoverpa zea* (cotton bollworm); *Heliothis virescens* (tobacco budworm), *Homeosoma electellum* (sunflower moth); *Homona magnanima* (oriental tea tree tortrix moth); *Lithocolletis blancardella* (spotted tentiform leafminer); *Lymantria dispar* (gypsy moth); *Malacosoma neustria* (tent caterpillar); *Mamestra brassicae* (cabbage armyworm); *Mamestra configurata* (Bertha armyworm); *Operophtera brumata* (winter moth); *Ostrinia nubilalis* (European corn borer), *Panolis flammea* (pine beauty moth), *Phyllocnistis citrella* (*citrus* leafminer); *Pieris brassicae* (cabbage white butterfly); *Rachiplusia ni* (soybean looper); *Spodoptera exigua* (beet armyworm); *Spodoptera littoralis* (cotton leafworm); *Sylepta derogata* (cotton leaf roller); *Trichoplusia ni* (cabbage looper); Orthoptera such as the common cricket *Acheta domesticus*, tree locusts (*Anacridium* spp.), the migratory locust *Locusta migratoria*, the twostriped grasshopper *Melanoplus bivittatus*, the differential grasshopper *Melanoplus differentialis*, the redlegged grasshopper *Melanoplus femurrubrum*, the migratory grasshopper *Melanoplus sanguinipes*, the northern mole cricket *Neocurtilla hexadectyla*, the red locust *Nomadacris septemfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria*; Symphyla such as the garden symphylan *Scutigerella immaculata*; Thysanoptera such as the tobacco thrips *Frankliniella fusca*, the flower thrips *Frankliniella intonsa*, the western flower thrips *Frankliniella occidentalis*, the cotton bud thrips *Frankliniella schultzei*, the banded greenhouse thrips *Hercinothrips femoralis*, the soybean thrips *Neohydatothrips variabilis*, Kelly's *citrus* thrips *Pezothrips kellyanus*, the avocado thrips *Scirtothrips perseae*, the melon thrips *Thrips palmi*, and the onion thrips *Thrips tabaci*; and the like, and combinations comprising one or more of the foregoing organisms.

In some embodiments, expression of one or more protein toxins (e.g., insecticidal proteins) in the saflufenacil-tolerant plants is effective for controlling flea beetles, i.e. members of the flea beetle tribe of family *Chrysomelidae*, preferably against *Phyllotreta* spp., such as *Phyllotreta cruciferae* and/or *Phyllotreta triolata*. In other embodiments, expression of one or more protein toxins (e.g., insecticidal proteins) in the saflufenacil-tolerant plants is effective for controlling cabbage seedpod weevil, the Bertha armyworm, *Lygus* bugs, or the diamondback moth.

Furthermore, in one embodiment, saflufenacil-tolerant plants are also covered which are, e.g. by the use of recombinant DNA techniques and/or by breeding and/or otherwise selected for such traits, rendered able to synthesize one or more proteins to increase the resistance or tolerance of those plants to bacterial, viral or fungal pathogens. The methods for producing such genetically modified plants are generally known to the person skilled in the art.

Furthermore, in another embodiment, saflufenacil-tolerant plants are also covered which are, e.g. by the use of recombinant DNA techniques and/or by breeding and/or otherwise selected for such traits, rendered able to synthesize one or more proteins to increase the productivity (e.g. oil content), tolerance to drought, salinity or other growth-limiting environmental factors or tolerance to pests and fungal, bacterial or viral pathogens of those plants.

Furthermore, in other embodiments, saflufenacil-tolerant plants are also covered which are, e.g. by the use of recombinant DNA techniques and/or by breeding and/or otherwise selected for such traits, altered to contain a modified amount of one or more substances or new substances, for example, to improve human or animal nutrition, e.g. oil crops that produce health-promoting long-chain omega-3 fatty acids or unsaturated omega-9 fatty acids (e.g. Nexera® rape, Dow Agro Sciences, Canada).

Furthermore, in some embodiments, saflufenacil-tolerant plants are also covered which are, e.g. by the use of recombinant DNA techniques and/or by breeding and/or otherwise selected for such traits, altered to contain increased amounts of vitamins and/or minerals, and/or improved profiles of nutraceutical compounds.

In one embodiment, saflufenacil-tolerant plants of the present invention, relative to a wild-type plant, comprise an increased amount of, or an improved profile of, a compound selected from the group consisting of: glucosinolates (e.g., glucoraphanin (4-methylsulfinylbutyl-glucosinolate), sulforaphane, 3-indolylmethyl-glucosinolate (glucobrassicin), 1-methoxy-3-indolylmethyl-glucosinolate (neoglucobrassicin)); phenolics (e.g., flavonoids (e.g., quercetin, kaempferol), hydroxycinnamoyl derivatives (e.g., 1,2,2'-trisinapoylgentiobiose, 1,2-diferuloylgentiobiose, 1,2'-disinapoyl-2-feruloylgentiobiose, 3-O-caffeoyl-quinic (neochlorogenic acid)); and vitamins and minerals (e.g., vitamin C, vitamin E, carotene, folic acid, niacin, riboflavin, thiamine, calcium, iron, magnesium, potassium, selenium, and zinc).

In another embodiment, saflufenacil-tolerant plants of the present invention, relative to a wild-type plant, comprise an increased amount of, or an improved profile of, a compound selected from the group consisting of: progoitrin; isothiocyanates; indoles (products of glucosinolate hydrolysis); glutathione; carotenoids such as beta-carotene, lycopene, and the xanthophyll carotenoids such as lutein and zeaxanthin; phenolics comprising the flavonoids such as the flavonols (e.g. quercetin, rutin), the flavans/tannins (such as the procyanidins comprising coumarin, proanthocyanidins, catechins, and anthocyanins); flavones; phytoestrogens such as coumestans, lignans, resveratrol, isoflavones e.g. genistein, daidzein, and glycitein; resorcyclic acid lactones; organosulphur compounds; phytosterols; terpenoids such as carnosol, rosmarinic acid, glycyrrhizin and saponins; chlorophyll; chlorophyllin, sugars, anthocyanins, and vanilla.

In other embodiments, saflufenacil-tolerant plants of the present invention, relative to a wild-type plant, comprise an increased amount of, or an improved profile of, a compound selected from the group consisting of: vincristine, vinblastine, taxanes (e.g., taxol (paclitaxel), baccatin III, 10-desacetylbaccatin III, 10-desacetyl taxol, xylosyl taxol, 7-epitaxol, 7-epibaccatin III, 10-desacetylcephalomannine, 7-epicephalomannine, taxotere, cephalomannine, xylosyl cephalomannine, taxagifine, 8-benxoyloxy taxagifine, 9-acetyloxy taxusin, 9-hydroxy taxusin, taiwanxam, taxane Ia, taxane Ib, taxane Ic, taxane Id, GMP paclitaxel, 9-dihydro 13-acetylbaccatin III, 10-desacetyl-7-epitaxol, tetrahydrocannabinol (THC), cannabidiol (CBD), genistein, diadzein, codeine, morphine, quinine, shikonin, ajmalacine, serpentine, and the like.

In one embodiment, saflufenacil-tolerant plants of the invention also can be tolerant to herbicides that inhibit acetohydroxyacid synthase (AHAS). As used herein, "herbicide tolerant AHASL" refers to the AHAS large subunit polypeptide expressed from one mutant AHASL allele of an AHASL gene in a plant cell and/or from either or both of two homologous alleles of the same mutant AHASL gene, i.e. in the same genome of, the plant cell, whereby that mutant AHASL can provide herbicide tolerance to an AHAS enzyme of the plant cell. A mutant AHASL gene can be recombinant, or can be obtained by application of a mutagenesis process, a breeding process, or other process known in the art. Such a gene can be hemizygous, heterozygous, or homozygous.

As used herein, "AHAS" and "AHASL" respectively refer to functional, plastidic AHAS enzymes and AHASL polypeptides thereof, i.e. which are functional in cells of the plants as described herein. Similarly, terms such as "gene" and "polynucleotide," when used in reference to those encoding such an "AHAS" and "AHASL," refer to functional genes therefor, i.e. genes that are expressible in such a cell.

As used herein, standard one letter abbreviations for amino acids will be used, for example, A indicates alanine, P indicates proline, W indicates tryptophan, X indicates any amino acid, etc. Mutations as compared to the wild-type sequence will be indicated by specifying the wild-type amino acid and position followed by the amino acid present in the mutant. For example, P197X will be used to indicate that the proline at position 197 can be substituted with any amino acid.

For ease of understanding, when referring to amino acid positions in an AHASL, the amino acid numbering system used herein may be the industry standard numbering used for the *Arabidopsis thaliana* (At) AHASL sequence, and can be denoted with an (At). For example, P197(At) can refer to the proline residue at the position in a plant AHASL that corresponds to the proline at position 197 of the *Arabidopsis thaliana* AHASL.

As used herein, an AHAS herbicide-tolerance-inducing mutation is an alteration in the amino acid sequence of an AHASL enzyme that confers tolerance to one or more herbicides (i.e., sulfonylurea herbicides, imidazolinone herbicides, etc).

The following Table 1 provides a non-limiting list of possible sites for AHASL mutations, permissible substitutions, preferred substitutions, and more preferred substitutions. X indicates any amino acid.

TABLE 1

AHASL Mutations

| w/t (At) | Permissible Sub. | Pref. Sub. | More. Pref. |
|---|---|---|---|
| G121 | X | NSAD | |
| A122 | X | TVDPY (or X) | TV |
| M124 | X | EI | |
| R142 | X | K | |
| V196 | X | M | |
| P197 | X | SAELQRSVWYIHCG | SLT |
| R199 | X | AS | AE |
| T203 | X | I | |
| A205 | X | VCDERTWYN | V |
| F206 | X | RAHWY | |
| K256 | X | DENPTG | |
| M351 | X | CKVGPQY | |
| H352 | X | FMQ | |
| R373 | X | F | |
| D375 | X | NAE | |
| D376 | X | EVNGPSWAC | |
| R377 | X | K | |
| M570 | X | ANC | |
| V571 | X | ACNYIQ SW | |
| W574 | X | LMCSRGAFQY | L |
| F578 | X | CGLNRDEIKPSW | |
| S653 | X | NIFT | N |
| G654 | X | QCED | E |

In some embodiments, AHASL mutations can be selected from the group consisting of A122X, P197X, R199X, A205X, S653X, and G654X, and combinations thereof. In other embodiments, AHASL mutations can be selected from the group consisting of A122T, A122V, A122D, A122P, A122Y, P197S, P197L, P197T, R199A, R199E, A205V, A205C, A205D, A205E, A205R, A205T, A205W, A205Y, A205N, S653N, S653I, S653F, S653T, G654Q, G654C, W574L, W574M, W574C, W574S, W574R, W574G, W574A, W574F, W574Q, W574Y, G654E, G654D and combinations thereof. In some embodiments, AHASL mutations can be selected from the group consisting of A122T, A122V, R199A, R199E, A205V, S653N, G654E, and combinations thereof.

In various embodiments, saflufenacil-tolerant plants may further comprise an AHASL containing both a W514(At)X and a S653(At)X in plastidic AHASL polypeptides. These AHASL mutations can be present in different alleles, such as on different genomes, with each containing a single mutation in the respective AHASL gene, or these two can be present in a single AHASL, as double-mutant allele. In various embodiments, these can be W574(At)L and S653(At)N: the former can be referred to as the "PM2" mutation and the latter as the "PM1" mutation.

In some embodiments, the saflufenacil-tolerant plants hereof can be inbred varieties, e.g., open-pollinated varieties, or hybrids, e.g., F1 hybrids.

In various embodiments, the AHAS trait or traits can be obtained by a process, excluding recombinant DNA techniques, and comprising mutagenesis, genoplasty, and/or isolation of spontaneous mutant plants. Many mutagenesis techniques are known in the art and these can involve application of a mutagenic chemical agent or radiation to seeds, plants parts, or cultured plant cells; alternatively, or in addition, the culturing of plant cells, or the conditions under which plant cells are cultured, can increase the rate of occurrence or accumulation of spontaneous mutations. Genoplasty techniques can include directed mutation-type strategies, such as methods comprising introduction, into the plant cell nucleus, of oligonucleotides that facilitate mismatch-repair-system-mediated nucleotide substitution.

In other aspects, the present invention provides saflufenacil-tolerant plants further comprising tolerance to at least one ACCase inhibitor herbicide at levels that would normally inhibit the growth of wild-type plant. In some embodiments, the saflufenacil-tolerant plant of the present invention expresses an ACCase in which the amino acid sequence differs from an amino acid sequence of an ACCase of a wild-type plant.

For ease of understanding, when referring to amino acid positions in an ACCase, the amino acid numbering system used herein may be the industry standard numbering system used for the ACCase from *Alopecurus myosuroides* [Huds.] (also referred to as black grass). The mRNA (cDNA) sequence encoding the *A. myosuroides* ACCase is available at GenBank Accession No. AJ310767 and the protein sequence is available at GenBank Accession No. CAC84161 both of which are specifically incorporated herein by reference. The number of the amino acid referred to will be followed with (Am) to indicate the amino acid in the *Alopecurus myosuroides* sequence to which the amino acid corresponds.

SEQ ID NO:27 and FIG. 1 each show the *Alopecurus myosuroides* ACCase amino acid sequence GenBank accession no. CAC84161. Amino acids that can be altered in the ACCase enzymes of the invention are indicted in bold double underline in FIG. 1.

Examples of amino acid positions at which an ACCase of a saflufenacil-tolerant plant of the invention differs from the ACCase of the corresponding wild-type plant include, but are not limited to, one or more of the following positions: 1,781(Am), 1,785(Am), 1,786(Am), 1,811(Am), 1,824 (Am), 1,864(Am), 1,999(Am), 2,027 (Am), 2,039(Am), 2,041(Am), 2,049(Am), 2,059(Am), 2,074(Am), 2,075 (Am), 2,078(Am), 2,079 (Am), 2,080(Am), 2,081(Am), 2,088(Am), 2,095(Am), 2,096(Am), or 2,098(Am).

In other aspects, a method for treating a plant of the present invention is provided. In some embodiments, the method comprises contacting the plant with an agronomically acceptable composition. In one embodiment, the agronomically acceptable composition comprises an auxinic herbicide A.I.

In another aspect, the present invention provides a method for preparing a descendent seed. The method comprises planting a seed of or capable of producing a plant of the present invention. In one embodiment, the method further comprises growing a descendent plant from the seed; and harvesting a descendant seed from the descendent plant. In other embodiments, the method further comprises applying a saflufenacil herbicidal composition to the descendent plant.

In still further aspects, the present invention provides a method for producing a plant product. In some embodiments, the method comprises processing a plant or plant part thereof of the present invention. In some embodiments, the plant product is fodder, seed meal, oil, or seed-treatment-coated seeds. In other embodiments, the plant part is a seed.

Herbicides

In some embodiments, herbicidal compositions of the invention comprise saflufenacil and its agronomically acceptable salts and esters. As used herein "saflufenacil" includes the compound saflufenacil and its salts and esters, unless expressly stated otherwise. In one embodiment, the saflufenacil A.I. is, e.g., IUPAC: 2-chloro-5-[3,6-dihydro-3-methyl-2,6-dioxo-4-(trifluoromethyl)-1(2H)-pyrimidinyl]-4-fluoro-N-[[methyl(1-methyl ethyl)amino]sulfonyl]benzamide (CAS: N'-{2-chloro-4-fluoro-5-[1,2,3,6-tetrahydro-3-methyl-2,6-dioxo-4-(trifluoromethyl)pyrimidin-1-yl] benzoyl}-N-isopropyl-N-methylsulfamide; Reg. No.: 372137-35-4); BAS-H800).

Post-emergent weed control methods useful in various embodiments hereof utilize about ≥0.3× application rates of saflufenacil; in some embodiments, this can be about, for example, ≥0.3×, ≥0.4×, ≥0.5×, ≥0.6×, ≥0.7×, ≥0.8×, ≥0.9×, or ≥1× of saflufenacil.

In one embodiment, saflufenacil-tolerant plants of the present invention have tolerance to a post-emergant application of a saflufenacil at an amount of about 25 to about 200 g ai/h.

In some embodiments, wherein the saflufenacil-tolerant plant is a dicot (e.g., soy, cotton), the post-emergant application of the saflufenacil is at an amount of about 50 g i/h.

In another embodiment, wherein the saflufenacil-tolerant plant is a monocot (e.g., maize, rice, *sorghum*), the post-emergant application of the saflufenacil is at an amount of about 200 g i/h.

In other embodiments, wherein the saflufenacil-tolerant plant is a *Brassica* (e.g., canola), the post-emergant application of the saflufenacil is at an amount of about 25 g i/h.

In post-emergent weed control methods hereof, in some embodiments, the method can utilize saflufenacil application rates at about 7 to 10 days post-emergent.

In another embodiment, the application rate can exceed 1× saflufenacil; in some embodiments, the rate can be up to 4× saflufenacil, though more typically it will be about 2.5× or less, or about 2× or less, or about 1× or less.

In other embodiments, in addition to the one or more saflufenacil A.I.(s), the herbicidal compositions of the invention, optionally, can further comprise one or more agronomically acceptable A.I.(s) other than saflufenacil. As used herein, agronomically acceptable A.I.(s) include the A.I.s and their agronomically acceptable salts and esters. Additional classes of herbicides include, but are not limited to, AHAS inhibitors; bleaching herbicides such as hydroxyphenylpyruvate dioxygenase (HPPD) inhibitors or phytoene desaturase (PDS) inhibitors; enolpyruvyl shikimate 3-phosphate synthase (EPSPS) inhibitors such as glyphosate; glutamine synthetase (GS) inhibitors such as glufosinate; auxinic herbicides; lipid biosynthesis inhibitors such as ACCase inhibitors; or oxynil (i.e. bromoxynil or ioxynil) herbicides. AHAS-inhibitor herbicides include, e.g., imidazolinone herbicides, one or more SU herbicides selected from the group consisting of amidosulfuron, flupyrsulfuron, foramsulfuron, imazosulfuron, iodosulfuron, mesosulfuron, nicosulfuron, thifensulfuron, and tribenuron, agronomically acceptable salts and esters thereof, and combinations thereof. ACCase inhibitor herbicides include, e.g., "dims" (e.g., cycloxydim, sethoxydim, clethodim, or tepraloxydim), "fops" (e.g., clodinafop, diclofop, fluazifop, haloxyfop, or quizalofop), and "dens" (such as pinoxaden). In addition to the one or more saflufenacils, the herbicide compositions of the invention, optionally, can further comprise one or more agronomically acceptable A.I.(s) of other classes, e.g., agronomic fungicides, bactericides, algicides, nematicides, insecticides, and the like (e.g., malathion, pyrethrins/pyrethrum, carbaryl, spinosad, permethrin, bifenthrin, and esfenvalerate).

The herbicidal compositions hereof comprising one or more saflufenacils, and optionally other agronomic A.I.(s) can be used in any agronomically acceptable format. For example, these can be formulated as ready-to-spray aqueous solutions, powders, suspensions; as concentrated or highly concentrated aqueous, oily or other solutions, suspensions or dispersions; as emulsions, oil dispersions, pastes, dusts, granules, or other broadcastable formats. The herbicide compositions can be applied by any method known in the art, including, for example, spraying, atomizing, dusting, spreading, watering, seed treatment, or co-planting in admixture with the seed. The use forms depend on the intended purpose; in any case, they should ensure the finest possible distribution of the A.I.s according to the invention. In some embodiments, an herbicidal composition hereof can comprise, e.g., a combination of: saflufenacil(s); AHAS-inhibitor(s), e.g., imidazolinone(s) and/or sulfonylurea(s); ACCase-inhibitor(s); EPSPS inhibitor(s), e.g., glyphosate; glutamine synthetase inhibitor(s), e.g., glufosinate; auxinic herbicide(s), e.g., dicamba; fungicide(s), e.g., strobilurin fungicide(s) such as pyraclostrobin; and the like. In some embodiments, an herbicidal composition hereof can comprise, e.g., a combination of saflufenacil(s); and strobilurin fungicide(s) such as pyraclostrobin(s). An herbicidal composition will be selected according to the tolerances of a plant hereof, and the plant can be selected from among those having stacked tolerance traits.

In some embodiments, where the optional A.I. includes an AHAS-inhibitor, this can be selected from: (1) the imidazolinones, e.g. imazamox, imazethapyr, imazapyr, imazapic, imazaquin, and imazamethabenz, preferably from imazamox, imazethapyr, imazapyr, and imazapic, preferably imazamox; (2) the SUs, e.g. amidosulfuron, flupyrsulfuron, foramsulfuron, imazosulfuron, iodosulfuron, mesosulfuron, nicosulfuron, thifensulfuron, and tribenuron; (2) the pyrimidinyloxy[thio]benzoates, e.g. including the pyrimidinyloxybenzoates (e.g., bispyribac, pyriminobac, and pyribenzoxim) and the pyrimidinylthiobenzoates (e.g., pyrithiobac and pyriftalid); and (3) the sulfonamides, i.e. including the sulfonylaminocarbonyltriazolinones (e.g., flucarbazone and propoxycarbazone) and the triazolopyrimidines (e.g., cloransulam, diclosulam, florasulam, flumetsulam, metosulam, and penoxsulam). The agronomically acceptable salts and esters of the foregoing are also included, as are combinations thereof.

In other embodiments, where the optional A.I. includes an herbicide from a different class to which the plant(s) hereof would normally be susceptible, the plant to be used is selected from among those that further comprise a trait of tolerance to such herbicide. Such further tolerance traits can be provided to the plant by any method known in the art, e.g., including techniques of traditional breeding to obtain a tolerance trait gene by hybridization or introgression, of mutagenesis, and/or of transformation. Such plants can be described as having "stacked" traits.

Optional A.I.s of other herbicide classes include ACCase inhibitors, auxinic herbicides, EPSPS inhibitors, glutamine synthetase inhibitors, p-hydroxyphenylpyruvate dioxygenase (4-HPPD) inhibitors. Optional A.I.s of other types include, but are not limited to fungicides such as strobilurins, e.g., pyraclostrobin, alone or in combination with, e.g., boscalid, epiconazole, metaconazole, tebuconazole, kresoxim-methyl, and the like; insecticides such as nematicides, lepidoptericides, coleoptericides; molluskicides), and others known in the art.

For example, suitable examples of herbicides that are ACCase inhibitors include, but are not limited to, cyclohexanedione herbicides (DIMS, also referred to as: cyclohexene oxime cyclohexanedione oxime; and CHD), aryloxyphenoxy propionate herbicides (also referred to as aryloxyphenoxy propanoate; aryloxyphenoxyalkanoate; oxyphenoxy; APP; AOPP; APA; APPA; FOP, note that these are sometime written with the suffix '-oic'), and phenylpyrazole herbicides (also known as DENs; and sometimes referred to under the more general class of Phenylpyrazole such as pinoxaden (e.g., herbicides sold under the trade names Axial and Traxos)). In some methods of controlling weeds and/or growing herbicide-tolerant plants, at least one herbicide is selected from the group consisting of sethoxydim, cycloxydim, tepraloxydim, haloxyfop, haloxyfop-P or a derivative of any of these herbicides. Table 2 is a list of herbicides that interfere with ACCase activity.

TABLE 2

Examples of ACCase inhibitors

| ACCase inhibitor | Class | Company | Examples of Synonyms and Trade Names |
|---|---|---|---|
| alloxydim | DIM | BASF | Fervin, Kusagard, NP-48Na, BAS 9021H, Carbodimedon, Zizalon |
| Butroxydim | DIM | Syngenta | Falcon, ICI-A0500, Butroxydim |
| clethodim | DIM | Valent | Select, Prism, Centurion, RE-45601, Motsa |

TABLE 2-continued

Examples of ACCase inhibitors

| ACCase inhibitor | Class | Company | Examples of Synonyms and Trade Names |
|---|---|---|---|
| Clodinafop-propargyl | FOP | Syngenta | Discover, Topik, CGA 184 927 |
| clofop | FOP | | Fenofibric Acid, Alopex |
| cloproxydim | FOP | | |
| chlorazifop | FOP | | |
| cycloxydim | DIM | BASF | Focus, Laser, Stratos, BAS 517H |
| cyhalofop-butyl | FOP | Dow | Clincher, XDE 537, DEH 112, Barnstorm |
| diclofop-methyl | FOP | Bayer | Hoegrass, Hoelon, Illoxan, HOE 23408, Dichlorfop, Illoxan |
| fenoxaprop-P-ethyl | FOP | Bayer | Super Whip, Option Super, Exel Super, HOE46360,- Aclaim, Puma S, Fusion |
| fenthiaprop | FOP | | Taifun; Joker |
| fluazifop-P-butyl | FOP | Syngenta | Fusilade, Fusilade 2000, Fusilade DX, IC-A 0009, IC-A 0005, SL-236, IH-773B, TF-1169, Fusion |
| haloxyfop-etotyl | FOP | Dow | Gallant, DOWCO 453EE |
| haloxyfop-methyl | FOP | Dow | Verdict, DOWCO 453ME |
| haloxyfop-P-methyl | FOP | Dow | Edge, DE 535 |
| isoxapyrifop | FOP | | |
| Metamifop | FOP | Dongbu | NA |
| pinoxaden | DEN | Syngenta | Axial |
| profoxydim | DIM | BASF | Aura, Tetris, BAS 625H, Clefoxydim |
| propaquizafop | FOP | Syngenta | Agil, Shogun, Ro 17-3664, Correct |
| quizalofop-P-ethyl | FOP | DuPont | Assure, Assure II, DPX-Y6202-3, Targa Super, NC-302, Quizafop |
| quizalofop-P-tefuryl | FOP | Uniroyal | Pantera, UBI C4874 |
| sethoxydim | DIM | BASF | Poast, Poast Plus, NABU, Fervinal, NP-55, Sertin, BAS 562H, Cyethoxydim, Rezult |
| tepraloxydim | DIM | BASF | BAS 620H, Aramo, Caloxydim |
| tralkoxydim | DIM | Syngenta | Achieve, Splendor, ICI-A0604, Tralkoxydime, Tralkoxidym |
| trifop | FOP | | |

Examples of herbicides that are auxinic herbicides include, but are not limited to, the auxinic herbicides shown in Table 3.

TABLE 3

Auxinic herbicides
Classification of Auxinic Herbicides
(HRAC Group '0'; WSSA Group '4')

| Subgroup | Member Compound |
|---|---|
| Phenoxy-carboxylic-acid Subgroup | Clomeprop
cloprop ("3-CPA")
4-chlorophenoxyacetic acid ("4-CPA")
2-(4-chlorophenoxy)propionic acid ("4-CPP")
2,4-dichlorophenoxy acetic acid ("2,4-D")
(3,4-dichlorophenoxy)acetic acid ("3,4-DA")
4-(2,4-dichlorophenoxy)butyric acid ("2,4-DB")
2-(3,4-dichlorophenoxy)propionic acid ("3,4-DP")
tris[2-(2,4-dichlorophenoxy)ethyl]phosphite ("2,4-DEP")
dichlorprop ("2,4-DP")
2,4,5-trichlorophenoxyacetic acid ("2,4,5-T")
fenoprop ("2,4,5-TP")
2-(4-chloro-2-methylphenoxy)acetic acid ("MCPA")
4-(4-chloro-2-methyl phenoxy)butyric acid ("MCPB")
mecoprop ("MCPP") |
| Benzoic acid Subgroup | Chloramben
Dicamba
Tricamba
2,3,6-trichlorobenzoic acid ("TBA") |
| Pyridine carboxylic acid Subgroup | Aminopyralid
Clopyralid
Fluroxypyr
Picloram
Triclopyr |

TABLE 3-continued

Auxinic herbicides
Classification of Auxinic Herbicides
(HRAC Group '0'; WSSA Group '4')

| Subgroup | Member Compound |
|---|---|
| Quinoline carboxylic acid Subgroup | Quinclorac
Quinmerac |
| Other Subgroup | Benazolin |

The herbicidal compositions comprising a saflufenacil, and optionally other agronomic A.I.(s) and/or their agriculturally suitable salts and esters can also comprise auxiliaries which are customary for the formulation of crop protection agents.

Examples of auxiliaries customary for the formulation of crop protection agents include inert auxiliaries, solid carriers, surfactants (such as dispersants, protective colloids, emulsifiers, wetting agents and tackifiers), organic and inorganic thickeners, penetrants (such as penetration-enhancing organosilicone surfactants or acidic sulfate chelates, e.g., CT-301™ available from Cheltec, Inc.), safeners, bactericides, antifreeze agents, antifoams, colorants, and adhesives. Formulations of the herbicide compositions useful herein can be prepared according to any method known useful therefor in the art Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants include members of colorant classes such as the sparingly water-soluble pigments and the water-soluble dyes. Some specific examples of these include the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers.

Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g. methylcellulose), hydrophobically modified starches, polyvinyl alcohol (Mowiol types, Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Powders, materials for broadcasting and dusts can be prepared by mixing or concomitant grinding the A.I.s together with a solid carrier.

Granules, for example coated granules, impregnated granules and homogeneous granules, can be prepared by binding the A.I.s to solid carriers.

Aqueous use forms can be prepared from emulsion concentrates, suspensions, pastes, wettable powders or water-dispersible granules by adding water.

To prepare emulsions, pastes or oil dispersions, the herbicidal compositions comprising an auxinic herbicide, and optionally other agronomic A.I.(s) and/or their agriculturally suitable salts and esters, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of the herbicides present in the herbicidal composition comprising an auxinic herbicide, and optionally other agronomic A.I.(s) and/or their agriculturally suitable salts and esters can be varied within wide ranges. In general, the formulations comprise approximately from 0.001 to 98% by weight, preferably 0.01 to 95% by weight of at least one active ingredient. The A.I.s are employed in a purity of from 90% to 100%, preferably 95% to 100% (according to NMR spectrum).

In the formulation, in some embodiments, the herbicides are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

In various embodiments, the herbicides can, for example, be formulated as follows:

1. Products for Dilution with Water

A Water-Soluble Concentrates 10 parts by weight of active compound are dissolved in 90 parts by weight of water or a water-soluble solvent. As an alternative, wetting agent(s) or other adjuvants are added. The active compound dissolves upon dilution with water. This gives a formulation with an active compound content of 10% by weight.

B Dispersible Concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (e.g. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetting agent(s) and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound are ground finely with addition of 50 parts by weight of dispersants and wetting agent(s) and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound are ground in a rotor-stator mill with addition of 25 parts by weight of dispersants, wetting agent(s) and silica gel. Dilution with water gives a stable dispersion or solution of the active compound. The active compound content of the formulation is 75% by weight.

H Gel Formulations

In a ball mill, 20 parts by weight of active compound, 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

The herbicides or the herbicidal compositions comprising them can be applied pre-, post-emergence or pre-plant, or together with the seed. It is also possible to apply the herbicidal composition or active compounds by applying seed, pretreated with the herbicidal compositions or active compounds, of a crop plant.

In a further embodiment, the herbicides or herbicidal compositions can be applied by treating seed. The treatment of seeds comprises essentially all procedures familiar to the person skilled in the art (e.g., seed dressing, seed coating, seed dusting, seed soaking, seed film coating, seed multi-layer coating, seed encrusting, seed dripping and seed pelleting). In some embodiments, the herbicidal compositions can be applied diluted or undiluted.

In one embodiment, the saflufenacil(s) and optionally other agronomic A.I.(s), can be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexane-diones, 2-hetaroyl-1,3-cyclohexane-diones, hetaryl aryl ketones, benzylisoxazolidinones, meta-CF3-phenyl derivatives, carbamates, quinolinecarboxylic acid and its derivatives, chloroacetanilides, cyclohexenone oxime ether derivatives, diazines, dichloropropionic acid and its derivatives, dihydro-benzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazole-carboxamides, uracils, phenyl pyrazolines and isoxazolines and derivatives thereof. For the purposes of this paragraph, auxinic herbicide members are excluded from the following classes: benzoic acid and its derivatives; quinolinecarboxylic acid and its derivatives; 2-phenylpropionic acid and its derivatives; and pyridinecarboxylic acid and its derivatives.

It may furthermore be beneficial to apply the herbicides alone or in combination with other herbicides, or else in the form of a mixture with other crop protection agents, for example together with agents for controlling pests or phylopathogenic fungi or bacteria. Also of interest is the miscibility with mineral salt solutions, which are employed for treating nutritional and trace element deficiencies. Other additives such as non-phytotoxic oils and oil concentrates can also be added.

Moreover, it may be useful to apply the herbicides in combination with safeners. Safeners are chemical compounds which prevent or reduce herbicide-induced injury to useful plants without having a major impact on the herbicidal action of the herbicides. They can be applied either before sowings (e.g. on seed treatments, shoots or seedlings) or in the pre-emergence application or post-emergence application of the useful plant. The safeners and the herbicides can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of saferners are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Those skilled in the art will recognize that some of the above mentioned herbicides and/or safeners are capable of forming geometrical isomers, for example E/Z isomers. It is possible to use both, the pure isomers and mixtures thereof, in the compositions according to the invention. Furthermore, some of the above mentioned herbicides and/or safeners have one or more centers of chirality and, as a consequence, are present as enantiomers or diastereomers. It is possible to use both, the pure enantiomers and diastereomers and their mixtures, in the compositions according to the invention. In particular, some of the aryloxyphenoxy propionate herbicides are chiral, and some of them are commonly used in enantiomerically enriched or enantiopure form, e.g. clodinafop, cyhalofop, fenoxaprop-P, fluazifop-P, haloxyfop-P, metamifop, propaquizafop or quizalofop-P. As a further example, glufosinate may be used in enantiomerically enriched or enantiopure form, also known as glufosinate-P.

Those skilled in the art will recognize that any derivative of the above mentioned herbicides and/or safeners can be used in the practice of the invention, for example agriculturally suitable salts and esters.

Methods of Controlling Weeds

Herbicide-tolerant plants of the invention can be used in conjunction with an herbicide to which they are tolerant. Herbicides can be applied to the plants of the invention using any techniques known to those skilled in the art. Herbicides can be applied at any point in the plant cultivation process. For example, herbicides can be applied pre-planting, at planting, pre-emergence, post-emergence or combinations thereof. Herbicides may be applied to seeds and dried to form a layer on the seeds.

In some embodiments, seeds are treated with a safener, followed by a post-emergent application of a saflufenacil. In one embodiment, the post-emergent application of the saflufenacil is about 7 to 10 days following planting of safener-treated seeds. In some embodiments, the safener is cloquintocet, dichlormid, fluxofenim, or combinations thereof.

In other aspects, the present invention provides a method for controlling weeds at a locus for growth of a plant or plant part thereof, the method comprising: applying a composition comprising a saflufenacil to the locus.

In some aspects, the present invention provides a method for controlling weeds at a locus for growth of a plant, the method comprising: applying an herbicide composition comprising saflufenacil to the locus; wherein said locus is: (a) a locus that contains: a plant or a seed capable of producing said plant; or (b) a locus that is to be after said applying is made to contain the plant or the seed; wherein the plant or the seed comprises in at least some of its cells a recombinant polynucleotide operably linked to a promoter operable in plant cells, the promoter capable of expressing a cytochrome P450 polypeptide encoded by the polynucleotide, the expression of the polypeptide conferring to the plant tolerance to the saflufenacil.

Herbicide compositions hereof can be applied, e.g., as foliar treatments, soil treatments, seed treatments, or soil drenches. Application can be made, e.g., by spraying, dusting, broadcasting, or any other mode known useful in the art.

In one embodiment, herbicides can be used to control the growth of weeds that may be found growing in the vicinity of the herbicide-tolerant plants invention. In embodiments of this type, an herbicide can be applied to a plot in which herbicide-tolerant plants of the invention are growing in vicinity to weeds. An herbicide to which the herbicide-tolerant plant of the invention is tolerant can then be applied to the plot at a concentration sufficient to kill or inhibit the growth of the weed. Concentrations of herbicide sufficient to kill or inhibit the growth of weeds are known in the art and are disclosed above.

In other embodiments, the present invention provides a method for controlling weeds in the vicinity of a saflufenacil-tolerant plant of the invention. The method comprises applying an effective amount of a saflufenacil to the weeds and to the auxinic herbicide-tolerant plant, wherein the plant has increased tolerance to auxinic herbicide when compared to a wild-type plant. In some embodiments, the saflufenacil-tolerant plants of the invention are preferably crop plants, including, but not limited to, sunflower, alfalfa, *Brassica* sp., soybean, cotton, safflower, peanut, tobacco, tomato, potato, wheat, rice, maize, *sorghum*, barley, rye, millet, and *sorghum*.

In other aspects, herbicide(s) (e.g., saflufenacil) can also be used as a seed treatment. In some embodiments, an effective concentration or an effective amount of herbicide(s), or a composition comprising an effective concentration or an effective amount of herbicide(s) can be applied directly to the seeds prior to or during the sowing of the seeds. Seed Treatment formulations may additionally comprise binders and optionally colorants.

Binders can be added to improve the adhesion of the active materials on the seeds after treatment. In one embodiments, suitable binders are block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (Lupasol®, Polymin®), polyethers, polyurethans, polyvinylacetate, tylose and copolymers derived from these polymers. Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

The term seed treatment comprises all suitable seed treatment techniques known in the art, such as seed dressing, seed coating, seed dusting, seed soaking, and seed pelleting. In one embodiment, the present invention provides a method of treating soil by the application, in particular into the seed drill: either of a granular formulation containing the saflufenacil as a composition/formulation (e.g., a granular formulation), with optionally one or more solid or liquid, agriculturally acceptable carriers and/or optionally with one or more agriculturally acceptable surfactants. This method is advantageously employed, for example, in seedbeds of cereals, maize, cotton, and sunflower.

The present invention also comprises seeds coated with or containing with a seed treatment formulation comprising saflufenacil and at least one other herbicide such as, e.g., an AHAS-inhibitor selected from the group consisting of amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

In some embodiments, the seed treatment application with saflufenacil or with a formulation comprising the saflufenacil is carried out by spraying or dusting the seeds before sowing of the plants and before emergence of the plants.

In other embodiments, in the treatment of seeds, the corresponding formulations are applied by treating the seeds with an effective amount of saflufenacil or a formulation comprising the saflufenacil.

In other aspects, the present invention provides a method for combating undesired vegetation or controlling weeds comprising contacting the seeds of the saflufenacil-tolerant plants of the present invention before sowing and/or after pregermination with saflufenacil. The method can further comprise sowing the seeds, for example, in soil in a field or in a potting medium in greenhouse. The method finds particular use in combating undesired vegetation or controlling weeds in the immediate vicinity of the seed. The control of undesired vegetation is understood as the killing of weeds and/or otherwise retarding or inhibiting the normal growth of the weeds. Weeds, in the broadest sense, are understood as meaning all those plants which grow in locations where they are undesired.

The weeds of the present invention include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum.*

Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera.*

In addition, the weeds of the present invention can include, for example, crop plants that are growing in an undesired location. For example, a volunteer maize plant that is in a field that predominantly comprises soybean plants can be considered a weed, if the maize plant is undesired in the field of soybean plants.

In other embodiments, in the treatment of seeds, the corresponding formulations are applied by treating the seeds with an effective amount of saflufenacil or a formulation comprising the saflufenacil.

In still further aspects, treatment of loci, plants, plant parts, or seeds of the present invention comprises application of an agronomically acceptable composition that does not contain an A.I. In one embodiment, the treatment comprises application of an agronomically acceptable composition that does not contain a saflufenacil A.I. In some embodiments, the treatment comprises application of an agronomically acceptable composition that does not contain a saflufenacil A.I., wherein the composition comprises one or more of agronomically-acceptable carriers, diluents, excipients, plant growth regulators, and the like. In other embodiments, the treatment comprises application of an agronomically acceptable composition that does not contain a saflufenacil A.I., wherein the composition comprises an adjuvant. In one embodiment, the adjuvant is a surfactant, a spreader, a sticker, a penetrant, a drift-control agent, a crop oil, an emulsifier, a compatibility agent, or combinations thereof.

It will be readily apparent to one of ordinary skill in the relevant arts that other suitable modifications and adaptations to the methods and applications described herein are obvious and can be made without departing from the scope of the invention or any embodiment thereof. Having now described the present invention in detail, the same will be more clearly understood by reference to the following examples, which are included herewith for purposes of illustration only and are not intended to be limiting of the invention.

While the foregoing invention has been described in some detail for purposes of clarity and understanding, it will be appreciated by one skilled in the art from a reading of this disclosure that various changes in form and detail can be made without departing from the true scope of the invention and appended claims. All patents and publications cited herein are entirely incorporated herein by reference.

EXAMPLES

Example 1

Expression Analysis of Safener and Saflufenacil-Induced Monocot P450 Genes

Experiments were designed in rice, wheat, and maize to identify P450 genes induced by safener and/or saflufenacil application. Ten seeds were sown per 4 inch pot filled with Midwest soil and allowed to germinate for 4-5 days in standard greenhouse conditions. Once emergence from the soil was apparent, seedlings were sprayed according to the protocol shown in Table 4.

TABLE 4

Spray protocol for wheat, rice, and maize seedlings used for P450 expression analysis

| Sample | treatment | methylated seed oil adjuvant | Safener (500 g ai/ha) | saflufenacil (g ai/ha) |
|---|---|---|---|---|
| wheat | 1 | 0 | 0 | 0 |
|  | 2 | 0.1% v/v | 0 | 0 |
|  | 3 | 0.1% v/v | cloquintocet | 0 |
|  | 4 | 0.1% v/v | dichlormid | 0 |
|  | 5 | 0.1% v/v | 0 | 400 |
|  | 6 | 0.1% v/v | 0 | 800 |
|  | 7 | 0.1% v/v | cloquintocet | 400 |
|  | 8 | 0.1% v/v | cloquintocet | 800 |
|  | 9 | 0.1% v/v | dichlormid | 400 |
|  | 10 | 0.1% v/v | dichlormid | 800 |
| rice | 1 | 0 | 0 | 0 |
|  | 2 | 0.1% v/v | 0 | 0 |
|  | 3 | 0.1% v/v | cloquintocet | 0 |
|  | 4 | 0.1% v/v | dichlormid | 0 |
|  | 5 | 0.1% v/v | 0 | 400 |
|  | 6 | 0.1% v/v | 0 | 800 |
|  | 7 | 0.1% v/v | cloquintocet | 400 |
|  | 8 | 0.1% v/v | cloquintocet | 800 |
|  | 9 | 0.1% v/v | dichlormid | 400 |
|  | 10 | 0.1% v/v | dichlormid | 800 |
|  |  |  |  | corn |
| corn | 1 | 0 | 0 | 0 |
|  | 2 | 0.1% v/v | 0 | 0 |
|  | 3 | 0.1% v/v | dichlormid | 0 |
|  | 4 | 0.1% v/v | 0 | 400 |
|  | 5 | 0.1% v/v | 0 | 800 |
|  | 6 | 0.1% v/v | dichlormid | 400 |
|  | 7 | 0.1% v/v | dichlormid | 800 |

There were 7-10 independent treatments per experiment, each performed in duplicate. Twenty-four hours after treatment, all tissue above the seed coat was collected and flash frozen in liquid Nitrogen. Tissue was subsequently ground while frozen and RNA was isolated using a modified Centra Systems Versagene protocol. RNA was labeled and hybridized to wheat, rice, or maize gene chip arrays according to standard Affymetrix protocols. Data was RMA normalized, background subtracted, and quantile normalized.

Probesets corresponding to potential P450 genes were identified via sequence homology searches that compared the translated nucleotide sequence of the probeset to the amino acid sequences of known P450s in rice and *Arabidopsis* (blastx program). Sequences were considered potential P450s when the criteria were met of at least 50% identity within a length of at least 40 amino acids. A total of 349 wheat and 460 maize P450 target sequences were identified. Genedata Expressionist software was used to generate ANOVA tables with gene annotation. Differential expression tests were conducted using SAS9.1.

Figure 2B:
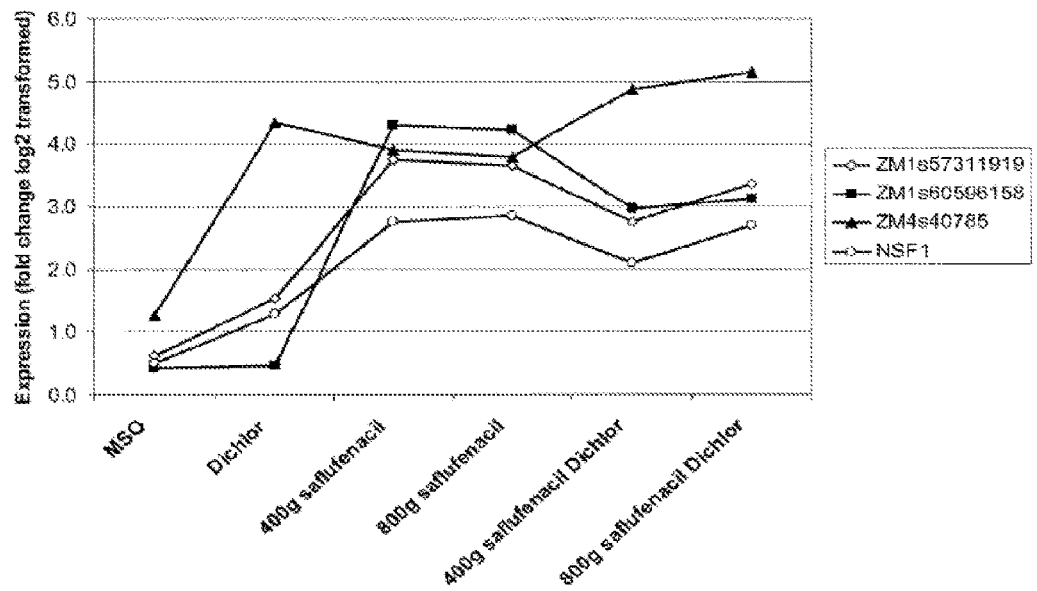
Figure 3:
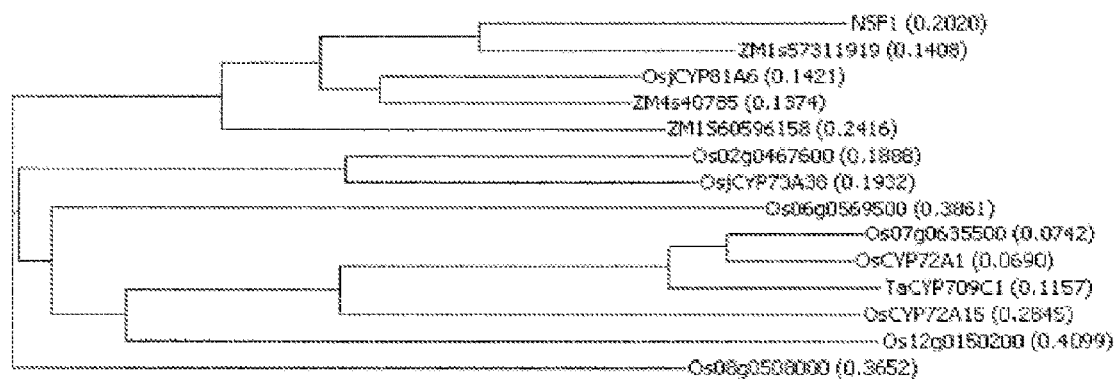
FIG. 3: Schematic guide tree. Sequences identified for testing in the maize, rice, and soybean transgenic systems were aligned and a guide tree prepared. Genes designated as OsCYP72A1, OsCYP72A15, NSF1 conferred tolerance to saflufenacil in one or more transgenic plant systems as disclosed herein. The guide tree was generated using the AlignX program, with the Neighbor Joining method (NJ) which works on a matrix of distances between all pairs of and these distances are related to the level of divergence between the sequences. The calculated distance values for each molecule are displayed in parenthesis.

For maize, 43 out of the 510 P450 probesets were differentially expressed at an FDR of <0.05 level. The probesets that were significantly differentially expressed and displayed a 4-10-fold induction upon treatment over unsprayed and/or adjuvant only controls were identified and targeted for subsequent cloning and transformation into various plant systems described below. Graphs indicating expression of the rice and maize P450 genes with the greatest fold induction are displayed in FIG. 2A and FIG. 2B. Based on these data, 9 rice genes and 4 maize genes were chosen for testing in rapid tolerance plant assays. Although several wheat transcripts were induced upon treatment, only one gene had known full-length sequence, TaCYP709C1. Its closest homolog in rice is OsjCYP72A1. For this reason, only this one gene from wheat was included in subsequent analyses. The amino acid sequences of the gene products identified in this screen were compared and a relational tree is indicated in FIG. 3. A pairwise table of the sequences disclosed herein as conferring tolerance to saflufenacil is also provided in Table 5.

Table 5 shows the alignment of P450 genes found to confer tolerance to saflufenacil as described in this document. Amino acid sequence identity is indicated as a percent of global alignment.

TABLE 5

Sequence identity table

|  | NSF1 | OsCYP72A15 | OsCYP73A38 | OsjCYP81A6 |
|---|---|---|---|---|
| NSF1 |  | 13 | 23 | 47 |
| OsCYP72A15 |  |  | 19 | 20 |
| OsCYP73A38 |  |  |  | 30 |
| OsjCYP81A6 |  |  |  |  |

The selected monocot P450 genes were cloned into monocot and dicot plant transformation vectors using standard cloning procedures. P450 expression was driven by the constitutive Maize Ubiquitin promoter for monocot expression and the constitutive Parsley Ubiquitin promoter for dicot expression.

Example 2

Maize immature embryos (ies: JHAX(HiIIXA188) were isolated from surface sterilized cobs (9-10 days post pollination) and cultured for 1 week on M-MS-101 media (Table 6).

TABLE 6

Maize media

| Ingredients | Supplier | M-MS-101 | M-LS-213 | M-LS-513 | M-LS-616 | M-MS-710 | R-N6-100 | M-LS-002 | M-LS-014 |
|---|---|---|---|---|---|---|---|---|---|
| MS Salts M-5524 | Phytotech | 4.3 g/L | 4.3 g/L | 4.3 g/L | 2.4 g/L | 4.3 g/L |  | 4.3 g/L | 4.3 g/L |
| N6 Salts | Duchefa |  |  |  |  |  | 3.96 g/L |  |  |
| N6 vitamins 1000x soln | Duchefa |  |  |  |  |  | 1x |  |  |
| Sucrose | VWR | 30 g/L | 20 g/L | 30 g/L | 20 g/l | 30 g/L |  | 68.5 g/L | 20 g/L |
| Glucose | VWR |  |  |  |  |  |  | 36 g/L | 10 g/L |
| Maltose | VWR |  |  |  |  |  | 30 g/L |  |  |
| Casamino Acid | BD |  |  |  |  |  | 300 mg/L | 1 g/L |  |
| Nicotinic acid | Sigma |  | 0.5 mg/L | 0.5 mg/L | 0.5 mg/L | 0.5 mg/L |  | 0.5 mg/L | 0.5 mg/L |
| Pyridoxine HCl | Sigma |  | 0.5 mg/L | 0.5 mg/L | 0.5 mg/L | 0.5 mg/L |  | 0.5 mg/L | 0.5 mg/L |
| Thiamine HCl | Sigma |  | 1 mg/L | 1 mg/L | 1 mg/L | 1 mg/L |  | 1 m/L | 1 m/L |

TABLE 6-continued

Maize media

| Ingredients | Supplier | M-MS-101 | M-LS-213 | M-LS-513 | M-LS-616 | M-MS-710 | R-N6-100 | M-LS-002 | M-LS-014 |
|---|---|---|---|---|---|---|---|---|---|
| Myo-inositol | Sigma | | 100 mg/L | 100 mg/L | 100 mg/L | 100 mg/L | | 100 mg/L | 100 mg/L |
| L-Proline | Sigma | 2.9 g/L | 700 gm/L | 700 gm/L | | 1.16 g/L | 2.9 g/L | | 700 gm/L |
| MPS | Sigma | | 500 mg/L | 500 mg/L | 500 mg/L | 500 mg/L | 500 mg/L | | 500 mg/L |
| Casein hydrolysate | Sigma | 100 mg/L | | | | 1 g/L | | | |
| L-Asparagine monohydrate | Sigma | | | | | 150 mg/L | | | |
| -->pH | | 5.8 | 5.8 | 5.8 | 5.8 | 5.7 | 5.8 | 5.2 | 5.8 |
| Gelrite | Duchefa | 2.0 g/L | | | 2.0 g/L | | | | |
| Purified Agar | Sigma | | 8.0 g/L | 8.0 g/L | | 8.0 g/L | | | 10 g/L |
| -->Autoclave (min) | | 20 | 20 | 20 | 20 | 20 | 20 | | 20 |
| 2 4-D | Sigma | 1.5 mg/L | 0.5 mg/L | | | 1 mg/L | 2 mg/L | 1.5 | 1.0 mg/L |
| MS Vitamins | Sigma | 1.0 mg/mL | | | | | | | |
| Silver Nitrate | VWR | 15 μM | | | | | | | 15 μM |
| Timentin | Bellamy DS | 150 mg/L | | | | | | | |
| Picloram | Sigma | | 2 mg/L | | | | | | |
| Kinetin | Sigma | | | 0.5 mg/L | | | | | |
| Acetosyringone | Aldrich | | | | | | | 200 μM | 200 μM |

Embryos with embryogenic callus were randomly distributed to 0, 50, 100, 250, 500, 750 or 1000 nM saflufenacil containing media (Modified M-LS-213: Table 6). Response was rated as stated above. Two plates were utilized/level/condition and 10 calli/plate. Growing callus was further transferred to regeneration media (modified M-LS513: Table 6) with the above levels of saflufenacil. Following shoot formation, growing shoots were transferred to rooting boxes containing M-LS-616 (Table 6) with the above mentioned saflufenacil concentrations and additional concentrations of 2 and 3 μM.

Example 3

Maize Immature Embryo Transformation and Response to Herbicide

Immature Embryo Transformation: Immature embryos were transformed according to the procedure outlined in WO2006/136596 to Peng et al. The exception was that a proportion of the embryos—25 in most cases—were placed on media containing saflufenacil and kept in the light for direct selection. The remaining embryos in each experiment were selected on Pursuit as described. Plants were tested utilizing Taqman analysis with the target being the nos terminator which is present in all constructs. Healthy looking plants were sent to the greenhouse for hardening out and subsequent spray testing. As with the BMS cells, RCB958 was utilized as a control both for transformation, saflufenacil selection, and for spray testing.

A total of 82 transgenic maize plants (2 constructs of interest and 1 control construct) were delivered to the greenhouse in tissue culture. The plants were individually transplanted into MetroMix 360 soil in 4" pots. Once they had been in the greenhouse (day/night cycle of 27° C./21° C. with 14 hour day length supported by 600 W high pressure sodium lights), they were allowed to grow for 14 days. They were then sprayed with a treatment of [200 g ai/ha] saflufenacil+1.0% v/v MSO. Herbicide injury evaluations were taken both 2 and 7 days Postspray to look for injury to new growth points and overall plant health. The top survivors were transplanted into gallon pots filled with MetroMix 360 for seed production.

Figure 4:
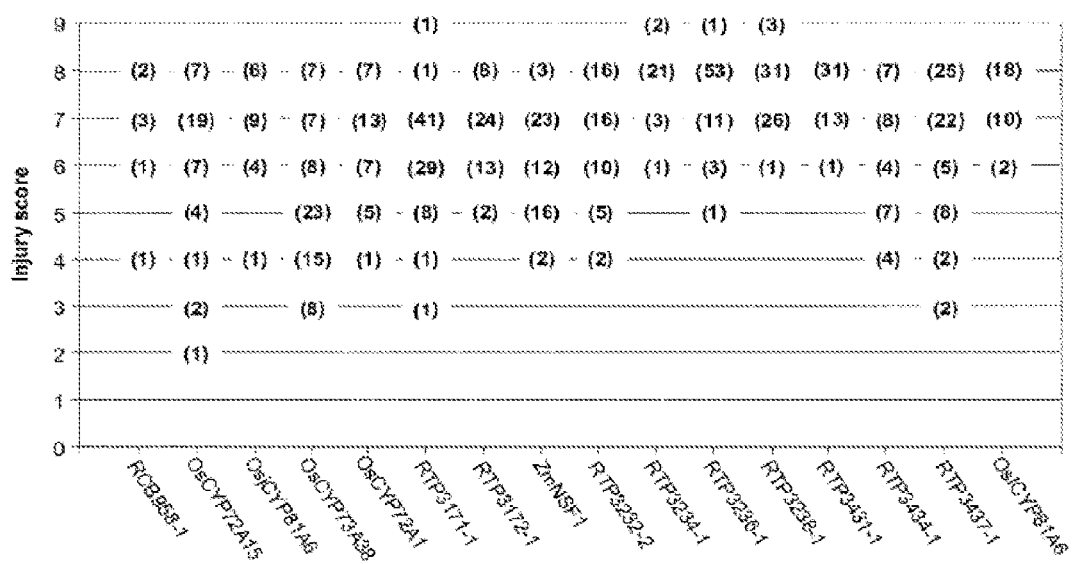
FIG. 4: Herbicide injury scores for independent TO maize events treated with 200 g ai/ha saflufenacil+1% MSO. Numbers indicate number of events that fell within a particular injury score. Injury scores are from 0-9, 0 being no injury and 9 being death. Untransformed J553 is the control.

T0 transgenic plants representing independent events indicated in FIG. 4 were transplanted to the greenhouse and sprayed as indicated in the methods section. At just two days postspray most plants showed severe damage to their growth points, and major stress damage to leaf tissue where the herbicide made contact. However, several independent transgenic events expressing OsCYP72A15, OsjCYP81A6, and OsCYP73A38 showed increased tolerance as indicated by injury scores of 2 and 3.

Example 4

Soybean Transformation and Root Response to Herbicide

Soybean cv William 82 was used in all these experiments. Seeds were sterilized and germinated in seed germination medium for 7 d as described by Hong et al., In Vitro Cell. Dev. Biol. Plant 2007:43:558-568 (2007). Epicotyls were completely removed from the seedlings, and hypocotyls 0.5 to 1 cm below the cot-node were cut. The cut surface of the hypocotyls was the target for *Agrobacterium* infection and root regeneration. Disarmed *Agrobacterium rhizogenes* SHA17 (Mankin et al., In Vitro Cell. Dev. Biol. Plant, 43: 521-535 (2007)) harboring all the binary vectors such as RTP3137 was cultured on YEP growth medium containing 50 mg/L kanamycin for 2-4 d. Hypocotyl cut ends prepared as above were dipped onto the *Agrobacterium* cells on YEP plates, and then placed on 1% agar plate (100×25 mm). Plates were sealed with parafilm or 3MM tape. The hypocotyl explants were co-cultured with *Agrobacterium* for 7 to 10 d under light. After 7 to 10 d co-cultivation, hypocotyl explants were transferred to root induction medium with arsenal (imazapyr) selection (root induction medium contained ½ MS salts and ½ B5 vitamins, 20 g/l sucrose, 7 g/l purified agar, 1 mg/l naphthaleneacetic acid (NAA), 400 mg/l timentin and 1 μM arsenal). After 3 d for root induction medium, hypocotyls were transferred to root growth medium without growth regulators containing ⅕ MS salts and ⅕ B5 vitamins, 20 g/l sucrose, 400 mg/l timemtin, 1 μM arsenal and 7 g/l gelrite for root elongation. Elongated roots were usually obtained after 12 to 20 d on this media.

Saflufenacil kill curves were determined in a preliminary experiment by culturing Agrobacterium infected hypocotyl explants on media supplemented with various amount of saflufenacil (0, 25, 50, 75, 200, 400, 600, 800, 1000 nM). In this experiment, SHA17 containing a control construct was used. Saflufenacil at 400 nM was chosen as the optimal concentration to test for tolerance.

Root Growth Assay:

Hypocotyl explant containing transgenic roots (cultured on root growth medium for 10 to 12 d) were transferred to saflufenacil-containing medium (⅕ MS salts and ⅕ B5 vitamins, 20 g/L sucrose, 200 mg/L timemtin, 7 g/L gelrite and 400 nM saflufenacil). The roots were pushed into the medium. After 2 to 3 week culture, the root growth was recorded and data were collected using the construct with AHAS II only as the control. If the roots further elongated and produced secondary roots, and root tips remained white or creamy yellow, the roots were considered as tolerant to saflufenacil.

Root Penetration Assay:

Hypocotyl explant containing transgenic roots (cultured on root growth media for 20 d) were transferred to the same medium as above, but the roots were placed on the surface of the medium, instead of inside of the medium. Roots which penetrated into the media with white root tips and elongated for to minimum 0.5 cm in length were considered as tolerant to saflufenacil.

To date 18 constructs containing various P450 GOIs were assayed using the two methods as described above, roots containing construct RTP3173 (GOI: ZmNSF1) showed tolerance to saflufenacil based on both root growth and root penetration ability. Roots containing construct RTP 3155 (GOI: OsjCYP72A1) showed slight tolerance compared to the control (Table 7).

TABLE 7

Summary of saflufenacil tolerance experiments using soy TRAP roots

| Constructs | Explants | Explants with strong roots | Strong root penetrated to media number | Tolerance rate |
|---|---|---|---|---|
| Experiment 1 | | | | |
| NH4-5 (ck) | 15 | 0 | 0 | 0 |
| RTP3173 | 15 | 4 | 3 | +++ |
| RTP3034 | 15 | 1 | 0 | 0 |
| RTP3155 | 15 | 3 | 1 | + |
| RTP3435 | 15 | 0 | 0 | 0 |
| RTP3432 | 15 | 0 | 0 | 0 |
| Experiment 2 | | | | |
| NH4-5 | 20 | 0 | 0 | 0 |
| RTP3237 | 20 | 0 | 0 | 0 |
| RTP3235 | 20 | 0 | 0 | 0 |
| RTP3233 | 20 | 0 | 0 | 0 |
| RTP3157 | 20 | 0 | 0 | 0 |
| RTP2681 | 20 | 0 | 0 | 0 |
| Experiment 3 | | | | |
| NH4-5 | 30 | 0 | 0 | 0 |
| RTP3155 | 30 | 2 | 0 | + |
| RTP3173 | 30 | 6 | 5 | +++ |
| RTP2549 | 30 | 0 | 0 | 0 |
| Experiment 4 | | | | |
| NH4-5 | 30 | 0 | 0 | 0 |
| RTP3036 | 30 | 0 | 0 | 0 |
| RTP3239 | 30 | 0 | 0 | 0 |
| RTP3438 | 30 | 0 | 0 | 0 |
| RTP3035 | 30 | 0 | 0 | 0 |

The association of vector names and expression cassettes are shown in Table 8.

TABLE 8

Association of vector names and P450 expression cassettes

| Vector name | Promoter | P450 GO I |
|---|---|---|
| RTP3034 | p-PcUBI4-2 | OsjCYP72A15 |
| RTP3035 | p-PcUBI4-2 | OsjCYP81A6 |
| RTP3036 | n-PcUBI4-2 | OsjCYP73A38 |
| RTP3155 | p-PcUBI4-2 | OsjCYP72A1 |
| RTP3156 | n-PcUBI4-2 | TaCYP709C1 |
| RTP3157 | p-PcUB14-2 | Osj07g0635500 |
| RTP3167 | n-ZmUB1+1 | OsjCYP72A15 |
| RTP3168 | n-ZmUB1+1 | OsjCYP81A6 |
| RTP3169 | p-ZmUB1+1 | OsjCYP73A38 |
| RTP3170 | p-ZmUBI+1 | OsjCYP72A1 |
| RTP3171 | p-ZmUB1+1 | TaCYP709C1 |
| RTP3172 | p-ZmUBI+I | Osj07g0635500 |
| RTP3173 | p-PcUBI4-2 | ZmNSF1 |
| RTP3174 | p-ZmUBI+I | ZmNSF1 |
| RTP3232 | p-ZmUBI+I | 0s02g0467600 |
| RTP3233 | p-PcUBI4-2 | 0s02g0467600 |
| RTP3234 | p-ZmUB1+1 | 0s06g0569500 |
| RTP3235 | p-PcUB14-2 | 0s06g0569500 |
| RTP3236 | p-ZmUBI+I | 0s08g0508000 |
| RTP3237 | p-PcUBI4-2 | 0s08g0508000 |
| RTP3238 | p-ZmUB1+1 | 0s12g0150200 |
| RTP3239 | p-PcUBI4-2 | 0s12g0150200 |
| RTP3431 | p-ZmUBI+I | ZM1s60596158 |
| RTP3432 | p-PcUBI4-2 | ZM1s60596158 |
| RTP3434 | p-ZmUBI+I | ZM4s40785 |
| RTP3435 | p-PcUBI4-2 | ZM4s40785 |
| RTP3437 | p-ZmUBI+I | ZM1s57311919 |
| RTP3438 | p-PcUBI4-2 | ZM1s57311919 |
| RTP3545 | p-ZmUBI+I | OsICYP81A6 |
| RTP3546 | p-PcUBI4-2 | OsICYP81A6 |

None of the other 16 constructs exhibited tolerance in this bioassay using this transgenic soy root assay.

REFERENCES

Didierjean et al., Plant Physiol. 130:179-189 (2002).
Siminszky et al., Phytochem. Rev. 5:445-458 (2006).
Nelson et al., Phytochem. Rev. 5:193-204 (2006).
Williams et al., "Map-based cloning of the nsfl gene of maize," In: Program and Abstracts of the 48th Maize Genetic Conference, Pacific Grove, Calif., USA (2006).
WO 2007/103567 to Dam et al.
Riechers et al., Personal communication: Biochemical mechanisms for tolerance to BAS-800H in corn and soybeans. BASF AP Kixor™ Metabolism meeting, RTP NC USA (2008).
Bell et al., Biochem. Soc. Trans. 31:558-562 (2003).
Abecassis et al., Biocatal. Biotrans. 21:55-66 (2003).
Siminszky et al., Pestic. Biochem. Physiol. 77:35-43 (2003).
Hiei and Komari, Nat Protoc. 3: 824-34 (2008).
WO2006/136596 to Peng et al.

Example 6

CYP450 Amino Acid and Nucleic Acid Sequences

Examples of CYP450 amino acid sequences are set forth in SEQ ID NO:29 (OsICYP81A6), SEQ ID NO:32 (Sb01g007420.1), SEQ ID NO:34 (Rice: Q94HA3_ORYSJ), SEQ ID NO:35 (Rice: A2XM72_ORYSI), SEQ ID NO:36 (Rice: Q94HA4_ORYSJ), SEQ ID NO:37 (Rice: B9F5T6_ORYSJ), SEQ ID NO:38 (Rice:

Q94HA6_ORYSJ), SEQ ID NO:39 (Sorghum: C5X058_Sb01g007400), SEQ ID NO:40 (Sorghum: C5X059 Sb01g007410), SEQ ID NO:41 (Sorghum: C5X060 Sb01g007420), SEQ ID NO: 42 (Sorghum: C5X061 Sb01g007430), SEQ ID NO:43 (Maize: B6SYC0_ZM_CYP81A3v2), SEQ ID NO:44 (Maize: B6SSF2_ZM_CYP81A16), SEQ ID NO:45 (Brachypodium distachyon: Bradi_1g07930.1) and SEQ ID NO:46 (Brachypodium distachyon: Bradi_1g14900.1). Examples of CYP450 nucleic acid sequences are set forth in SEQ ID NO:28 (OsICYP81A6), SEQ ID NO:30 (OsyCYP81A6), SEQ ID NO:31 (Sb01g007420.1, optimized for yeast expression), SEQ ID NO:33 (OsCYP73A38)

Example 7

Saflufenacil Spray Tests

Maize Whole Plant Transformation and Saflufenacil Tolerance Testing:

Immature embryos were transformed according to the procedure outlined in Peng et al. supra. Plants were tested for the presence of the T-DNA by Taqman analysis with the target being the nos terminator which is present in all constructs. Healthy looking plants were sent to the greenhouse for hardening out and subsequent spray testing.

The plants were individually transplanted into MetroMix 360 soil in 4" pots. Once they had been in the greenhouse (day/night cycle of 27° C./21° C. with 14 hour day length supported by 600 W high pressure sodium lights), they were allowed to grow for 14 days. They were then sprayed with a treatment of [200 g ai/ha] saflufenacil+1.0% v/v methylated seed oil (MSO). Herbicide injury evaluations were taken both 2 and 7 days Postspray to look for injury to new growth points and overall plant health. The top survivors were transplanted into gallon pots filled with MetroMix 360 for seed production.

Soybean Transformation and Saflufenacil Tolerance Testing:

Soybean cv Williams 82 was transformed as previously described by Siminszky et al., Phytochem Rev. 5:445-458 (2006). After regeneration, transformants were transplanted to soil in small pots, placed in growth chambers (16 hr day/8 hr night; 25° C. day/23° C. night; 65% relative humidity; 130-150 µE m$^{-2}$ s$^{-1}$) and subsequently tested for the presence of the T-DNA via Taqman analysis. After a few weeks, healthy, transgenic positive, single copy events were transplanted to larger pots and allowed to grow in the growth chamber. An optimal shoot for cutting was about 3-4" tall, with at least two nodes present. Each cutting was taken from the original transformant (mother plant) and dipped into rooting hormone powder (indole-3-butyric acid, IBA). The cutting was then placed in oasis wedges inside a bio-dome. The mother plant was taken to maturity in the greenhouse and harvested for seed. Wild type cuttings were also taken simultaneously to serve as negative controls. The cuttings were kept in the bio-dome for 5-7 days and then transplanted to 3" pots and then acclimated in the growth chamber for two more days. Subsequently, the cuttings were transferred to the greenhouse, acclimated for approximately 4 days, and then subjected to spray tests containing 0, 25, and 50 g ai/ha saflufenacil plus 1% MSO. Herbicide injury evaluations were taken at 7 days after treatment.

Yeast Expression System and Analysis of Saflufenacil Metabolism:

Rice cytochrome P450 81A6 was cloned into pESC-His yeast expression vector (Stratagene) using BamHI and SalI. Constructs were transformed into YPH500 yeast strain (Stratagene) using a Yeast Maker Transformation System from Clontech. Positive clones were selected on SD-agar plates (0.7% yeast nitrogen base without amino acids, 2% glucose, 0.13% amino acid drop-out without histidine; plates solidified with 2% agar). Bioconversion of substrates was directly assayed in yeast cells expressing the respective cytochrome P450 gene. Cells were induced in SG-His medium (same composition as SD but with galactose instead of glucose) for 18-24 h (Pompon et al., Methods in Enzymology 272:51-64 (1996); Urban et al., Eur. J. Biochem. 222:853-850 (1994)). Afterwards, the BAS800H substrate was added and samples were incubated for an additional 24 h. Samples were analyzed by LC/MS/MS.

The association of vector names and the genes expressed therefrom is shown in Table 9.

TABLE 9

| Association of vector names and the genes expressed therefrom | | | |
|---|---|---|---|
| gene | corn vector | soy vector | yeast vector |
| NSF1 | RTP3174 | RTP3173 | RTP5743 |
| OsICYP81A6 | RTP3545 | RTP3546 | RTP5737 |
| sorghum 81A6 | | | RTP5789 |
| OsCYP72A1 | RTP3170 | RTP3155 | RTP5745 |
| OsjCYP81A6 | RTP3168 | RTP3035 | None |

Figure 5:
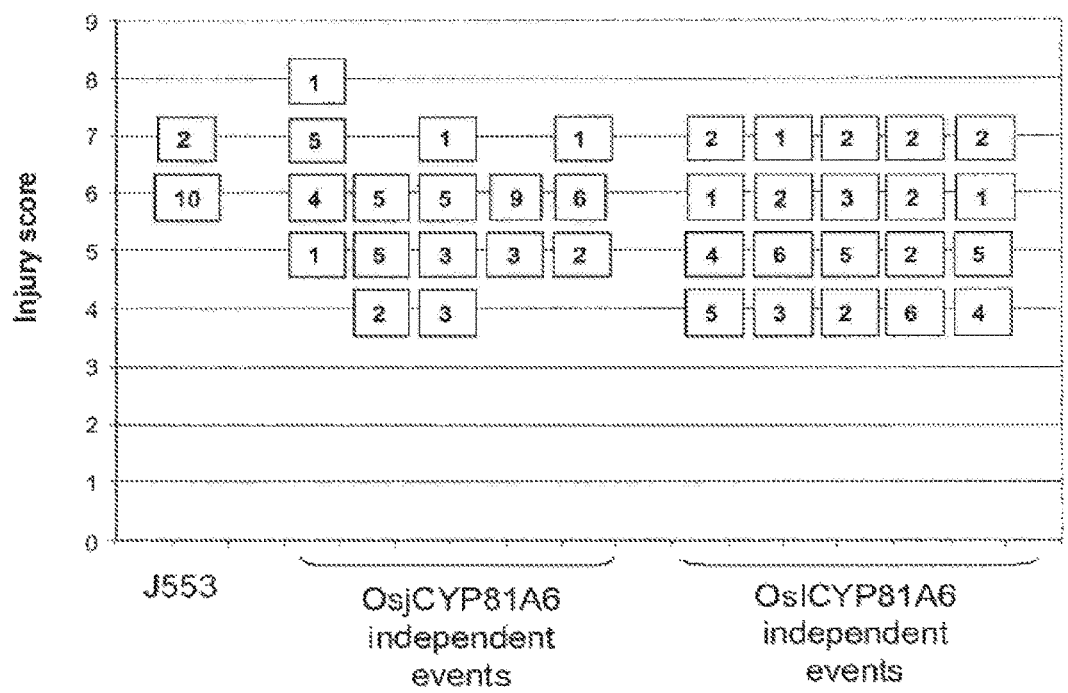
FIG. 5: Herbicide injury scores for segregating independent T1 maize events treated with 240 g ai/ha Kixor+1% MSO. Numbers indicate the number of plants that fell within a particular injury score. Injury scores are from 0-9, 0 being no injury and 9 being death. Untransformed J553 is the control.

Maize Whole Plant Transformation and Saflufenacil Tolerance Testing:

Sixteen vectors harboring different P450 genes were tested for the ability to increase tolerance to saflufenacil in T0 maize plants. FIG. 4 indicates the injury scores of those transfon-nants treated with 200 g ai/ha saflufenacil+1% MSO. OsCYP72A15 and OsCYP73A38 performed the best in maize with several events having injury scores of 3 or less. T1 seed was harvested from selected tolerant TO plants and replanted and sprayed with 240 g ai/ha saflufenacil+1% MSO at the 2-4 leaf stage (2 weeks post-sowing). Injury rating was evaluated 7 and 14 days after application. FIG. 5 indicates the number of plants from each segregating event that were evaluated and scored for herbicidal injury. OsjCYP81A6 and OsICYP81 A both conferred increased tolerance to the maize plants as indicated by the reduced injury scores as compared to the J553 wild type germplasm alone.

Figure 6:
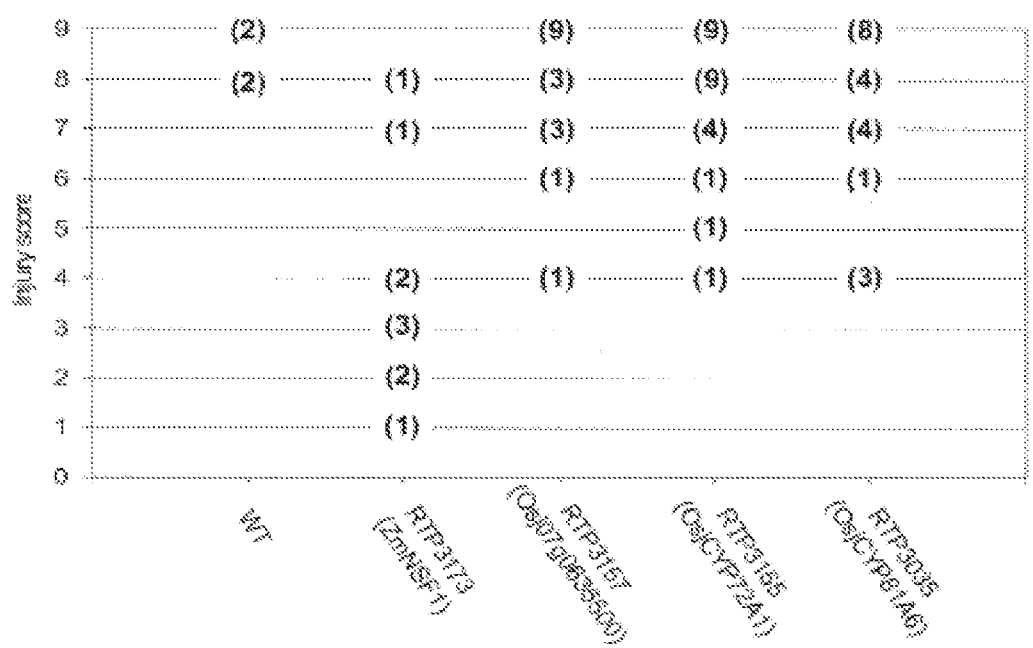
FIG. 6: Herbicide injury scores for cuttings of independent TO transgenic and wild type (cultivar Williams82) soybean events treated with 25 g ai/ha saflufenacil+1% MSO. Numbers indicate number of events that fell within a particular injury score. Injury scores are from 0-9, 0 being no injury and 9 being death.
Figure 7A:
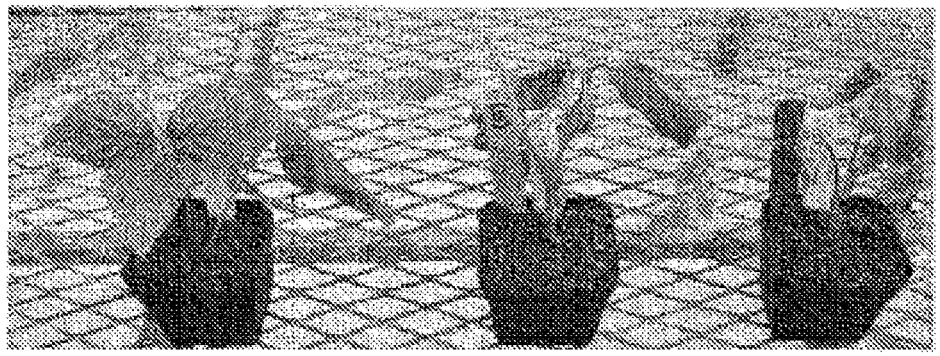
FIGS. 7A and 7B: Herbicide injury of cuttings from T0 wild-type (FIG. 7A) and vector-transformed (FIG. 7B) soybean events treated as indicated. Application rate of saflufenacil is indicated.
Figure 7B:
Figure 8:
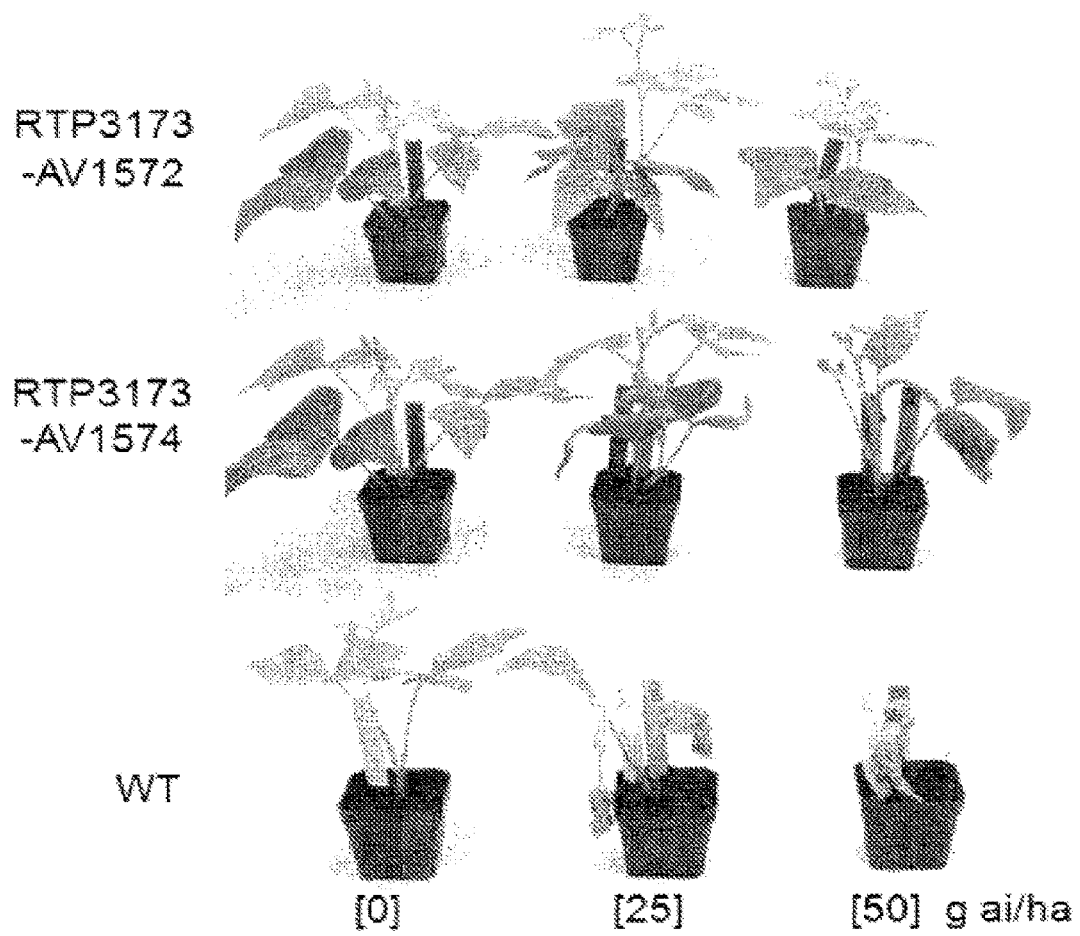
FIG. 8: Saflufenacil tolerance spray test of T0 soybean cuttings from RTP3173 (ZmNSF1) transfon-nants. Saflufenacil spray rates are indicated below the plants as g ai/ha.

Soybean Transformation and Saflufenacil Tolerance Testing:

Four vectors harboring different monocot P450s genes were tested for the ability to confer tolerance to saflufenacil in TO soybean cuttings. FIGS. 6-8 indicate the level of injury of those plants treated with 0, 25, or 50 g ai/ha saflufenacil+1% MSO. In these assays, ZmNSF1 and OsjCYP81A6 conferred the greatest level of tolerance.

Yeast Expression System and Analysis of Saflufenacil Metabolism:

OsICYP81A6 and Sb01g007420.1 catalyzed degradation of BAS800H. After 24 h incubation, 10% of the initial content of BAS800H was converted into several metabolites with majority (5%) being found as the inactive BAS800H02.

What is claimed is:

1. A cell of a crop plant comprising a recombinant polynucleotide encoding a cytochrome P450 polypeptide, wherein the polynucleotide is codon-optimized for the crop plant, wherein the polypeptide comprises the amino acid sequence of SEQ ID NO: 45, and wherein the crop plant is soybean.

2. A crop plant or a crop plant part comprising a recombinant polynucleotide encoding a cytochrome P450 polypeptide, wherein the polynucleotide is codon-optimized for the crop plant, wherein the polypeptide comprises the amino acid sequence of SEQ ID NO: 45, and wherein the crop plant is soybean.

* * * * *

SEQUENCE LISTING

<160> NUMBER OF SEQ ID NOS: 46

<210> SEQ ID NO 1
<211> LENGTH: 732
<212> TYPE: PRT
<213> ORGANISM: Oryza sativa

<400> SEQUENCE: 1

```
Met Ala Phe Leu Gly Trp Ala Val Asp Ile Ala Arg Asp Ser Gly Ala
1               5                   10                  15

Ser Ser Ser Val Val Leu Thr Cys Asp Gly Tyr Gly Ser Ala Leu Tyr
            20                  25                  30

Phe Ser Pro Trp Asp Ser Val Pro Leu Pro Ala Thr Ala Ser Pro Asp
        35                  40                  45

Asp Gly Phe Leu Leu Pro Arg Phe Pro Asp Val Cys Val Gln Arg Ser
    50                  55                  60

Gln Phe Thr Asn His Leu Ala Pro Ala Asn Gly Thr Gly Gly Gly Gly
65                  70                  75                  80

Ser Arg Thr Gly Val Lys Glu Glu Ala Ser Glu Val Leu Ser Trp Pro
                85                  90                  95

Pro Thr Ser Lys Gln Ser Val Arg Arg Leu Glu Val Ala Glu His Trp
            100                 105                 110

Tyr Arg Leu Tyr Lys Thr Asp Asn Gln Arg Leu Ser Pro Asp Ser Gln
        115                 120                 125

Gln Val Ser Val Leu Ala Glu Ser His Cys Asp Leu Ala Ser Gly Asn
    130                 135                 140

Trp Lys Glu Ile Ser Ile His His Lys Lys Met Pro Ser Ser Thr Thr
145                 150                 155                 160

Thr Lys Thr Thr Thr Pro Ser Arg Asp Ala Trp Ile Val Ser Ala Arg
                165                 170                 175

Ser Asp Pro Phe His Leu Leu Leu Glu Ala Gln Ala Pro Leu Gly Ile
            180                 185                 190

Lys Ala Asp Ala Leu Ser Gln Ile Ala Ala Val His Gln Ser His Arg
        195                 200                 205

Asn Thr Ser His Ile Arg Glu Leu Ser Leu Ala Met Asp Asn Ala Tyr
    210                 215                 220

Ile Ile Ala Ile Leu Ser Val Ala Ile Leu Phe Leu Leu His Tyr Tyr
225                 230                 235                 240

Leu Leu Gly Arg Gly Asn Gly Gly Ala Ala Arg Leu Pro Pro Gly Pro
                245                 250                 255

Pro Ala Val Pro Ile Leu Gly His Leu His Leu Val Lys Lys Pro Met
            260                 265                 270

His Ala Thr Met Ser Arg Leu Ala Glu Arg Tyr Gly Pro Val Phe Ser
        275                 280                 285

Leu Arg Leu Gly Ser Arg Arg Ala Val Val Ser Ser Pro Gly Cys
    290                 295                 300

Ala Arg Glu Cys Phe Thr Glu His Asp Val Thr Phe Ala Asn Arg Pro
305                 310                 315                 320

Arg Phe Glu Ser Gln Leu Leu Val Ser Phe Asn Gly Ala Ala Leu Ala
                325                 330                 335

Thr Ala Ser Tyr Gly Ala His Trp Arg Asn Leu Arg Arg Ile Val Ala
            340                 345                 350

Val Gln Leu Leu Ser Ala His Arg Val Gly Leu Met Ser Gly Leu Ile
        355                 360                 365
```

Ala Gly Glu Val Arg Ala Met Val Arg Arg Met Tyr Arg Ala Ala
    370                 375                 380

Ala Ser Pro Ala Gly Ala Ala Arg Ile Gln Leu Lys Arg Arg Leu Phe
385                 390                 395                 400

Glu Val Ser Leu Ser Val Leu Met Glu Thr Ile Ala His Thr Lys Ala
                405                 410                 415

Thr Arg Pro Glu Thr Asp Pro Asp Thr Asp Met Ser Val Glu Ala Gln
            420                 425                 430

Glu Phe Lys Gln Val Val Asp Glu Ile Ile Pro His Ile Gly Ala Ala
        435                 440                 445

Asn Leu Trp Asp Tyr Leu Pro Ala Leu Arg Trp Phe Asp Val Phe Gly
    450                 455                 460

Val Arg Arg Lys Ile Leu Ala Ala Val Ser Arg Arg Asp Ala Phe Leu
465                 470                 475                 480

Arg Arg Leu Ile Asp Ala Glu Arg Arg Leu Asp Asp Gly Asp Glu
                485                 490                 495

Gly Glu Lys Lys Ser Met Ile Ala Val Leu Leu Thr Leu Gln Lys Thr
            500                 505                 510

Glu Pro Glu Val Tyr Thr Asp Asn Met Ile Thr Ala Leu Thr Ala Asn
        515                 520                 525

Leu Phe Gly Ala Gly Thr Glu Thr Thr Ser Thr Thr Ser Glu Trp Ala
    530                 535                 540

Met Ser Leu Leu Leu Asn His Pro Asp Thr Leu Lys Lys Ala Gln Ala
545                 550                 555                 560

Glu Ile Asp Ala Ser Val Gly Asn Ser Arg Leu Ile Thr Ala Asp Asp
                565                 570                 575

Val Thr Arg Leu Gly Tyr Leu Gln Cys Ile Val Arg Glu Thr Leu Arg
            580                 585                 590

Leu Tyr Pro Ala Ala Pro Met Leu Leu Pro His Glu Ser Ser Ala Asp
        595                 600                 605

Cys Lys Val Gly Gly Tyr Asn Ile Pro Arg Gly Ser Met Leu Leu Ile
    610                 615                 620

Asn Ala Tyr Ala Ile His Arg Asp Pro Ala Val Trp Glu Glu Pro Glu
625                 630                 635                 640

Lys Phe Met Pro Glu Arg Phe Glu Asp Gly Cys Asp Gly Asn Leu
                645                 650                 655

Leu Met Pro Phe Gly Met Gly Arg Arg Cys Pro Gly Glu Thr Leu
            660                 665                 670

Ala Leu Arg Thr Val Gly Leu Val Leu Gly Thr Leu Ile Gln Cys Phe
        675                 680                 685

Asp Trp Glu Arg Val Asp Gly Val Glu Val Asp Met Thr Glu Gly Gly
    690                 695                 700

Gly Leu Thr Ile Pro Lys Val Val Pro Leu Glu Ala Met Cys Arg Pro
705                 710                 715                 720

Arg Asp Ala Met Gly Gly Val Leu Arg Glu Leu Val
                725                 730

<210> SEQ ID NO 2
<211> LENGTH: 2199
<212> TYPE: DNA
<213> ORGANISM: Oryza sativa

<400> SEQUENCE: 2

```
atggcgttct tgggatgggc ggtcgacatc gcccgcgact ccggcgcgtc gagctccgtc    60
gtgctcacct gcgacggcta cggctcggcg ctctacttct cgccgtggga cagtgtcccg   120
cttccggcga cagcttcccc cgacgacggc ttcctgctgc cgcgtttccc ggacgtctgc   180
gtgcagcgct cgcaattcac caaccacctc gcgccggcca acggcactgg cggcggcggc   240
tcaagaacgg gcgtcaagga ggaagcgagc gaggtgttgt cctggccacc gacttcgaag   300
caatctgtgc gccggttgga ggtggcggag cactggtacc gactctacaa gacggacaat   360
caacggctgt ctcctgatag tcaacaggtc tcggtcctcg cagagtcgca ctgcgatttg   420
gcctctggaa actggaaaga gatctcgatc caccacaaga aaatgccaag cagcacgacg   480
acgaagacga caacgccttc cagagatgcc tggattgtct ccgcaagatc tgatccattt   540
catctccttc tagaagcaca agcgccgctc ggtataaagg cagacgcatt gtcacaaata   600
gctgcagtgc accagagtca cagaaacaca tcacacattc gtgagctcag cttagccatg   660
gataacgcct acattattgc cattctctct gtagctatcc tcttcttgct ccactactac   720
ctcctcggcc gcggcaatgg cggggcggcg cggctgccgc cgggtccacc ggccgtcccg   780
atcctgggac acctccacct cgtcaagaag ccgatgcacg ccaccatgtc ccgcctcgcc   840
gagcggtacg ggccggtgtt ctcgctgcgc ctcgggtcgc ggcgtgccgt ggtggtgtcg   900
tcgccggggt gcgccaggga gtgcttcacc gagcacgacg tgaccttcgc gaaccggccc   960
aggttcgagt cgcagctgct ggtctcgttc aacggcgccg cgctcgccac ggcgagctac  1020
ggcgcgcact ggcgcaacct ccgccggatc gtcgccgtgc agctgctctc cgcgcaccgc  1080
gtcggcctca tgtcggggct catcgccggc gaggtccgcg ccatggtgcg gaggatgtac  1140
cgcgccgcgg ccgcgtcccc cgccggcgcc gcgcgcatcc agctgaagcg gaggctgttc  1200
gaggtctccc tcagcgtgct catggagacc atcgcccaca ccaaggcgac ccgccccgag  1260
acggacccgg acaccgacat gtccgtggaa gcccaggagt ttaagcaggt cgtcgacgag  1320
atcatcccgc acatcggcgc ggccaacctg tgggactact tgccggcgct ccggtggttc  1380
gacgtgttcg gcgtcaggag gaagatcctc gccgctgtaa gccggaggga cgcgttcctt  1440
cgccgcctga tcgacgcgga gcggcggagg ctggacgacg cgacgagggg cgagaagaag  1500
agcatgatcg ccgtgctgct cactctgcag aagacagagc cggaggtgta caccgataac  1560
atgatcacag ctctaacggc gaacttgttc ggagcaggaa cagagacaac ctcgacgaca  1620
tcagaatggg cgatgtcgct actgctgaac caccccgaca cactcaagaa agcgcaagcc  1680
gagatcgacg catccgtcgg caactctcgc ctgatcaccg ccgacgacgt gactcgcctc  1740
ggctacctcc agtgcatcgt cagggagacg ctccgcctgt accccgccgc ccgatgctc   1800
ctcccgcacg agtcctccgc cgactgcaag gtcggcggct acaacatccc gcgcgggtcg  1860
atgttgctca tcaacgcgta cgccatccac cgtgacccgg cggtgtggga ggagccggag  1920
aagttcatgc cggagaggtt cgaggacggc gggtgcgacg gcaatctctt gatgccgttc  1980
gggatgggga ggcggaggtg ccccggcgag acgctggcgc tgcgcacagt ggggttggtg  2040
ctgggcacgc tgatccagtg cttcgactgg gagagggtcg acggcgtgga ggtcgacatg  2100
actgaaggtg gcgggctcac catccccaag gtcgtgccgt tggaggccat gtgcaggccg  2160
cgcgacgcca tgggtggtgt tcttcgcgag ctcgtctga                         2199
```

-continued

```
<210> SEQ ID NO 3
<211> LENGTH: 521
<212> TYPE: PRT
<213> ORGANISM: Zea mays

<400> SEQUENCE: 3

Met Asp Lys Ala Tyr Ile Ala Ala Leu Ser Ala Ala Leu Phe Leu
1               5                   10                  15

Leu His Tyr Leu Leu Gly Arg Arg Ala Gly Glu Gly Lys Ala Lys
                20                  25                  30

Ala Lys Gly Ser Arg Arg Leu Pro Pro Ser Pro Pro Ala Ile Pro
                35                  40                  45

Phe Leu Gly His Leu His Leu Val Lys Ala Pro Phe His Gly Ala Leu
    50                  55                  60

Ala Arg Leu Ala Ala Arg His Gly Pro Val Phe Ser Met Arg Leu Gly
65                  70                  75                  80

Thr Arg Arg Ala Val Val Val Ser Ser Pro Asp Cys Ala Arg Glu Cys
                85                  90                  95

Phe Thr Glu His Asp Val Asn Phe Ala Asn Arg Pro Leu Phe Pro Ser
                100                 105                 110

Met Arg Leu Ala Ser Phe Asp Gly Ala Met Leu Ser Val Ser Ser Tyr
                115                 120                 125

Gly Pro Tyr Trp Arg Asn Leu Arg Arg Val Ala Ala Val Gln Leu Leu
130                 135                 140

Ser Ala His Arg Val Gly Cys Met Ala Pro Ala Ile Glu Ala Gln Val
145                 150                 155                 160

Arg Ala Met Val Arg Arg Met Asp Arg Ala Ala Ala Gly Gly Gly
                165                 170                 175

Gly Val Ala Arg Val Gln Leu Lys Arg Arg Leu Phe Glu Leu Ser Leu
                180                 185                 190

Ser Val Leu Met Glu Thr Ile Ala His Thr Lys Thr Ser Arg Ala Glu
                195                 200                 205

Ala Asp Ala Asp Ser Asp Met Ser Thr Glu Ala His Glu Phe Lys Gln
210                 215                 220

Ile Val Asp Glu Leu Val Pro Tyr Ile Gly Thr Ala Asn Arg Trp Asp
225                 230                 235                 240

Tyr Leu Pro Val Leu Arg Trp Phe Asp Val Phe Gly Val Arg Asn Lys
                245                 250                 255

Ile Leu Asp Ala Val Gly Arg Arg Asp Ala Phe Leu Gly Arg Leu Ile
                260                 265                 270

Asp Gly Glu Arg Arg Arg Leu Asp Ala Gly Asp Glu Ser Glu Ser Lys
                275                 280                 285

Ser Met Ile Ala Val Leu Leu Thr Leu Gln Lys Ser Glu Pro Glu Val
                290                 295                 300

Tyr Thr Asp Thr Val Ile Thr Ala Leu Cys Ala Asn Leu Phe Gly Ala
305                 310                 315                 320

Gly Thr Glu Thr Thr Ser Thr Thr Glu Trp Ala Met Ser Leu Leu
                325                 330                 335

Leu Asn His Arg Glu Ala Leu Lys Lys Ala Gln Ala Glu Ile Asp Ala
                340                 345                 350

Ala Val Gly Thr Ser Arg Leu Val Thr Ala Asp Asp Val Pro His Leu
                355                 360                 365

Thr Tyr Leu Gln Cys Ile Val Asp Glu Thr Leu Arg Leu His Pro Ala
                370                 375                 380
```

```
Ala Pro Leu Leu Pro His Glu Ser Ala Ala Asp Cys Thr Val Gly
385                 390                 395                 400

Gly Tyr Asp Val Pro Arg Gly Thr Met Leu Leu Val Asn Val His Ala
            405                 410                 415

Val His Arg Asp Pro Ala Val Trp Glu Asp Pro Asp Arg Phe Val Pro
        420                 425                 430

Glu Arg Phe Glu Gly Ala Gly Gly Lys Ala Glu Gly Arg Leu Leu Met
    435                 440                 445

Pro Phe Gly Met Gly Arg Arg Lys Cys Pro Gly Glu Thr Leu Ala Leu
450                 455                 460

Arg Thr Val Gly Leu Val Leu Ala Thr Leu Leu Gln Cys Phe Asp Trp
465                 470                 475                 480

Asp Thr Val Asp Gly Ala Gln Val Asp Met Lys Ala Ser Gly Gly Leu
            485                 490                 495

Thr Met Pro Arg Ala Val Pro Leu Glu Ala Met Cys Arg Pro Arg Thr
            500                 505                 510

Ala Met Arg Gly Val Leu Lys Arg Leu
            515                 520

<210> SEQ ID NO 4
<211> LENGTH: 1566
<212> TYPE: DNA
<213> ORGANISM: Zea mays

<400> SEQUENCE: 4
atggataagg cctacatcgc cgccctctcc gccgccgccc tcttcttgct ccactacctc      60
ctgggccggc gggccggcgg cgagggcaag gccaaggcca agggctcgcg gcggcggctc     120
ccgccgagcc ctccggcgat cccgttcctg ggccacctcc acctcgtcaa ggccccgttc     180
cacggggcgc tggcccgcct cgctgcgcgc acggcccgg tgttctccat cgcgctgggg      240 accggagag ccgtggtcgt gtcgtcgccg gactgcgcca gggagtgctt cacggagcac      300
gacgtgaact cgcgaaccg gccgctgttc cgtcgatgc ggctggcgtc cttcgacggc       360
gccatgctct ccgtgtccag ctacggcccg tactggcgca acctgcgccg cgtcgccgcc     420
gtgcagctcc tctccgcgca ccgcgtcggg tgcatggccc cgccatcga agcgcaggtg      480 cgcgccatgg tgcggaggat ggaccgcgcc gccgcggccg gcggcggcgg cgtcgcgcgc     540
gtccagctca gcggcggct gttcgagctc tccctcagcg tgctcatgga gaccatcgcg      600
cacaccaaga cgtcccgcgc cgaggccgac gccgactcgg acatgtcgac cgaggcccac     660
gagttcaagc agatcgtcga cgagctcgtg ccgtacatcg gcacggccaa ccgctgggac     720 tacctgccg tgctgcgctg gttcgacgtg ttcggcgtga ggaacaagat cctcgacgcc      780
gtgggcagaa gggacgcgtt cctggggcgg ctcatcgacg gggagcggcg gaggctggac     840
gctggcgacg agagcgaaag taagagcatg attgcggtgc tgctcactct gcagaagtcc     900
gagccagagg tctacactga cactgtgatc actgctcttt gcgcgaacct attcggcgcc     960
ggaacggaga ccacgtccac cacgacggaa tgggccatgt cactgctgct gaaccaccgg    1020
gaggcgctca gaaggcgca ggccgagatc gacgcggcgg tgggcacctc cgcctggtg      1080 accgcggacg acgtgcccca cctcacctac ctgcagtgca tcgtcgacga dacgctgcgc    1140
ctgcacccgg ccgcgccgct gctgctgccg cacgagtccg ccgcggactg cacggtcggc    1200
ggctacgacg tgccgcgcgg cacgatgctg ctggtcaacg tgcacgcggt ccacagggac    1260
cccgcggtgt gggaggaccc ggacaggttc gtgccggagc ggttcgaggg cgccggcggc    1320
```

```
aaggccgagg ggcgcctgct gatgccgttc gggatggggc ggcgcaagtg ccccggggag    1380
acgctcgcgc tgcggaccgt cgggctggtg ctcgccacgc tgctccagtg cttcgactgg    1440
gacacggttg atggagctca ggttgacatg aaggctagcg gcgggctgac catgccccgg    1500
gccgtcccgt tggaggccat gtgcaggccg cgtacagcta tgcgtggtgt tcttaagagg    1560
ctctga                                                                1566
```

```
<210> SEQ ID NO 5
<211> LENGTH: 500
<212> TYPE: PRT
<213> ORGANISM: Oryza sativa

<400> SEQUENCE: 5

Met Asp Ala Leu Leu Val Glu Lys Val Leu Gly Leu Phe Val Ala
1               5                   10                  15

Ala Val Leu Ala Leu Val Val Ala Lys Leu Thr Gly Lys Arg Leu Arg
                20                  25                  30

Leu Pro Pro Gly Pro Ala Gly Ala Pro Ile Val Gly Asn Trp Leu Gln
            35                  40                  45

Val Gly Asp Asp Leu Asn His Arg Asn Leu Met Ala Leu Ala Arg Arg
50                  55                  60

Phe Gly Asp Ile Leu Leu Leu Arg Met Gly Val Arg Asn Leu Val Val
65                  70                  75                  80

Val Ser Ser Pro Asp Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Asp His Trp Arg Lys
            115                 120                 125

Met Arg Arg Ile Met Thr Val Pro Phe Phe Thr Asn Lys Val Val Ala
130                 135                 140

Gln Asn Arg Ala Gly Trp Glu Glu Ala Arg Leu Val Val Glu Asp
145                 150                 155                 160

Val Arg Arg Asp Pro Ala Ala Ala Thr Ser Gly Val Val Ile Arg Arg
                165                 170                 175

Arg Leu Gln Leu Met Met Tyr Asn Asp Met Phe Arg Ile Met Phe Asp
            180                 185                 190

Arg Arg Phe Asp Ser Val Asp Asp Pro Leu Phe Asn Lys Leu Lys Ala
            195                 200                 205

Phe Asn Ala Glu Arg Ser Arg Leu Ser Gln Ser Phe Glu Tyr Asn Tyr
210                 215                 220

Gly Asp Phe Ile Pro Val Leu Arg Pro Phe Leu Arg Arg Tyr Leu Ala
225                 230                 235                 240

Arg Cys His Gln Leu Lys Ser Gln Arg Met Lys Leu Phe Glu Asp His
                245                 250                 255

Phe Val Gln Glu Arg Lys Arg Val Met Glu Gln Thr Gly Glu Ile Arg
            260                 265                 270

Cys Ala Met Asp His Ile Leu Glu Ala Glu Arg Lys Gly Glu Ile Asn
            275                 280                 285

His Asp Asn Val Leu Tyr Ile Val Glu Asn Ile Asn Val Ala Ala Ile
        290                 295                 300

Glu Thr Thr Leu Trp Ser Ile Glu Trp Gly Ile Ala Glu Leu Val Asn
305                 310                 315                 320
```

His Pro Ser Ile Gln Ser Lys Val Arg Glu Glu Met Ala Ser Val Leu
            325                 330                 335

Gly Gly Ala Ala Val Thr Glu Pro Asp Leu Glu Arg Leu Pro Tyr Leu
        340                 345                 350

Gln Ala Val Val Lys Glu Thr Leu Arg Leu Arg Met Ala Ile Pro Leu
    355                 360                 365

Leu Val Pro His Met Asn Leu Ala Asp Gly Lys Leu Ala Gly Tyr Asp
370                 375                 380

Ile Pro Ala Glu Ser Lys Ile Leu Val Asn Ala Trp Phe Leu Ala Asn
385                 390                 395                 400

Asp Pro Lys Arg Trp Val Arg Pro Asp Glu Phe Arg Pro Glu Arg Phe
                405                 410                 415

Leu Glu Glu Lys Ala Val Glu Ala His Gly Asn Asp Phe Arg Phe
            420                 425                 430

Val Pro Phe Gly Val Gly Arg Ser Cys Pro Gly Ile Ile Leu Ala
                435                 440                 445

Leu Pro Ile Ile Gly Ile Thr Leu Gly Arg Leu Val Gln Ser Phe Asp
    450                 455                 460

Leu Leu Pro Pro Pro Gly Met Asp Lys Val Asp Thr Thr Glu Lys Pro
465                 470                 475                 480

Gly Gln Phe Ser Asn Gln Ile Leu Lys His Ala Thr Val Val Cys Lys
                485                 490                 495

Pro Ile Asp Ala
            500

<210> SEQ ID NO 6
<211> LENGTH: 1503
<212> TYPE: DNA
<213> ORGANISM: Oryza sativa

<400> SEQUENCE: 6
atggacgccc tcctcgtgga gaaggtcctc ctgggcctgt cgtggcggc ggtgctggcc      60 ctagtggtgg ccaagctcac cgggaagagg ctccgcctcc cgcccggccc cgccggcgct     120
cccatcgtcg gcaactggct ccaggtcggc gacgacctca ccaccgcaa cctgatggcg     180 ctggcgcggc ggttcggcga catcctcctc ctccgcatgg gcgtccgcaa cctggtggtg     240
gtgtccagcc cggacctcgc caaggaggtg ctccacaccc agggcgtcga gttcggctcc     300
cgcacccgca acgtggtgtt cgacatcttc accgggaagg ggcaggacat ggtgttcacc     360
gtgtacggcg accactggcg caagatgcgg cggatcatga cggtgccctt cttcaccaac     420
aaggtggtgg cccagaaccg cgcgggttgg gaggaggagg cgaggctggt ggtggaggac     480
gtccgccgcg accccgccgc ggcgacctcc ggcgtggtga tccggcgaag gttgcagctg     540
atgatgtaca cgacatgtt ccgcatcatg ttcgaccgcc gtttcgacag cgtggacgac     600
ccgctcttca caagctcaa ggccttcaac gcggagcgca gccgcctctc gcagagcttc     660
gagtacaact acggtgactt catccccgtc ctccgcccct cctccgccg ctacctcgca     720 cgctgccacc agctcaagtc ccagcgcatg aagctcttcg aggaccactt cgtccaggaa     780
cgcaagagag tgatggaaca gactggtgag atcggtgcg ccatgaccca catcctcgag     840
gccgagagga agggcgagat caaccacgac aacgtcctct acatcgtcga gaacatcaac     900
gttgctgcta tcgagacgac gctgtggtcg atcgaatggg gaatcgcgga gctggtgaac     960
cacccgagca tccagtcgaa ggtgcgggag gagatggcgt cggtgctggg cggcgcggc    1020 gtgacggagc cggacctgga gcggctgccg taccttcagg cggtggtgaa ggagacgctg    1080

-continued

```
cggttgcgca tggcgatccc gctgctggtg ccgcacatga acctcgccga cggcaagctc    1140
gccggctacg acatccccgc cgagtccaag atcctggtga acgcgtggtt cctcgccaac    1200
gaccccaagc ggtgggtgcg ccccgacgag tttaggccgg agaggttcct ggaggaggag    1260
aaggccgtgg aggcgcacgg caacgacttc cgcttcgtgc ccttcggcgt cggccgccgc    1320
agctgccccg ggatcatcct cgcgctgccc atcatcggga tcacgctcgg ccgcctcgtc    1380
cagagcttcg acctgctgcc gccgcccggg atggacaagg tggacaccac cgagaagccc    1440
ggccagttca gcaaccagat cctcaagcac gccaccgtcg tctgcaagcc catcgacgcc    1500
tag                                                                  1503
```

```
<210> SEQ ID NO 7
<211> LENGTH: 523
<212> TYPE: PRT
<213> ORGANISM: Oryza sativa

<400> SEQUENCE: 7
```

| Met | Leu | Met | Met | Leu | Gly | Ala | Ala | Ser | Gln | Trp | Ile | Leu | Ala | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Ala Ala Ala Ala Val Ala Ala Leu Leu Trp Leu Ala Val Ser Thr Leu
          20                  25                  30

Glu Trp Ala Trp Trp Thr Pro Arg Arg Leu Glu Arg Ala Leu Arg Ala
         35                  40                  45

Gln Gly Ile Arg Gly Asn Arg Tyr Arg Leu Phe Thr Gly Asp Val Pro
    50                  55                  60

Glu Asn Val Arg Leu Asn Arg Glu Ala Arg Lys Lys Pro Leu Pro Leu
65                  70                  75                  80

Gly Cys His Asp Ile Ile Pro Arg Val Leu Pro Met Phe Ser Lys Ala
                85                  90                  95

Val Glu Glu His Gly Lys Pro Ser Phe Thr Trp Phe Gly Pro Thr Pro
            100                 105                 110

Arg Val Met Ile Ser Asp Pro Glu Ser Ile Arg Glu Val Met Ser Asn
        115                 120                 125

Lys Phe Gly His Tyr Gly Lys Pro Lys Pro Thr Arg Leu Gly Lys Leu
    130                 135                 140

Leu Ala Ser Gly Val Val Ser Tyr Glu Gly Glu Lys Trp Ala Lys His
145                 150                 155                 160

Arg Arg Ile Leu Asn Pro Ala Phe His His Glu Lys Ile Lys Arg Met
                165                 170                 175

Leu Pro Val Phe Ser Asn Cys Cys Thr Glu Met Val Thr Arg Trp Glu
            180                 185                 190

Asn Ser Met Ser Ile Glu Gly Met Ser Glu Val Asp Val Trp Pro Glu
        195                 200                 205

Phe Gln Asn Leu Thr Gly Asp Val Ile Ser Lys Thr Ala Phe Gly Ser
    210                 215                 220

Ser Tyr Glu Glu Gly Arg Arg Ile Phe Gln Leu Gln Ala Glu Ser Ala
225                 230                 235                 240

Glu Arg Ile Ile Gln Ala Phe Arg Thr Ile Phe Ile Pro Gly Tyr Trp
                245                 250                 255

Phe Leu Pro Thr Lys Asn Asn Arg Arg Leu Arg Glu Ile Glu Arg Glu
            260                 265                 270

Val Ser Lys Leu Leu Arg Gly Ile Ile Gly Lys Arg Glu Arg Ala Ile
        275                 280                 285

```
Lys Asn Gly Glu Thr Ser Asn Gly Asp Leu Leu Gly Leu Leu Val Glu
    290                 295                 300

Ser Asn Met Arg Glu Ser Asn Gly Lys Ala Glu Leu Gly Met Thr Thr
305                 310                 315                 320

Asp Glu Ile Ile Glu Glu Cys Lys Leu Phe Tyr Phe Ala Gly Met Glu
                325                 330                 335

Thr Thr Ser Val Leu Leu Thr Trp Thr Leu Ile Val Leu Ser Met His
                340                 345                 350

Pro Glu Trp Gln Glu Arg Ala Arg Glu Val Leu His His Phe Gly
            355                 360                 365

Arg Thr Thr Pro Asp Tyr Asp Ser Leu Ser Arg Leu Lys Ile Val Thr
370                 375                 380

Met Ile Leu Tyr Glu Val Leu Arg Leu Tyr Pro Pro Val Val Phe Leu
385                 390                 395                 400

Thr Arg Arg Thr Tyr Lys Glu Met Glu Leu Gly Ile Lys Tyr Pro
                405                 410                 415

Ala Glu Val Thr Leu Met Leu Pro Ile Leu Phe Ile His His Asp Pro
            420                 425                 430

Asp Ile Trp Gly Lys Asp Ala Gly Glu Phe Asn Pro Gly Arg Phe Ala
            435                 440                 445

Asp Gly Ile Ser Asn Ala Thr Lys Tyr Gln Thr Ser Phe Phe Pro Phe
            450                 455                 460

Gly Trp Gly Pro Arg Ile Cys Ile Gly Gln Asn Phe Ala Leu Leu Glu
465                 470                 475                 480

Ala Lys Met Ala Ile Cys Thr Ile Leu Gln Arg Phe Ser Phe Glu Leu
            485                 490                 495

Ser Pro Ser Tyr Ile His Ala Pro Phe Thr Val Ile Thr Leu His Pro
                500                 505                 510

Gln His Gly Ala Gln Ile Lys Leu Lys Lys Ile
            515                 520

<210> SEQ ID NO 8
<211> LENGTH: 1572
<212> TYPE: DNA
<213> ORGANISM: Oryza sativa

<400> SEQUENCE: 8
atgctgatga tgctaggggc ggcctcccag tggatcctgg ccgccgccgc ggcggcggcc      60
gtggcggcgc tgctgtggct ggccgtgtcg acgctggagt gggcctggtg gacgccgcgg     120
cggctggagc gcgccctccg ggcgcagggc atcggggca accggtaccg cctcttcacc      180
ggcgacgtgc cggagaacgt ccggctcaac cggaggccc ggaagaagcc gctgccgctc      240
ggctgccacg acatcatccc gcgcgtgctg ccgatgttca gcaaagccgt tgaggagcac     300
gggaaaccat cattcacttg gttttggccca acgccaagag tgatgatttc agaccctgaa    360
tcaataaggg aagttatgtc taataagttt ggccactatg caaaccaaa gcctacccgt      420 ctcggaaagt tgctagcctc cggagttgta agctatgaag gcgagaaatg gcaaagcac      480 cggagaattc tgaatcctgc cttcaccac gagaaaataa gcggatgct gccagttttt       540 tctaactgct gcacggaaat ggttacaaga tgggagaatt caatgtctat tgaaggaatg     600
tcagaggtag atgtttggcc tgagttccaa aatcttacag agatgtcat atcaaagaca     660 gcattcggta gcagctatga ggaaggaagg agaattttc agctgcaagc agagtcagcc     720
gaacgcataa tacaagcctt tcggacaatt tttataccag gatattggtt cttaccaact    780
```

```
aaaaacaaca gaaggttgag agaaattgaa agagaggtca gcaaacttct acgaggaata    840
attggaaaga gagagcgggc tattaaaaat ggtgaaacca gtaatggtga cttgttgggc    900
ttattggtgg agtcaaatat gagggagtca atgggaaag cagaactagg aatgactacg    960
gacgaaatta ttgaggaatg caagctattt tattttgcag gaatggagac aacatcagta   1020
ttgctcactt ggacattaat tgtgctaagt atgcacccag agtggcaaga gcgagcaaga   1080
gaagaagtgc tacaccactt tggaagaacc acaccagact atgatagctt aagtcgtctg   1140
aagattgtaa caatgattct gtacgaggtt cttaggttgt atccgccagt ggtgttcttg   1200
accagacgaa catacaagga aatggagctc ggcggcatca atatcccgc tgaagtgacc   1260 cttatgttgc ccatttttatt tattcaccat gatcccgata tttggggaaa agatgcaggt   1320
gaattcaatc cagggaggtt tgctgatggc atctccaacg caacgaagta tcagacctct   1380
ttctttccat ttggatgggg tccccgaatc tgcatcggcc agaactttgc actattggaa   1440
gccaagatgg ctatctgtac aatccttcag cggttctcct ttgagctttc accatcgtac   1500
atccacgcac cattcactgt gataactctc cacccacagc atggtgcaca aattaagctg   1560
aagaaaatct aa                                                      1572

<210> SEQ ID NO 9
<211> LENGTH: 514
<212> TYPE: PRT
<213> ORGANISM: Triticum aestivum

<400> SEQUENCE: 9

Met Gly Leu Val Trp Met Val Ala Ala Val Ala Ala Val Leu Ala
1               5                   10                  15

Ser Trp Ala Phe Asp Ala Leu Val Tyr Leu Val Trp Arg Pro Arg Ala
            20                  25                  30

Ile Thr Arg Gln Leu Arg Ala Gln Gly Val Gly Gly Pro Gly Tyr Arg
        35                  40                  45

Phe Phe Ala Gly Asn Leu Ala Glu Ile Lys Gln Leu Arg Ala Asp Ser
    50                  55                  60

Ala Gly Ala Ala Leu Asp Ile Gly Asp His Asp Phe Val Pro Arg Val
65                  70                  75                  80

Gln Pro His Phe Arg Lys Trp Ile Pro Ile His Gly Arg Thr Phe Leu
                85                  90                  95

Tyr Trp Phe Gly Ala Lys Pro Thr Leu Cys Ile Ala Asp Val Asn Val
            100                 105                 110

Val Lys Gln Val Leu Ser Asp Arg Gly Gly Leu Tyr Pro Lys Ser Ile
        115                 120                 125

Gly Asn Pro His Ile Ala Arg Leu Leu Gly Lys Gly Leu Val Leu Thr
    130                 135                 140

Asp Gly Asp Asp Trp Lys Arg His Arg Lys Val Val His Pro Ala Phe
145                 150                 155                 160

Asn Met Asp Lys Leu Lys Met Met Thr Val Thr Met Ser Asp Cys Ala
                165                 170                 175

Gly Ser Met Met Ser Glu Trp Lys Ala Lys Met Asp Lys Gly Gly Ser
            180                 185                 190

Val Glu Ile Asp Leu Ser Ser Gln Phe Glu Glu Leu Thr Ala Asp Val
        195                 200                 205

Ile Ser His Thr Ala Phe Gly Ser Ser Tyr Glu Gln Gly Lys Lys Val
    210                 215                 220
```

-continued

```
Phe Leu Ala Gln Arg Glu Leu Gln Phe Leu Ala Ser Thr Val Phe
225                 230                 235                 240

Asn Val Gln Ile Pro Ser Phe Arg Tyr Leu Pro Thr Glu Lys Asn Leu
            245                 250                 255

Lys Ile Trp Lys Leu Asp Lys Glu Val Arg Thr Met Leu Met Asn Ile
        260                 265                 270

Ile Lys Gly Arg Leu Ala Thr Lys Asp Thr Met Gly Tyr Gly Asn Asp
    275                 280                 285

Leu Leu Gly Leu Met Leu Glu Ala Cys Ala Pro Glu Asp Gly Gln Asn
290                 295                 300

Pro Leu Leu Ser Met Asp Glu Ile Ile Asp Glu Cys Lys Thr Phe Phe
305                 310                 315                 320

Phe Ala Gly His Asp Thr Ser Ser His Leu Leu Thr Trp Thr Met Phe
                325                 330                 335

Leu Leu Ser Thr His Pro Glu Trp Gln Glu Lys Leu Arg Glu Glu Val
            340                 345                 350

Leu Arg Glu Cys Gly Asn Gly Ile Pro Thr Gly Asp Met Leu Asn Lys
        355                 360                 365

Leu Gln Leu Val Asn Met Phe Leu Leu Glu Thr Leu Arg Leu Tyr Ala
    370                 375                 380

Pro Val Ser Ala Ile Gln Arg Lys Ala Gly Ser Asp Leu Glu Val Gly
385                 390                 395                 400

Gly Ile Lys Val Thr Glu Gly Thr Phe Leu Thr Ile Pro Ile Ala Thr
                405                 410                 415

Ile His Arg Asp Lys Glu Val Trp Gly Glu Asp Ala Asn Lys Phe Lys
            420                 425                 430

Pro Met Arg Phe Glu Asn Gly Val Thr Arg Ala Gly Lys His Pro Asn
        435                 440                 445

Ala Leu Leu Ser Phe Ser Gly Pro Arg Ser Cys Ile Gly Gln Asn
    450                 455                 460

Phe Ala Met Ile Glu Ala Lys Ala Val Ile Ala Val Ile Leu Gln Arg
465                 470                 475                 480

Phe Ser Phe Ser Leu Ser Pro Lys Tyr Val His Ala Pro Met Asp Val
                485                 490                 495

Ile Thr Leu Arg Pro Lys Phe Gly Leu Pro Met Ile Leu Lys Ser Leu
            500                 505                 510

Glu Met

<210> SEQ ID NO 10
<211> LENGTH: 517
<212> TYPE: PRT
<213> ORGANISM: Oryza sativa

<400> SEQUENCE: 10

Met Gly Asn Leu Gly Trp Met Val Ala Ala Val Ala Ala Val Val
1               5                   10                  15

Ala Ser Trp Ala Phe Asp Ala Val Lys Leu Val Trp Arg Pro Arg
            20                  25                  30

Ala Ile Thr Arg Arg Leu Arg Ala Gln Gly Val Gly Gly Pro Gly Tyr
        35                  40                  45

Arg Phe Phe Ser Gly Asn Leu Gly Glu Ile Arg Arg Leu Arg Asp Glu
    50                  55                  60

Gly Ala Gly Val Val Leu Asp Val Ser Ser His Asp Phe Val Pro Ile
65                  70                  75                  80
```

```
Val Gln Pro His Phe Arg Lys Trp Ile Pro Leu Tyr Gly Lys Thr Phe
                85                  90                  95
Met Tyr Trp Phe Gly Ala Arg Pro Thr Ile Cys Leu Ala Asp Val Ser
            100                 105                 110
Met Val Arg Gln Val Leu Ser Asp Arg Thr Gly Met Tyr Pro Lys Asn
        115                 120                 125
Val Ser Asn Pro Tyr Phe Ala Arg Leu Leu Gly Lys Gly Leu Val Leu
    130                 135                 140
Thr Asp Gly Asp Glu Trp Lys Arg His Arg Lys Val Val His Pro Ala
145                 150                 155                 160
Phe Asn Met Asp Lys Leu Lys Met Met Thr Val Thr Met Ser Asp Cys
                165                 170                 175
Ala Gln Ser Met Ile Ser Glu Trp Glu Ser Glu Leu Gly Thr Lys Gly
            180                 185                 190
Asp Ile Val Glu Ile Glu Leu Ser Arg Arg Phe Glu Glu Leu Thr Ala
        195                 200                 205
Asp Val Ile Ser His Thr Ala Phe Gly Ser Ser Tyr Lys Glu Gly Lys
    210                 215                 220
Gln Val Phe Leu Ala Gln Arg Glu Leu Gln Phe Leu Ala Phe Ser Thr
225                 230                 235                 240
Phe Leu Ser Ile Gln Ile Pro Gly Ser Ser Tyr Leu Pro Thr Lys Lys
                245                 250                 255
Asn Leu Lys Thr Trp Ser Val Asp Lys Lys Val Arg Ser Met Leu Thr
            260                 265                 270
Asp Ile Ile Lys Ser Arg Leu Asn Asn Lys Asp Val Ala Gly Tyr Gly
        275                 280                 285
Asn Asp Leu Leu Gly Leu Met Leu Glu Ala Cys Ala Pro Glu His Gly
    290                 295                 300
Glu Ser Gln Pro Gln Leu Ser Met Asp Glu Ile Ile Ala Glu Cys Lys
305                 310                 315                 320
Thr Phe Phe Phe Ala Gly His Asp Thr Thr Ser His Leu Leu Thr Trp
                325                 330                 335
Thr Met Phe Leu Leu Ser Thr His Pro Glu Trp Gln Glu Lys Leu Arg
            340                 345                 350
Glu Glu Val Ala Thr Glu Cys Asp Gly Lys Val Pro Thr Gly Asp Met
        355                 360                 365
Leu Asn Lys Leu Lys Leu Val Asn Met Phe Leu Leu Glu Thr Leu Arg
    370                 375                 380
Leu Tyr Gly Pro Val Ala Phe Ile Gln Arg Arg Val Asn Ala Glu Leu
385                 390                 395                 400
Glu Leu Gly Gly Ile Thr Val Pro Glu Gly Thr Val Leu Ser Ile Pro
                405                 410                 415
Ile Ala Thr Ile His Arg Asp Lys Glu Val Trp Gly Glu Asp Ala Asp
            420                 425                 430
Ile Phe Lys Pro Glu Arg Phe Lys Asn Gly Val Ser Lys Ala Gly Lys
        435                 440                 445
Tyr Pro Asn Ala Leu Leu Ser Phe Ser Ser Gly Pro Arg Ala Cys Ile
    450                 455                 460
Gly Gln Asn Phe Ala Met Ile Glu Ala Lys Ala Val Ile Ala Met Ile
465                 470                 475                 480
Leu Gln Arg Phe Ser Phe Thr Leu Ser Pro Lys Tyr Val His Val Pro
                485                 490                 495
```

Thr Asp Val Ile Thr Leu Arg Pro Lys Tyr Gly Leu Pro Met Ile Leu
            500                 505                 510

Lys Ser Leu Lys Val
            515

<210> SEQ ID NO 11
<211> LENGTH: 533
<212> TYPE: PRT
<213> ORGANISM: Oryza sativa

<400> SEQUENCE: 11

Met Ala Ala Ser Ala Met Arg Val Ala Ile Ala Thr Gly Ala Ser Leu
1               5                   10                  15

Ala Val His Leu Phe Val Lys Ser Phe Val Gln Ala Gln His Pro Ala
            20                  25                  30

Leu Thr Leu Leu Leu Pro Val Ala Val Phe Val Gly Ile Ala Val Gly
        35                  40                  45

Ala Lys Gly Gly Ser Gly Gly Asp Gly Lys Ala Pro Pro Gly Pro Ala
    50                  55                  60

Ala Val Pro Val Phe Gly Asn Trp Leu Gln Val Gly Asn Asp Leu Asn
65                  70                  75                  80

His Arg Phe Leu Ala Ala Met Ser Ala Arg Tyr Gly Pro Val Phe Arg
                85                  90                  95

Leu Arg Leu Gly Val Arg Asn Leu Val Val Ser Asp Pro Lys Leu
            100                 105                 110

Ala Thr Glu Val Leu His Thr Gln Gly Val Glu Phe Gly Ser Arg Pro
        115                 120                 125

Arg Asn Val Val Phe Asp Ile Phe Thr Ala Asn Gly Ala Asp Met Val
    130                 135                 140

Phe Thr Glu Tyr Gly Asp His Trp Arg Arg Met Arg Arg Val Met Thr
145                 150                 155                 160

Leu Pro Phe Phe Thr Ala Arg Val Val Gln Gln Tyr Lys Ala Met Trp
                165                 170                 175

Glu Ala Glu Met Asp Ala Val Val Asp Asp Val Arg Gly Asp Ala Val
            180                 185                 190

Ala Gln Gly Thr Gly Phe Val Val Arg Arg Leu Gln Leu Met Leu
        195                 200                 205

Tyr Asn Ile Met Tyr Arg Met Met Phe Asp Ala Arg Phe Glu Ser Val
    210                 215                 220

Asp Asp Pro Met Phe Ile Glu Ala Thr Arg Phe Asn Ser Glu Arg Ser
225                 230                 235                 240

Arg Leu Ala Gln Ser Phe Glu Tyr Asn Tyr Gly Asp Phe Ile Pro Ile
                245                 250                 255

Leu Arg Pro Phe Leu Arg Gly Tyr Leu Asn Lys Cys Arg Asp Leu Gln
            260                 265                 270

Ser Arg Arg Leu Ala Phe Phe Asn Asn Tyr Val Glu Lys Arg Arg
        275                 280                 285

Lys Val Met Asp Thr Pro Gly Asp Arg Asn Lys Leu Arg Cys Ala Ile
    290                 295                 300

Asp His Ile Leu Glu Ala Glu Lys Asn Gly Glu Leu Thr Ala Glu Asn
305                 310                 315                 320

Val Ile Tyr Ile Val Glu Asn Ile Asn Val Ala Ala Ile Glu Thr Thr
                325                 330                 335

Leu Trp Ser Ile Glu Trp Ala Leu Ala Glu Val Val Asn His Pro Ala
            340                 345                 350

-continued

```
Val Gln Ser Lys Val Arg Ala Glu Ile Asn Asp Val Leu Gly Asp Asp
            355                 360                 365

Glu Pro Ile Thr Glu Ser Ser Ile His Lys Leu Thr Tyr Leu Gln Ala
        370                 375                 380

Val Ile Lys Glu Thr Leu Arg Leu His Ser Pro Ile Pro Leu Leu Val
385                 390                 395                 400

Pro His Met Asn Leu Glu Glu Ala Lys Leu Gly Gly Tyr Thr Ile Pro
                405                 410                 415

Lys Gly Ser Lys Val Val Asn Ala Trp Trp Leu Ala Asn Asn Pro
            420                 425                 430

Ala Leu Trp Glu Asn Pro Glu Glu Phe Arg Pro Glu Arg Phe Leu Glu
            435                 440                 445

Lys Glu Ser Gly Val Asp Ala Thr Val Ala Gly Lys Val Asp Phe Arg
            450                 455                 460

Phe Leu Pro Phe Gly Val Gly Arg Arg Ser Cys Pro Gly Ile Ile Leu
465                 470                 475                 480

Ala Leu Pro Ile Leu Ala Leu Ile Val Gly Lys Leu Val Arg Ser Phe
                485                 490                 495

Glu Met Val Pro Pro Gly Val Glu Lys Leu Asp Val Ser Glu Lys
            500                 505                 510

Gly Gly Gln Phe Ser Leu His Ile Ala Lys His Ser Val Val Ala Phe
            515                 520                 525

His Pro Ile Ser Ala
            530

<210> SEQ ID NO 12
<211> LENGTH: 510
<212> TYPE: PRT
<213> ORGANISM: Oryza sativa

<400> SEQUENCE: 12

Met Glu Ser Met Leu Val Ala Gly Ala Gly Ala Ala Val Ala Ala
1               5                   10                  15

Val Gly Gly Leu Val Ala Ala Ala Leu Ala Asp Lys Leu Val Ala
            20                  25                  30

Ala Pro Pro Arg Lys Asn Arg Ala Asn Pro Pro Ala Val Pro
        35                  40                  45

Gly Leu Pro Ile Ile Gly Asn Leu His Gln Leu Lys Glu Lys Lys Pro
    50                  55                  60

His Gln Thr Phe Ala Lys Trp Ser Glu Thr Tyr Gly Pro Ile Tyr Thr
65                  70                  75                  80

Ile Lys Thr Gly Ala Ser Pro Val Val Leu Asn Ser Thr Glu Val
                85                  90                  95

Ala Lys Glu Ala Met Ile Asp Lys Phe Ser Ser Ile Ser Thr Arg Lys
            100                 105                 110

Leu Pro Lys Ala Met Ser Val Leu Thr Arg Lys Ser Met Val Ala Ile
            115                 120                 125

Ser Asp Tyr Gly Asp Tyr Gln Lys Met Ala Lys Arg Asn Ile Met Ile
        130                 135                 140

Gly Met Leu Gly Phe Asn Ala Gln Lys Gln Phe Arg Gly Thr Arg Glu
145                 150                 155                 160

Arg Met Ile Ser Asn Val Leu Ser Thr Leu His Lys Leu Val Ser Leu
                165                 170                 175

Asp Pro His Ser Pro Leu Asn Phe Arg Asp Val Tyr Ile Asn Glu Leu
            180                 185                 190
```

```
Phe Ser Leu Ser Leu Ile Gln Ser Leu Gly Glu Asp Val Ser Ser Val
            195                 200                 205

Tyr Val Glu Glu Phe Gly Arg Glu Ile Ser Lys Asp Glu Ile Phe Asp
210                 215                 220

Val Leu Val His Glu Met Met Met Cys Ala Val Glu Ala Asp Trp Arg
225                 230                 235                 240

Asp Tyr Phe Pro Tyr Leu Ser Trp Leu Pro Asn Lys Ser Phe Asp Thr
                245                 250                 255

Ile Val Ser Thr Thr Glu Phe Arg Arg Asp Ala Ile Met Asn Ala Leu
            260                 265                 270

Ile Lys Lys Gln Lys Glu Arg Ile Ala Arg Gly Glu Ala Arg Ala Ser
        275                 280                 285

Tyr Ile Asp Phe Leu Leu Glu Ala Glu Arg Ser Ala Gln Leu Thr Asp
    290                 295                 300

Asp Gln Leu Met Leu Leu Ser Glu Ser Ile Leu Ala Ala Ala Asp
305                 310                 315                 320

Thr Val Leu Val Thr Thr Glu Trp Thr Met Tyr Glu Ile Ala Lys Asn
                325                 330                 335

Pro Asp Lys Gln Glu Leu Leu Tyr Gln Glu Ile Arg Glu Ala Cys Gly
                340                 345                 350

Gly Glu Ala Val Thr Glu Asp Asp Leu Pro Arg Leu Pro Tyr Leu Asn
            355                 360                 365

Ala Val Phe His Glu Thr Leu Arg Leu His Ser Pro Val Pro Val Leu
        370                 375                 380

Pro Pro Arg Phe Val His Asp Asp Thr Thr Leu Ala Gly Tyr Asp Ile
385                 390                 395                 400

Ala Ala Gly Thr Gln Met Met Ile Asn Val Tyr Ala Cys His Met Asp
                405                 410                 415

Glu Lys Val Trp Glu Ser Pro Gly Glu Trp Ser Pro Glu Arg Phe Leu
                420                 425                 430

Gly Glu Gly Phe Glu Val Ala Asp Arg Tyr Lys Thr Met Ala Phe Gly
            435                 440                 445

Ala Gly Arg Arg Thr Cys Ala Gly Ser Leu Gln Ala Met Asn Ile Ala
        450                 455                 460

Cys Val Ala Val Ala Arg Leu Val Gln Glu Leu Glu Trp Arg Leu Arg
465                 470                 475                 480

Glu Gly Asp Gly Asp Lys Glu Asp Thr Met Gln Phe Thr Ala Leu Lys
                485                 490                 495

Leu Asp Pro Leu His Val His Leu Lys Pro Arg Gly Arg Met
                500                 505                 510

<210> SEQ ID NO 13
<211> LENGTH: 506
<212> TYPE: PRT
<213> ORGANISM: Oryza sativa

<400> SEQUENCE: 13

Met Glu Arg Asp Ala Trp Leu Leu Cys Ala Ala Leu Ala Ala Ala Thr
1               5                   10                  15

Val Val Tyr Tyr Leu Ala Cys Thr Thr Ser Arg Arg Ala Gln Arg Arg
                20                  25                  30

Arg Leu Pro Pro Gly Pro Thr Pro Leu Pro Val Ile Gly Asn Val Leu
            35                  40                  45

Ser Leu Arg Gly Asn Met His His Ala Leu Ala Arg Leu Ala Arg Glu
        50                  55                  60
```

-continued

Arg Tyr Gly Pro Val Met Ala Leu Lys Leu Gly Leu Val Thr Ala Val
 65                  70                  75                  80

Val Val Ser Ser Pro Asp Ala Ala Arg Glu Ala Phe Thr Lys His Asp
                 85                  90                  95

Arg Arg Leu Ala Ala Arg Ala Val Pro Asp Thr Ser Arg Val Arg Gly
            100                 105                 110

Phe Ala Asp Arg Ser Met Ile Trp Leu Pro Ser Ser Asp Thr Arg Trp
        115                 120                 125

Lys Thr Leu Arg Gly Val Val Ala Thr His Val Phe Ser Pro Arg Ser
    130                 135                 140

Ile Ala Ala Ala Arg Gly Val Arg Glu Arg Lys Val Arg Asp Ile Val
145                 150                 155                 160

Gly Tyr Phe Ala Ala His Val Gly Glu Val Val Asp Val Gly Glu Ala
                165                 170                 175

Val Tyr Ser Gly Val Val Asn Leu Val Ser Asn Ala Phe Phe Ser Gly
            180                 185                 190

Asp Val Val Asp Val Gly Glu Glu Ser Ala His Gly Leu Arg Glu Ala
        195                 200                 205

Val Glu Asp Ile Ile Leu Ala Ile Ala Lys Pro Asn Val Ser Asp Leu
    210                 215                 220

Phe Pro Phe Leu Arg Pro Leu Asp Leu Gln Gly Trp Arg Arg Trp Ala
225                 230                 235                 240

Glu Lys Arg Tyr Asp Thr Val Phe Asp Ile Leu Asp Asn Ile Thr Asn
                245                 250                 255

Ser Arg Leu Ala Asp Ala Ser Ala Gly Asn His Ala Gly Asp Phe Leu
            260                 265                 270

Asp Ser Leu Leu Gly Leu Met Ser Tyr Gly Lys Ile Ala Arg Asp Asp
        275                 280                 285

Val Thr Thr Ile Met Phe Asp Val Phe Gly Ala Gly Thr Asp Thr Ile
    290                 295                 300

Ala Ile Thr Val Gln Trp Ala Met Ala Glu Leu Leu Arg Asn Pro Ser
305                 310                 315                 320

Ile Met Ala Lys Ala Arg Thr Glu Met Glu Asp Val Leu Ala Gly Lys
                325                 330                 335

Lys Thr Ile Glu Glu Asn Asp Thr Glu Lys Leu Pro Tyr Leu Arg Ala
            340                 345                 350

Val Ile Lys Glu Ala Met Arg Leu His Pro Val Ala Pro Ile Leu Leu
        355                 360                 365

Pro His Gln Ala Ala Glu Asp Gly Val Glu Ile Gly Gly Tyr Ala Val
    370                 375                 380

Pro Lys Gly Ser Thr Val Ile Phe Asn Val Trp Ala Ile Met Arg Asp
385                 390                 395                 400

Pro Thr Ala Trp Glu Arg Pro Asp Glu Phe Met Pro Glu Arg Phe Leu
                405                 410                 415

Gln Arg Ala Glu Val Asp Phe Arg Gly Lys Asp Phe Glu Phe Met Pro
            420                 425                 430

Phe Gly Ala Gly Arg Arg Leu Cys Pro Gly Leu Pro Met Ala Glu Arg
        435                 440                 445

Val Val Pro Phe Ile Leu Ala Ser Leu Leu His Ala Phe Glu Trp Arg
    450                 455                 460

Leu Pro Asp Gly Met Ser Ala Glu Glu Leu Asp Val Ser Glu Lys Phe
465                 470                 475                 480

```
Thr Thr Ala Asn Val Leu Thr Val Pro Leu Lys Ala Val Pro Ile Leu
                485                 490                 495

Ala Ser Ser Ala Ser Glu Leu Gln Ala Ser
            500                 505

<210> SEQ ID NO 14
<211> LENGTH: 509
<212> TYPE: PRT
<213> ORGANISM: Oryza sativa

<400> SEQUENCE: 14

Met Glu Val Glu Leu Pro Trp Gly Ala Arg Cys Ala Ala Ala Ala Phe
1               5                   10                  15

Phe Val Ser Ser Leu Cys Val Ala Ala Leu Gly Val Val Leu Leu Leu
            20                  25                  30

Leu Arg Arg Trp Pro Trp Cys Gly Cys His Val Cys Arg Ala Tyr Leu
        35                  40                  45

Ala Gly Ser Trp Arg Arg Glu Phe Ala Asn Leu Gly Asp Trp Tyr Ala
    50                  55                  60

Asp Leu Leu Arg Arg Ser Pro Thr Gly Thr Val His Val His Val Leu
65                  70                  75                  80

Gly Cys Thr Val Thr Ala Asn Pro Ala Asn Val Glu Tyr Met Leu Lys
                85                  90                  95

Thr Arg Phe Asp Asn Phe Pro Lys Gly Arg Pro Phe Ala Ala Leu Leu
            100                 105                 110

Gly Asp Leu Leu Gly Asp Gly Ile Phe Asn Val Asp Gly Asp Ala Trp
        115                 120                 125

Arg His Gln Arg Lys Met Ala Ser Leu Glu Leu Gly Ser Val Ala Val
    130                 135                 140

Arg Ser Tyr Ala Tyr Lys Ile Val Ala Gln Glu Val Glu Ala Arg Leu
145                 150                 155                 160

Met Pro Val Leu Ala Asn Ala Ala Asp Ser Gly Ala Val Val Asp Leu
                165                 170                 175

Gln Asp Val Phe Arg Arg Phe Ala Phe Asp Thr Ile Cys Lys Ile Ser
            180                 185                 190

Phe Gly Leu Asp Pro Gly Cys Leu Asp Arg Glu Met Pro Val Ser Glu
        195                 200                 205

Leu Ala Asp Ala Phe Asp Ala Ser Arg Leu Ser Ala Met Arg Gly
    210                 215                 220

Ala Ala Ala Ser Pro Leu Leu Trp Lys Met Lys Arg Phe Leu Asn Val
225                 230                 235                 240

Gly Ser Glu Arg Glu Leu Lys Lys Ala Ile Lys Leu Ile Asp Gly Leu
                245                 250                 255

Ala Ala Ala Met Ile Arg Glu Arg Lys Leu Gly Val Ala Asn Ser
            260                 265                 270

His Asp Leu Leu Ser Arg Phe Met Ala Ser Ser Gly Asp Asp Ala Arg
        275                 280                 285

Gly Ala Ala Asp Asp Lys Phe Leu Arg Asp Ile Val Val Ser Phe Leu
    290                 295                 300

Leu Ala Gly Arg Asp Thr Val Ser Ser Ala Leu Thr Thr Leu Phe Met
305                 310                 315                 320

Ile Leu Ser Lys Asn Pro Asp Val Ala Ala Ala Met Arg Ala Glu Ala
                325                 330                 335

Gly Ala Ala Ala Gly Glu Ser Ala Ala Val Ser Tyr Glu His Leu Lys
            340                 345                 350
```

```
Arg Leu Asn Tyr Thr His Ala Val Leu Tyr Glu Asn Met Arg Leu Phe
            355                 360                 365

Pro Pro Val Gln Phe Asp Ser Lys Phe Cys Ala Ala Asp Val Leu
    370                 375                 380

Pro Asp Gly Thr Tyr Val Asp Gly Gly Ala Arg Val Met Tyr His Pro
385                 390                 395                 400

Tyr Ala Met Gly Arg Met Pro Arg Ile Trp Gly Ala Asp Cys Asp Ala
                405                 410                 415

Phe Arg Pro Glu Arg Trp Leu Thr Gly Ala Gly Ala Phe Val Pro
            420                 425                 430

Glu Ser Leu Phe Lys Tyr Pro Val Phe Gln Ala Gly Leu Arg Val Cys
            435                 440                 445

Leu Gly Lys Glu Leu Ala Ile Thr Glu Met Lys Ala Val Ser Val Ala
            450                 455                 460

Val Val Arg Ala Phe Asp Val Glu Val Val Gly Glu Asn Gly Arg Cys
465                 470                 475                 480

Gly Gly Gly Ala Ala Ala Pro Arg Phe Val Pro Gly Leu Thr Ala
                485                 490                 495

Ser Ile Ser Gly Gly Leu Pro Val Lys Ile Arg Arg Val
            500                 505
```

<210> SEQ ID NO 15
<211> LENGTH: 520
<212> TYPE: PRT
<213> ORGANISM: Zea mays

<400> SEQUENCE: 15

```
Met Glu Arg Phe Tyr Tyr Val Ala Ala Thr Phe Val Leu Val Phe
1               5                   10                  15

Leu Leu His His Leu Leu Thr Arg Lys Lys Gln Gln Arg Leu Pro Pro
                20                  25                  30

Gly Pro Arg Phe Ala Tyr Pro Ile Leu Gly His Leu Pro Leu Val Lys
            35                  40                  45

Lys Pro Leu Gln Thr Ser Phe Ala Asp Leu Val Ser Arg His Gly Pro
    50                  55                  60

Ile Ile His Leu Arg Leu Gly Arg Arg His Ala Val Val Val Gly Ser
65              70                  75                  80

Ala Ala Val Ala Lys Glu Cys Phe Ser Gly Glu Leu Asp Val Ala Ile
                85                  90                  95

Ala Asn Arg Pro His Phe Pro Ser Ala Arg Glu Val Thr Phe Asp Tyr
            100                 105                 110

Ser Val Leu Thr Ala Val Asn Tyr Gly Ala Leu Trp Arg Thr Met Arg
            115                 120                 125

Arg Val Ser Thr Val His Leu Leu Ser Ala His Arg Val Asn Val Met
            130                 135                 140

Ser Asp Thr Val Ile Ala Arg Glu Leu Arg Val Met Val Arg Arg Leu
145                 150                 155                 160

Ala Arg Ala Ser Ala Ser Ala Pro Gly Asp Ala Ala Arg Val Glu Leu
                165                 170                 175

Lys Arg Arg Leu Phe Asp Leu Ser His Ser Val Leu Met Glu Thr Met
            180                 185                 190

Ala Gln Thr Lys Asn Thr Tyr Ser Asp Asp Pro Glu Glu Asp Met Ser
            195                 200                 205
```

```
Arg Glu Ala Arg Glu Met Lys Asp Ile Ile Glu Ile Ile Pro Leu
            210                 215                 220

Val Gly Ala Ala Asn Leu Trp Asn Tyr Val Pro Leu Leu Arg Trp Leu
225                 230                 235                 240

Asp Leu Tyr Gly Ala Lys Arg Lys Leu Ala Asp Val Val Asn Arg Arg
                245                 250                 255

Asp Leu Ile Phe Asp Asn Met Ile Gly Ala Glu Arg Gln Lys Leu Arg
            260                 265                 270

Gln Leu Glu Arg Lys Lys Gly Glu Ala His Ala Ser Glu Ser Asp Lys
        275                 280                 285

Met Gly Met Ile Gly Val Met Leu Ser Leu Gln Lys Thr Glu Pro Asp
290                 295                 300

Val Tyr Thr Asp Thr Phe Ile Asn Ala Leu Val Ser Asn Leu Leu Ala
305                 310                 315                 320

Ala Gly Thr Glu Thr Thr Ser Thr Thr Leu Glu Trp Ala Met Ser Leu
                325                 330                 335

Leu Leu Asn His Pro Asp Val Leu Lys Arg Ala Gln Glu Glu Ile Glu
            340                 345                 350

Ser Asn Val Gly Arg Asp Arg Leu Leu Asp Lys Asn Asp Leu Pro Arg
        355                 360                 365

Leu Pro Tyr Leu His Cys Ile Ile Ser Glu Thr Leu Arg Leu Tyr Pro
370                 375                 380

Pro Thr Pro Met Leu Leu Pro His Glu Ala Ser Thr Asp Cys Lys Ile
385                 390                 395                 400

His Gly Tyr Asp Val Pro Ala Gly Ser Met Val Leu Val Asn Ala Tyr
                405                 410                 415

Ala Ile His Arg Asp Pro Ala Met Trp Glu Asp Pro Glu Glu Phe Arg
            420                 425                 430

Pro Glu Arg Phe Glu Leu Gly Arg Ala Glu Gly Lys Phe Met Met Pro
        435                 440                 445

Phe Gly Met Gly Arg Arg Cys Pro Gly Glu Asn Leu Ala Met Arg
450                 455                 460

Thr Met Gly Leu Val Leu Gly Ala Leu Leu Gln Cys Phe Asp Trp Thr
465                 470                 475                 480

Arg Val Gly Asp Arg Glu Val Asp Met Ala Thr Ala Thr Gly Thr Ile
                485                 490                 495

Met Ser Lys Ala Val Pro Leu Glu Ala Gln Cys Lys Pro Arg Ala Asn
            500                 505                 510

Met Ser Ala Val Leu Gln Lys Ile
        515                 520

<210> SEQ ID NO 16
<211> LENGTH: 513
<212> TYPE: PRT
<213> ORGANISM: Zea mays

<400> SEQUENCE: 16

Met Asp Lys Ala Tyr Val Ala Val Leu Ser Val Ala Phe Leu Phe Leu
1               5                   10                  15

Val His Tyr Leu Val Gly Arg Ala Ala Pro Gly Gly Gly Lys Gly Arg
            20                  25                  30

Lys Arg Leu Pro Pro Ser Pro Leu Ala Ile Pro Phe Leu Gly His Leu
        35                  40                  45

His Leu Val Lys Thr Pro Phe His Ser Ala Leu Gly Arg Leu Ala Glu
    50                  55                  60
```

-continued

Arg His Gly Pro Val Phe Ser Leu Arg Met Gly Cys Arg Arg Ala Val
 65                  70                  75                  80

Val Val Ser Ser Pro Glu Cys Ala Arg Ala Cys Phe Thr Glu His Asp
                 85                  90                  95

Met Ser Phe Ala Asn Arg Pro Arg Phe Glu Ser Met Arg Leu Val Ser
            100                 105                 110

Phe Asp Gly Ala Met Leu Ser Val Ser Ser Tyr Gly Pro Tyr Trp Arg
        115                 120                 125

Thr Leu Arg Arg Val Ala Ala Val Gln Leu Leu Ser Ala His Arg Val
    130                 135                 140

Ala Cys Met Ser Pro Val Ile Cys Ala Glu Val Arg Ala Met Val Arg
145                 150                 155                 160

Arg Met Ala Arg Leu Ala Ala Gly Gly Ala Ala Arg Val Gln Leu Arg
                165                 170                 175

Arg Leu Phe Glu Leu Ser Leu Gly Val Leu Met Glu Thr Ile Ala
            180                 185                 190

Arg Thr Lys Thr Ser Arg Ser Glu Ala Cys Ala Ala Asp Thr Asp Val
            195                 200                 205

Ser Pro Glu Ala Ser Glu Leu Thr Arg Ile Ser Glu Glu Ile Met Pro
210                 215                 220

Tyr Leu Gly Thr Ala Asn Leu Trp Asp Tyr Leu Pro Phe Leu Arg Trp
225                 230                 235                 240

Phe Asp Val Phe Gly Val Arg Asn Lys Leu Met Ala Ala Val Arg Trp
                245                 250                 255

Arg Asp Ala Phe Leu Arg Arg Leu Ile Asp Ala Glu Arg Arg Arg Met
            260                 265                 270

Asp Gly Asp Gly Asp Gly Glu Lys Ser Met Ile Ala Val Leu Leu
            275                 280                 285

Ser Leu Gln Lys Ser Glu Pro Glu Leu Tyr Thr Asp Thr Met Ile Met
    290                 295                 300

Ala Leu Cys Gly Asp Leu Phe Gly Ala Gly Thr Glu Thr Thr Ser Val
305                 310                 315                 320

Thr Thr Glu Trp Ala Met Ser Leu Leu Leu Ser His Pro Glu Ala Leu
                325                 330                 335

Lys Lys Ala Gln Ala Glu Ile Asp Ala Val Val Gly Asn Ser Arg Arg
            340                 345                 350

Leu Ile Thr Ala Asp Asp Val Pro Arg Leu Gly Tyr Leu His Cys Val
        355                 360                 365

Ile Asn Glu Thr Leu Arg Met Tyr Pro Ala Ala Pro Leu Leu Leu Pro
    370                 375                 380

His Glu Ser Ala Ala Asp Cys Lys Val Gly Gly Tyr Asp Val Pro Arg
385                 390                 395                 400

Gly Thr Leu Leu Ile Val Asn Ala Tyr Ala Ile His Arg Asp Pro Ala
                405                 410                 415

Val Trp Glu Asp Pro Gly Ser Phe Leu Pro Glu Arg Phe Glu Asp Gly
            420                 425                 430

Lys Ala Glu Gly Arg Leu Leu Met Pro Phe Gly Met Gly Arg Arg Lys
        435                 440                 445

Cys Pro Gly Glu Thr Leu Ala Leu Arg Thr Val Gly Leu Val Leu Ala
    450                 455                 460

Thr Leu Leu Gln Cys Phe Asp Trp Asp Thr Val Asp Gly Ala Glu Val
465                 470                 475                 480

-continued

Asp Met Thr Glu Ser Gly Gly Leu Thr Met Pro Arg Ala Val Pro Leu
            485             490             495

Glu Ala Met Cys Lys Pro Arg Ala Ala Met Cys Asp Val Leu Arg Glu
            500             505             510

Leu

<210> SEQ ID NO 17
<211> LENGTH: 357
<212> TYPE: PRT
<213> ORGANISM: Zea mays

<400> SEQUENCE: 17

Met Asp Lys Ala Tyr Ile Ala Ala Leu Ser Ala Ala Leu Phe Leu
1               5                   10                  15

Leu His Tyr Leu Leu Gly Arg Arg Ala Gly Gly Glu Gly Lys Ala Lys
            20                  25                  30

Ala Lys Gly Ser Arg Arg Leu Pro Pro Ser Pro Pro Ala Ile Pro
            35                  40                  45

Phe Leu Gly His Leu His Leu Val Lys Ala Pro Phe His Gly Ala Leu
    50                  55                  60

Ala Arg Leu Ala Ala Arg His Gly Pro Val Phe Ser Met Arg Leu Gly
65                  70                  75                  80

Thr Arg Arg Ala Val Val Val Ser Ser Pro Asp Cys Ala Arg Glu Cys
                85                  90                  95

Phe Thr Glu His Asp Val Asn Phe Ala Asn Arg Pro Leu Phe Pro Ser
            100                 105                 110

Met Arg Leu Ala Ser Phe Asp Gly Ala Met Leu Ser Val Ser Ser Tyr
            115                 120                 125

Gly Pro Tyr Trp Arg Asn Leu Arg Arg Val Ala Ala Val Gln Leu Leu
    130                 135                 140

Ser Ala His Arg Val Gly Cys Met Ala Pro Ala Ile Glu Ala Gln Val
145                 150                 155                 160

Arg Ala Met Val Arg Arg Met Asp Arg Ala Ala Ala Gly Gly Gly
                165                 170                 175

Gly Val Ala Arg Val Gln Leu Lys Arg Arg Leu Phe Glu Leu Ser Leu
            180                 185                 190

Ser Val Leu Met Glu Thr Ile Ala His Thr Lys Thr Ser Arg Ala Glu
            195                 200                 205

Ala Asp Ala Asp Ser Asp Met Ser Thr Glu Ala His Glu Phe Lys Gln
    210                 215                 220

Ile Val Asp Glu Leu Val Pro Tyr Ile Gly Thr Ala Asn Arg Trp Asp
225                 230                 235                 240

Tyr Leu Pro Val Leu Arg Trp Phe Asp Val Phe Gly Val Arg Asn Lys
                245                 250                 255

Ile Leu Asp Ala Val Gly Arg Arg Asp Ala Phe Leu Gly Arg Leu Ile
            260                 265                 270

Asp Gly Glu Arg Arg Arg Leu Asp Ala Gly Asp Glu Ser Glu Ser Lys
            275                 280                 285

Ser Met Ile Ala Val Leu Leu Thr Leu Gln Lys Ser Glu Pro Glu Val
    290                 295                 300

Tyr Thr Asp Thr Val Ile Thr Ala Leu Cys Ala Val Ser Ala Ser Ser
305                 310                 315                 320

Ser Thr Ile Arg His Ser Leu Ile Leu Thr Lys Tyr Lys Lys Ser Cys
                325                 330                 335

```
Pro Phe Ser Gln Phe Ser Arg Gln His Ser Gly Leu Tyr Tyr Pro Pro
        340                 345                 350

Lys Tyr Arg Ile Arg
        355

<210> SEQ ID NO 18
<211> LENGTH: 1545
<212> TYPE: DNA
<213> ORGANISM: Triticum aestivum

<400> SEQUENCE: 18
atgggtcttg tctggatggt ggcggccgcc gtggcggcgg tgctggcctc gtgggcgttc      60
gacgcgctgg tgtacctcgt gtggaggccg cgggccatca cccggcagct ccgcgcgcag     120
ggcgtcggcg gtccgggcta caggttcttc gccgggaacc tcgccgagat caagcagctc     180
cgcgccgaca gcgccggcgc cgcgctggac atcggcgacc acgacttcgt ccccagggtc     240
cagccgcact ccgcaaatg gatccccatc cacgggcgca cgttcttgta ctggttcgga     300
gccaagccga cactgtgcat cgccgacgtg aacgtggtga agcaggtgct ctccgaccgc     360
ggcgggctgt accccaagag catcgggaac ccgcacatcg cccgcctgct cggcaagggg     420
ctcgtgctca ccgacggcga cgactggaag cgccaccgca aggtcgtcca cccggccttc     480
aacatggaca agctcaagat gatgacggtg accatgtccg actgtgccgg gtcaatgatg     540
tccgagtgga aggcaaagat ggacaagggc ggcagcgtgg agattgacct gagcagccag     600
tttgaggagc taaccgcgga tgtcatctcc cacacggcat tcggaagcag ctacgaacaa     660
gggaaaaagg tcttcctcgc gcagagggag ctccagtttc ttgccttctc caccgttttc     720
aacgtgcaaa tcccatcatt caggtaccttc caactgaaaa gaacctcaa atatggaag      780 cttgacaagg aggtgaggac catgctgatg aacatcataa aaggccgcct tgccaccaaa     840
gacaccatgg gctatggcaa cgacctcctc gggcttatgt tggaggcgtg tgcgccggag     900
gacgggcaaa tccgcttttt gagtatggat gagatcatag atgagtgcaa gacattcttt     960
tttgccgggc atgacaccag ctcgcatctg ctcacatgga ccatgttctt gctgagcacg    1020 cacccccgagt ggcaggagaa gctcaggag gaggtgctaa gagagtgtgg caacggtatt    1080
cccaccggtg acatgctcaa caaactgcag ttggtcaaca tgttcctact agaaactctc    1140
aggttgtacg cacctgtatc ggccattcag aggaaggcgg ttcggatct cgaggttggt    1200 ggcatcaaag tgaccgaagg cacgttccta acgatcccca tcgcgacgat acatcgcgac    1260
aaggaggtct ggggagaaga tgccaacaaa ttcaagccta tgaggttcga gaatggagtg    1320
acaagggccg gaaagcaccc caatgcatta ttgtctttct ccagtgggcc gaggtcatgc    1380
atagggcaga actttgcaat gatcgaggcc aaggccgtga tcgccgtgat tcttcagagg    1440
ttctcattct ccctatcacc aaagtatgtc catgccccca tggatgtgat cacgctgcgg    1500
cctaagtttg ggcttcccat gatcctcaag agcctagaga tgtaa                    1545

<210> SEQ ID NO 19
<211> LENGTH: 1554
<212> TYPE: DNA
<213> ORGANISM: Oryza sativa

<400> SEQUENCE: 19
atgggtaatc tggggtggat ggtggcggcg gcggtggcgg cggtggtggc gtcgtgggcg      60
ttcgacgcgg tggtgaagct ggtgtggagg ccccgcgcca tcaccaggcg gctgcgggcg     120
cagggcgtcg gcgggccggg ataccggttc ttctccggca acctcggcga gatcaggcgt     180
```

| | |
|---|---|
| ctccgcgacg agggcgccgg cgtcgtgctc gacgtctcct cccatgactt cgtccccatc | 240 |
| gtgcagccgc acttccgcaa atggatcccc ctctatggga agacattcat gtattggttc | 300 |
| ggagcgcggc ctaccatttg cttggcagac gtgagcatgg tgaggcaggt gttatcggac | 360 |
| cggacgggga tgtaccctaa gaacgtgtcg aacccatact tcgcacgact actcggcaag | 420 |
| gggcttgtgc tcaccgacgg cgatgagtgg aagcgccacc gcaaagtagt ccacccggca | 480 |
| tttaacatgg acaagctcaa gatgatgact gtgactatgt ccgattgtgc caatctatg | 540 |
| atttccgagt gggaatccga gttggggaca aagggcgata tagtggagat cgagctgagc | 600 |
| cgacgattcg aggagcttac cgctgatgtg atctcgcaca cagcattcgg gagcagctat | 660 |
| aaggagggga agcaagtgtt cttggcacaa agagagcttc aatttcttgc cttctccacc | 720 |
| ttccttagca tccaaatccc ggggtccagc tacctcccga ccaagaagaa cctaaagaca | 780 |
| tggtcagtgg acaagaaggt gagaagcatg ctcacggaca tcatcaagag ccggctcaac | 840 |
| aacaaagatg tcgcaggata cgggaacgac ctgctcggat taatgctgga ggcatgtgca | 900 |
| ccggagcacg gggagagcca gccacaactt agtatggacg agatcatcgc cgagtgcaag | 960 |
| acattcttct ttgcagggca cgacaccacc tcacaccttc tcacatggac catgttccta | 1020 |
| ttgagcacac atccggagtg gcaggagaag ctcagggagg aggtggcaac ggagtgtgac | 1080 |
| ggcaaggtgc ccaccggtga catgctcaac aagctgaagc tagtcaacat gttcctcctc | 1140 |
| gagaccctga ggttgtatgg ccctgttgca ttcatacaga ggagggtcaa cgccgagcta | 1200 |
| gaactcggcg gcatcacggt ccctgagggc actgtcctat cgattccgat gcaacaatc | 1260 |
| caccgcgata aggaggtgtg gggcgaggac gccgacatat tcaagccgga gaggttcaag | 1320 |
| aatggggtgt caaaggcggg aaaatatccc aacgcgttgc tctccttctc cagtgggccg | 1380 |
| agggcatgca ttgggcagaa cttcgccatg atcgaggcca aggccgtaat tgcaatgatc | 1440 |
| ctacagaggt tctcctttac tctatcaccc aagtacgtcc acgtgccaac cgacgtgatc | 1500 |
| acgcttcggc caaagtatgg gctgcctatg atcctcaaga gtctcaaggt gtag | 1554 |

<210> SEQ ID NO 20
<211> LENGTH: 1602
<212> TYPE: DNA
<213> ORGANISM: Oryza sativa

<400> SEQUENCE: 20

| | |
|---|---|
| atggcggcct ccgcgatgag ggtggccatc gccaccgggg cgtcgttggc ggtgcatttg | 60 |
| ttcgtcaagt cgttcgtgca ggcgcagcat cctgctctca ccttgctgct gccagtggct | 120 |
| gtgtttgtcg gcattgcggt gggcgcgaag ggcgggagcg gtggtgacgg gaaggcgccg | 180 |
| ccggggccgg cggccgtgcc ggtgttcggc aactggctgc aggtgggcaa cgacctgaac | 240 |
| caccggttcc tcgcggcgat gtcggcacgg tacggtcccg tgttccgtct gcggctgggc | 300 |
| gtgcgcaacc tggtggtggt gtcggacccg aagctggcga cggaggtgct gcacacgcag | 360 |
| ggcgtggagt tcggctcccg cccgcgcaac gtcgtcttcg acatcttcac cgccaacggc | 420 |
| gccgacatgg tgttcaccga gtacggcgac cactggcgac gcatgcgccg cgtcatgacg | 480 |
| ctgccgttct tcacgcgcgc cgtcgtgcag cagtacaagg ccatgtggga ggccgagatg | 540 |
| gacgccgtcg tggacgacgt gcgcggcgac gcggtggcgc agggcaccgg cttcgtggtg | 600 |
| cgacgcaggc tgcagctcat gctgtacaac atcatgtacc ggatgatgtt cgacgcgcgg | 660 |
| ttcgagtcgg tggacgaccc catgttcatc gaggccacca ggttcaactc cgagcgcagc | 720 |
| cgcctcgcgc agagcttcga gtacaactac ggcgacttca tccccatcct ccgtcccttc | 780 |

```
ttgcggggct acctcaacaa gtgccgtgac ctccagagca ggaggctcgc cttcttcaac      840
aacaactacg tcgagaagag aaggaaggtg atggacactc cgggagacag gaacaagctc      900
cggtgcgcga tcgaccatat ccttgaggcg gagaagaacg gcgagctgac ggcggagaac      960
gtgatctaca tcgtggagaa catcaacgtg gccgccatcg agacgacgct ctggtccatc     1020
gagtgggcgc tggccgaggt cgtcaaccac ccggcggtgc agagcaaggt ccgcgccgag     1080
atcaacgacg tgctcggcga cgacgagccc atcaccgagt ccagcatcca caagctgact     1140
tacctgcagg ccgtgatcaa ggagacgctg cggctgcact ccccgatccc gctgctggtg     1200
ccgcacatga acctggagga ggccaagctc ggcgggtaca ccatccccaa gggatccaag     1260
gtggtggtga acgcgtggtg gctggccaac aacccggcgc tgtgggagaa ccccgaggag     1320
ttccggcctg agcggttctt ggagaaggag agcggcgtgg acgccaccgt cgccgggaag     1380
gtggacttca ggttcctgcc cttcggcgtg ggccgccgca gctgcccggg gatcatcctg     1440
gcgctgccca tcctggcgct catcgtcggg aagctggtga ggagcttcga gatggtgccg     1500
ccgccgggcg tggagaagct ggacgtgagc gagaaaggcg ggcagttcag cctccacatc     1560
gccaagcact ccgtcgtcgc cttccacccc atctctgcct ga                       1602

<210> SEQ ID NO 21
<211> LENGTH: 1533
<212> TYPE: DNA
<213> ORGANISM: Oryza sativa

<400> SEQUENCE: 21
atggagtcga tgctcgtagc cggagcgggc gcggcggcgg tggcggccgt cgggggcctc       60
gtcgcggcgg ccgcgctcgc cgacaagctc gtcgcggcgc cgccgccgcg caagaaccgc      120
gccaacccgc ctcagctgt tcctggttta cccattattg gaaatctgca tcaattgaaa      180
gaaaagaagc ctcatcagac gtttgcaaaa tggtctgaaa cttatggacc aatctacact      240
ataaagaccg gagcttctcc agtggttgtg ctcaattcaa ctgaagtagc caaggaggcg      300
atgattgaca aattctcatc catatctact cgaaagctac caaaagcaat gtctgtgcta      360
actcgtaaaa gtatggtcgc aatcagcgac tacggtgact accaaaagat ggcgaagcgt      420
aatattatga ttggcatgtt aggttttaat gcacagaaac agtttcgcgg tacaagagag      480
aggatgatca gtaacgtgtt aagcactttg cataagttgg tttctcttga cccacattcc      540
cctctgaact tcagggatgt ttacattaat gagctgttca gcttgtcctt gatccagagt      600
ttaggtgagg atgtgagttc agtttatgtg gaagagtttg ggagggagat atccaaggac      660
gaaatctttg atgtccttgt gcatgagatg atgatgtgtg cagttgaggc tgactggagg      720
gactacttcc cctacctcag ctggcttcca aacaagagct tcgacacaat tgtgtctact      780
acagaattca gacgagatgc tatcatgaat gcattgatca agaagcagaa ggagaggatt      840
gcacgcggag aggcaagggc atcctacatt gacttcttgc tggaagctga gaggagtgca      900
cagctgacag atgaccaact gatgctgctg ctgtcggagt ccatcctggc tgcagctgat      960
actgtcctgg tgaccaccga atggaccatg tatgagattg ccaagaaccc tgacaaacag     1020
gagctactct accaagagat ccgagaggcg tgcggcggcg aggcggtgac cgaggacgac     1080
ttgccgcggc tgccgtacct caacgccgtg ttccacgaga cgctgcggct gcactccccg     1140
gtgccggtgc tgccccgag gttcgtccac gacgacacca cgctcgccgg ctacgacatc     1200
gcggcgggca cccagatgat gatcaacgtg tacgcgtgcc acatggacga aaggtgtgg     1260 gagtcgccgg gggagtggtc gccggagagg ttcctcggcg aggggttcga ggtggcggac     1320
```

| | |
|---|---|
| aggtacaaga cgatggcgtt cggcgccggg aggaggacct gcgcggggag cctgcaggcg | 1380 |
| atgaacatcg cgtgcgtcgc cgtggcgcgc ctcgtgcagg agctcgagtg gaggctgagg | 1440 |
| gagggcgacg gggacaagga ggacaccatg cagttcaccg ccttgaagct tgacccgctg | 1500 |
| catgtccacc tcaagcccag aggaaggatg tga | 1533 |

<210> SEQ ID NO 22
<211> LENGTH: 1521
<212> TYPE: DNA
<213> ORGANISM: Oryza sativa

<400> SEQUENCE: 22

| | |
|---|---|
| atggagcgcg acgcgtggct gctatgtgca gcgctcgccg cggcgacggt cgtctactac | 60 |
| ctcgcctgca cgacgtcgcg ccgcgcgcag cggcgtcgtc tgcctcctgg cccgacgccg | 120 |
| ctgccggtga tcggcaatgt gctcagcctg cgcggcaaca tgcaccacgc gctggcgcgc | 180 |
| ctcgcgcgcg agcggtatgg ccccgtgatg gcgctgaagc tgggcctcgt caccgccgtg | 240 |
| gtcgtctcct cgcccgacgc ggcgaggggag gcgttcacca gcacgaccg gcgcctcgcg | 300 |
| gcgcgcgccg tcccggacac cagccgcgtg cgcgggttcg ccgaccggtc catgatatgg | 360 |
| ctgccgagct ccgacacgcg ctggaagacg ctgcgcgggg tggtggccac gcacgtcttc | 420 |
| tcgccacgga gcatcgccgc ggcgcgcggc gtccgcgagc gcaaggtgcg cgacatcgtc | 480 |
| ggctacttcg ccgcgcacgt cggggaggtg gtcgacgtcg gcgaggccgt gtacagcggg | 540 |
| gtggtcaacc tcgtgtcgaa cgccttcttc tccggtgacg tggtcgacgt cggcgaggag | 600 |
| tcggcgcacg ggctacggga agccgtggag gacatcatct tggcgatcgc gaagcccaac | 660 |
| gtctccgacc ttttccctt cctccgcccg ctcgacctgc agggatggcg tcgctgggcg | 720 |
| gagaaacgct acgacacggt gttcgacatc ttggacaaca taaccaacag ccgtttggcc | 780 |
| gacgcctcgg caggaaacca cgccggcgac ttcctggact ccctcctcgg cctcatgtcc | 840 |
| tacggcaaga tcgctcgcga cgacgtgaca accataatgt tcgacgtgtt cggcgccggg | 900 |
| acagacacga tcgccatcac ggtgcagtgg gcgatggcgg agctgctccg caacccgagc | 960 |
| ataatggcca aggcgcgcac agagatggag gacgtcctcg ccggcaagaa aaccatcgag | 1020 |
| gagaacgaca cggagaagtt gccgtacctc cgggccgtga taaaggaggc aatgcggctt | 1080 |
| cacccggtgg caccgatact actgccgcac caggcggcgg aggacggcgt ggagatcggc | 1140 |
| ggctacgccg tgccgaaggg gtcgacggtg atcttcaacg tgtgggcgat catgcgtgac | 1200 |
| ccgacggcgt gggagaggcc ggacgagttc atgccagaga gattcctgca aagagcagag | 1260 |
| gtagatttcc gaggaaaaga cttcgagttc atgccgttcg gggccggaag gaggctgtgc | 1320 |
| ccggggttgc cgatggcaga gcgcgtcgtg ccattcatac tggcgtcgct gctgcacgcg | 1380 |
| ttcgagtgga ggctccccga cggcatgtcg gctgaggagt tggatgtcag tgagaagttc | 1440 |
| accacagcca atgttcttac tgtcccactg aaggccgtcc ccatacttgc ctctagtgct | 1500 |
| agtgaactac aagcaagcta g | 1521 |

<210> SEQ ID NO 23
<211> LENGTH: 1530
<212> TYPE: DNA
<213> ORGANISM: Oryza sativa

<400> SEQUENCE: 23

| | |
|---|---|
| atggaggtgg agttgccatg gggcgcgcgg tgcgcggcgg cggcgttctt cgtgtcctcg | 60 |
| ctgtgcgtgg cggcgctcgg cgtcgtgctc ctgctcctca ggcggtggcc gtggtgcggc | 120 |

```
tgccatgtct gccgcgccta cctggccggg tcgtggagga gggagttcgc caacctcggc    180
gactggtacg ccgacctgct ccgccgctcg ccgacgggca ccgtccacgt ccacgtcctc    240
ggctgcaccg tcacggcgaa cccggcgaac gtggagtaca tgctcaagac gcgcttcgac    300
aacttcccca aggggaggcc gttcgccgcg ctcctcggcg acctcctcgg cgacggcatc    360
ttcaacgtcg acgcgacgc gtggcgccac cagcggaaga tggccagcct cgagctgggg     420
agcgtcgccg tgagatccta cgcgtacaag atcgtcgccc aggaggtgga ggcccgcctc    480
atgccggtgc tcgccaacgc cgccgacagc ggcgccgtgg tcgacctgca ggacgtgttc    540
cgccgcttcg ccttcgacac catctgcaag atctccttcg gcctcgaccc gggctgcctc    600
gaccgggaga tgcccgtgtc ggagctcgcc gacgcgttcg acgccgcgtc gcggctgtcc    660
gccatgcgtg gcgcggcggc gtcgccgttg ctgtggaaga tgaagcggtt tctcaacgtc    720
gggtcggaga gggagctcaa gaaggccatc aagctcatcg acgggctcgc ggcggcgatg    780
atccggggagc gccggaagct tggcgtcgcg aacagccacg acctcctgtc ccggttcatg    840
gcctcctccg gcgacgacgc gcgcggcgcc ccgacgacaa agttcctccg cgacatcgtc    900
gtcagcttcc tcctcgccgg ccgggacacg gtgtcctccg cgctcaccac tctgttcatg    960
atcctgtcca agaaccccga cgtggcggcc gccatgcgcg cggaggccgg cgccgccgcc   1020
ggcgagagcg ccgccgtcag ctacgagcac ctgaagcggc tgaactacac ccacgccgtg   1080
ctgtacgaga acatgcggct gttcccgccg gtgcagttcg actccaagtt ctgcgccgcc   1140
gccgacgtgc tccccgacgg cacctacgtc gacggcggcg cgcgcgtcat gtaccacccc   1200
tacgccatgg gccgcatgcc gcgcatctgg ggcgccgact gcgacgcgtt ccggccggag   1260
cggtggctca ccggcgccgg cggcgcgttc gtgccggaga gcctcttcaa gtacccggtg   1320
ttccaggccg gcctccgcgt gtgcctcggc aaggagctcg ccatcaccga gatgaaggcg   1380
gtcagcgtcg ccgtcgtgag ggcattcgac gtcgaggtcg tcggcgagaa tggccggtgc   1440
ggcggcggcg ccgccgccgc gccaagattc gtgccggggc tcaccgcgtc catcagcggt   1500
gggctcccag tgaagatcag acgcgtttag                                    1530
```

<210> SEQ ID NO 24
<211> LENGTH: 1563
<212> TYPE: DNA
<213> ORGANISM: Zea mays

<400> SEQUENCE: 24

```
atggaaagat ctactacgt cgccgcggcc accttcgtgc tcgtcttcct gctccaccac     60
ctcttgacga ggaagaagca gcaacgtctg ccacccggcc cgcggttcgc gtaccccatc    120
ctcggccacc tccccttggt caagaagccg ctccagacct cgttcgccga cctcgtgtcg    180
cgccacggcc caattattca cctgcgcctc ggccgccgcc acgccgtcgt cgtcggctcg    240
gcggcggtgg cgaaggagtg cttctccgga gagctcgacg tcgcgatcgc caaccgcccg    300
cacttcccgt ccgcgcgcga ggtcaccttc gactactcgg tgctcacggc cgtcaactac    360
ggcgcgctct ggcgcaccat gcggcgcgtc tccaccgtgc acctcctctc ggcccaccgc    420
gtcaacgtca tgtcggacac cgtgatcgcc cgcgagctgc cgtcatggt gcgccgcctc    480
gcccgcgcct ccgcctccgc gccgggcgac gccgccagag tcgagctgaa gcggaggctg    540
tttgacctct cccacagcgt cctcatggag accatggcgc agaccaagaa cacctactcc    600
gacgacccga aggaggacat gtccagggag gcgcgcgaga tgaaggacat catcgaagag    660
atcatcccgc tcgttggtgc ggccaacctg tggaactacg tgcccctgct gcggtggctc    720
```

```
gatctctacg gcgccaagag gaagctcgcg gacgtggtta accgaaggga cttgatcttc      780
gacaacatga tcggtgcaga gcggcagaag ctgaggcagc tggaacgcaa gaaaggcgag      840
gcccatgcca gcgaatcgga taagatgggc atgatcggcg tcatgttatc gctgcagaaa      900
acagagcctg atgtctacac ggacaccttt atcaacgctc tcgtgtcaaa tctgctggcc      960
gccggcacgg agacgacctc gacgaccctg gaatgggcaa tgtcgctctt gcttaaccac     1020
ccagacgtgc tgaaaagggc gcaagaagag atcgaatcga acgtcggaag ggaccgtctt     1080
ctcgacaaga acgacctccc ccgcctgccc tacctccact gcatcatcag cgagactctt     1140
cgcctctacc ctcccacgcc gatgctgctg ccgcacgagg cgtccaccga ctgcaagatc     1200
cacgggtacg acgtcccggc ggggtcgatg gtcctcgtca atgcgtacgc catccaccgg     1260
gacccggcga tgtgggagga cccggaggag ttcaggccgg agcggttcga gctcggcagg     1320
gcagagggga agttcatgat gccgtttggg atggggaggc gcaggtgccc cggcgagaac     1380
ctcgcgatgc gaaccatggg gctggtcctg ggggcgctgc tccaatgctt cgattggacc     1440
agggttgggg atagagaagt tgacatggca acagccactg gcaccatcat gtctaaggct     1500
gtcccactcg aagctcagtg caagccgcga gcgaacatgt ctgctgttct tcagaaaatc     1560
tag                                                                   1563

<210> SEQ ID NO 25
<211> LENGTH: 1542
<212> TYPE: DNA
<213> ORGANISM: Zea mays

<400> SEQUENCE: 25
atggataagg cctatgtcgc cgtcctctcc gtcgccttcc tcttcttggt ccactacctc       60
gtgggccgcg ccgcccctgg cggcggcaag gggaggaagc ggctgccacc gagccctctg      120
gccatcccgt tcctcggcca cctccacctc gtcaagacgc cgttccactc ggcgctgggc      180
cgcctcgcgc agcgccacgg cccggtgttc tccctgcgca tggggtgccg ccgcgcggtg      240
gtcgtgtcct cgccggagtg cgccagggcg tgcttcacgg agcacgacat gagcttcgcc      300
aaccgcccgc gcttcgagtc catgcgcctc gtgtccttcg acggcgccat gctctcggtg      360
tccagctacg ggccctactg gcgcaccctc cgccgcgtcg ccgccgtgca gctcctctcc      420
gcgcaccgcg tcgcctgcat gtccccgtc atctgcgccg aggtgcgcgc catggtgcgc      480
cggatggctc gcctagccgc gggcggcgcc gcgcgcgtcc agctcaggcg gcgcctgttc      540
gagctctccc tcggcgtgct catggagacc atcgcgcgga ccaagacctc ccgctccgag      600
gcttgcgccg ccgacactga cgtgtcgccc gaggcgagcg agttgacgcg gatctccgaa      660
gagatcatgc cgtacctcgg cacggccaac ctgtgggact acctgccgtt cctgcggtgg      720
ttcgacgtgt tcggcgtgag gaacaagctc atggccgccg tgaggtggag ggacgcgttc      780
ctgcggcggc tcatcgacgc agagcgccgg aggatggacg gtgacggcga cggcgagaag      840
aagagcatga tcgccgtgct gctctctttg cagaagtcgg agccggagct gtacacggat      900
accatgatca tggcgctgtg cggggacttg tttggcgccg ggacggagac cacatcggtc      960
acgacagaat gggccatgtc gcttcttctg agccacccgg aggctctgaa gaaggcacag     1020
gcagagatcg acgcggtggt gggcaactcc cgccgcctga tcaccgccga cgacgtgccc     1080
cgcctcggct acctgcactg cgtcatcaac gagacccctg gcatgtaccc ggccgctccg     1140
ctgctgctgc cgcacgagtc ggcggcggac tgcaaggtcg gcggctacga cgtgccccgc     1200
gggacgctgc tgatcgtgaa cgcgtacgcc atccacaggg accccgcggt gtgggaggac     1260
```

```
ccgggcagct tcttgccgga gcggttcgag gacggcaagg ccgaggggcg gctgctgatg   1320
ccgttcggga tggggcggcg caagtgcccc ggcgagacgc tcgcgctgcg gaccgtcggg   1380
ctggtgcttg ccacgctgct ccagtgcttc gactgggaca cggttgatgg agctgaggtt   1440
gacatgacgg agagcggcgg gctgaccatg ccccgggccg tcccgttgga ggccatgtgc   1500
aagcctcgtg cagctatgtg cgatgttctt cgggagctct aa                     1542

<210> SEQ ID NO 26
<211> LENGTH: 1074
<212> TYPE: DNA
<213> ORGANISM: Zea mays

<400> SEQUENCE: 26
atggataagg cctacatcgc cgccctctcc gccgccgccc tcttcttgct ccactacctc     60
ctgggccgcc gggccggcgg cgagggcaag gccaaggcca agggctcgcg gcggcggctc    120
ccgccgagcc ctccggcgat cccgttcctg ggccacctcc acctcgtcaa ggccccgttc    180
cacggggcgc tggcccgcct cgcggcgcgc acggcccgg tgttctccat cgcgctgggg     240
acccggcgcg ccgtggtcgt gtcgtcgccg gactgcgcca gggagtgctt cacggagcac    300
gacgtgaact tcgcgaaccg gccgctgttc ccgtcgatgc ggctggcgtc cttcgacggc    360
gccatgctct ccgtgtccag ctacggcccg tactggcgca acctgcgccg cgtcgccgcc    420
gtgcagctcc tctccgcgca ccgcgtcggg tgcatggccc cgccatcga agcgcaggtg     480 cgcgccatgg tgcggaggat ggaccgcgcc gccgcggccg gcggcggcgg cgtcgcgcgc    540
gtccagctca gcggcggct gttcgagctc tccctcagcg tgctcatgga gaccatcgcg    600
cacaccaaga cgtcccgcgc cgaggccgac gccgactcgg acatgtcgac cgaggcccac    660
gagttcaagc agatcgtcga cgagctcgtg ccgtacatcg gcacggccaa ccgctgggac    720
tacctgccgg tgctgcgctg gttcgacgtg ttcggcgtga ggaacaagat cctcgacgcc    780
gtgggcagaa gggacgcgtt cctggggcgg ctcatcgacg gggagcggcg gaggctggac    840
gctggcgacg agagcgaaag taagagcatg attgcggtgc tgctcactct gcagaagtcc    900
gagccagagg tctacactga cactgtgatc actgctcttt gcgcggtgag tgcttcttct    960
tctaccatac gtcactctct tatcctcaca aaatacaaaa aaagttgccc gttttctcag   1020
tttagtcgtc aacactccgg actctactat ccgccaaagt ataggattcg ctaa         1074

<210> SEQ ID NO 27
<211> LENGTH: 2320
<212> TYPE: PRT
<213> ORGANISM: Alopecurus myosuroides

<400> SEQUENCE: 27

Met Gly Ser Thr His Leu Pro Ile Val Gly Phe Asn Ala Ser Thr Thr
1               5                   10                  15

Pro Ser Leu Ser Thr Leu Arg Gln Ile Asn Ser Ala Ala Ala Ala Phe
            20                  25                  30

Gln Ser Ser Ser Pro Ser Arg Ser Lys Lys Ser Arg Arg Val
        35                  40                  45

Lys Ser Ile Arg Asp Asp Gly Asp Gly Ser Val Pro Asp Pro Ala Gly
    50                  55                  60

His Gly Gln Ser Ile Arg Gln Gly Leu Ala Gly Ile Ile Asp Leu Pro
65                  70                  75                  80

Lys Glu Gly Ala Ser Ala Pro Asp Val Asp Ile Ser His Gly Ser Glu
                85                  90                  95
```

```
Asp His Lys Ala Ser Tyr Gln Met Asn Gly Ile Leu Asn Glu Ser His
            100                 105                 110

Asn Gly Arg His Ala Ser Leu Ser Lys Val Tyr Glu Phe Cys Thr Glu
            115                 120                 125

Leu Gly Gly Lys Thr Pro Ile His Ser Val Leu Val Ala Asn Asn Gly
        130                 135                 140

Met Ala Ala Ala Lys Phe Met Arg Ser Val Arg Thr Trp Ala Asn Asp
145                 150                 155                 160

Thr Phe Gly Ser Glu Lys Ala Ile Gln Leu Ile Ala Met Ala Thr Pro
                165                 170                 175

Glu Asp Met Arg Ile Asn Ala Glu His Ile Arg Ile Ala Asp Gln Phe
            180                 185                 190

Val Glu Val Pro Gly Gly Thr Asn Asn Asn Tyr Ala Asn Val Gln
            195                 200                 205

Leu Ile Val Glu Ile Ala Glu Arg Thr Gly Val Ser Ala Val Trp Pro
        210                 215                 220

Gly Trp Gly His Ala Ser Glu Asn Pro Glu Leu Pro Asp Ala Leu Thr
225                 230                 235                 240

Ala Lys Gly Ile Val Phe Leu Gly Pro Pro Ala Ser Ser Met Asn Ala
                245                 250                 255

Leu Gly Asp Lys Val Gly Ser Ala Leu Ile Ala Gln Ala Ala Gly Val
            260                 265                 270

Pro Thr Leu Ala Trp Ser Gly Ser His Val Glu Ile Pro Leu Glu Leu
        275                 280                 285

Cys Leu Asp Ser Ile Pro Glu Glu Met Tyr Arg Lys Ala Cys Val Thr
290                 295                 300

Thr Ala Asp Glu Ala Val Ala Ser Cys Gln Met Ile Gly Tyr Pro Ala
305                 310                 315                 320

Met Ile Lys Ala Ser Trp Gly Gly Gly Gly Lys Gly Ile Arg Lys Val
                325                 330                 335

Asn Asn Asp Asp Glu Val Lys Ala Leu Phe Lys Gln Val Gln Gly Glu
            340                 345                 350

Val Pro Gly Ser Pro Ile Phe Ile Met Arg Leu Ala Ser Gln Ser Arg
        355                 360                 365

His Leu Glu Val Gln Leu Leu Cys Asp Glu Tyr Gly Asn Val Ala Ala
370                 375                 380

Leu His Ser Arg Asp Cys Ser Val Gln Arg Arg His Gln Lys Ile Ile
385                 390                 395                 400

Glu Glu Gly Pro Val Thr Val Ala Pro Arg Glu Thr Val Lys Glu Leu
                405                 410                 415

Glu Gln Ala Ala Arg Arg Leu Ala Lys Ala Val Gly Tyr Val Gly Ala
            420                 425                 430

Ala Thr Val Glu Tyr Leu Tyr Ser Met Glu Thr Gly Glu Tyr Tyr Phe
        435                 440                 445

Leu Glu Leu Asn Pro Arg Leu Gln Val Glu His Pro Val Thr Glu Ser
    450                 455                 460

Ile Ala Glu Val Asn Leu Pro Ala Ala Gln Val Ala Val Gly Met Gly
465                 470                 475                 480

Ile Pro Leu Trp Gln Ile Pro Glu Ile Arg Arg Phe Tyr Gly Met Asp
                485                 490                 495

Asn Gly Gly Gly Tyr Asp Ile Trp Arg Lys Thr Ala Ala Leu Ala Thr
            500                 505                 510
```

-continued

```
Pro Phe Asn Phe Asp Glu Val Asp Ser Gln Trp Pro Lys Gly His Cys
            515                 520                 525

Val Ala Val Arg Ile Thr Ser Glu Asn Pro Asp Asp Gly Phe Lys Pro
530                 535                 540

Thr Gly Gly Lys Val Lys Glu Ile Ser Phe Lys Ser Lys Pro Asn Val
545                 550                 555                 560

Trp Gly Tyr Phe Ser Val Lys Ser Gly Gly Ile His Glu Phe Ala
                565                 570                 575

Asp Ser Gln Phe Gly His Val Phe Ala Tyr Gly Glu Thr Arg Ser Ala
            580                 585                 590

Ala Ile Thr Ser Met Ser Leu Ala Leu Lys Glu Ile Gln Ile Arg Gly
            595                 600                 605

Glu Ile His Thr Asn Val Asp Tyr Thr Val Asp Leu Leu Asn Ala Pro
            610                 615                 620

Asp Phe Arg Glu Asn Thr Ile His Thr Gly Trp Leu Asp Thr Arg Ile
625                 630                 635                 640

Ala Met Arg Val Gln Ala Glu Arg Pro Pro Trp Tyr Ile Ser Val Val
                645                 650                 655

Gly Gly Ala Leu Tyr Lys Thr Ile Thr Thr Asn Ala Glu Thr Val Ser
                660                 665                 670

Glu Tyr Val Ser Tyr Leu Ile Lys Gly Gln Ile Pro Pro Lys His Ile
            675                 680                 685

Ser Leu Val His Ser Thr Ile Ser Leu Asn Ile Glu Ser Lys Tyr
            690                 695                 700

Thr Ile Glu Ile Val Arg Ser Gly Gln Gly Ser Tyr Arg Leu Arg Leu
705                 710                 715                 720

Asn Gly Ser Leu Ile Glu Ala Asn Val Gln Thr Leu Cys Asp Gly Gly
                725                 730                 735

Leu Leu Met Gln Leu Asp Gly Asn Ser His Val Ile Tyr Ala Glu Glu
                740                 745                 750

Glu Ala Gly Gly Thr Arg Leu Leu Ile Asp Gly Lys Thr Cys Leu Leu
            755                 760                 765

Gln Asn Asp His Asp Pro Ser Arg Leu Leu Ala Glu Thr Pro Cys Lys
770                 775                 780

Leu Leu Arg Phe Leu Ile Ala Asp Gly Ala His Val Asp Ala Asp Val
785                 790                 795                 800

Pro Tyr Ala Glu Val Glu Val Met Lys Met Cys Met Pro Leu Leu Ser
                805                 810                 815

Pro Ala Ala Gly Val Ile Asn Val Leu Leu Ser Glu Gly Gln Ala Met
                820                 825                 830

Gln Ala Gly Asp Leu Ile Ala Arg Leu Asp Leu Asp Asp Pro Ser Ala
            835                 840                 845

Val Lys Arg Ala Glu Pro Phe Glu Gly Ser Phe Pro Glu Met Ser Leu
850                 855                 860

Pro Ile Ala Ala Ser Gly Gln Val His Lys Arg Cys Ala Ala Ser Leu
865                 870                 875                 880

Asn Ala Ala Arg Met Val Leu Ala Gly Tyr Asp His Ala Ala Asn Lys
                885                 890                 895

Val Val Gln Asp Leu Val Trp Cys Leu Asp Thr Pro Ala Leu Pro Phe
            900                 905                 910

Leu Gln Trp Glu Glu Leu Met Ser Val Leu Ala Thr Arg Leu Pro Arg
            915                 920                 925
```

```
Arg Leu Lys Ser Glu Leu Glu Gly Lys Tyr Asn Glu Tyr Lys Leu Asn
930                 935                 940

Val Asp His Val Lys Ile Lys Asp Phe Pro Thr Glu Met Leu Arg Glu
945                 950                 955                 960

Thr Ile Glu Glu Asn Leu Ala Cys Val Ser Glu Lys Glu Met Val Thr
                965                 970                 975

Ile Glu Arg Leu Val Asp Pro Leu Met Ser Leu Leu Lys Ser Tyr Glu
            980                 985                 990

Gly Gly Arg Glu Ser His Ala His Phe Ile Val Lys Ser Leu Phe Glu
        995                 1000                1005

Glu Tyr Leu Ser Val Glu Leu Phe Ser Asp Gly Ile Gln Ser
1010                1015                1020

Asp Val Ile Glu Arg Leu Arg Leu Gln Tyr Ser Lys Asp Leu Gln
1025                1030                1035

Lys Val Val Asp Ile Val Leu Ser His Gln Gly Val Arg Asn Lys
1040                1045                1050

Thr Lys Leu Ile Leu Ala Leu Met Glu Lys Leu Val Tyr Pro Asn
1055                1060                1065

Pro Ala Ala Tyr Arg Asp Gln Leu Ile Arg Phe Ser Ser Leu Asn
1070                1075                1080

His Lys Arg Tyr Tyr Lys Leu Ala Leu Lys Ala Ser Glu Leu Leu
1085                1090                1095

Glu Gln Thr Lys Leu Ser Glu Leu Arg Thr Ser Ile Ala Arg Asn
1100                1105                1110

Leu Ser Ala Leu Asp Met Phe Thr Glu Glu Lys Ala Asp Phe Ser
1115                1120                1125

Leu Gln Asp Arg Lys Leu Ala Ile Asn Glu Ser Met Gly Asp Leu
1130                1135                1140

Val Thr Ala Pro Leu Pro Val Glu Asp Ala Leu Val Ser Leu Phe
1145                1150                1155

Asp Cys Thr Asp Gln Thr Leu Gln Gln Arg Val Ile Gln Thr Tyr
1160                1165                1170

Ile Ser Arg Leu Tyr Gln Pro Gln Leu Val Lys Asp Ser Ile Gln
1175                1180                1185

Leu Lys Tyr Gln Asp Ser Gly Val Ile Ala Leu Trp Glu Phe Thr
1190                1195                1200

Glu Gly Asn His Glu Lys Arg Leu Gly Ala Met Val Ile Leu Lys
1205                1210                1215

Ser Leu Glu Ser Val Ser Thr Ala Ile Gly Ala Ala Leu Lys Asp
1220                1225                1230

Ala Ser His Tyr Ala Ser Ser Ala Gly Asn Thr Val His Ile Ala
1235                1240                1245

Leu Leu Asp Ala Asp Thr Gln Leu Asn Thr Thr Glu Asp Ser Gly
1250                1255                1260

Asp Asn Asp Gln Ala Gln Asp Lys Met Asp Lys Leu Ser Phe Val
1265                1270                1275

Leu Lys Gln Asp Val Val Met Ala Asp Leu Arg Ala Ala Asp Val
1280                1285                1290

Lys Val Val Ser Cys Ile Val Gln Arg Asp Gly Ala Ile Met Pro
1295                1300                1305

Met Arg Arg Thr Phe Leu Leu Ser Glu Glu Lys Leu Cys Tyr Glu
1310                1315                1320
```

-continued

```
Glu Glu Pro Ile Leu Arg His Val Glu Pro Pro Leu Ser Ala Leu
1325                1330                1335

Leu Glu Leu Asp Lys Leu Lys Val Lys Gly Tyr Asn Glu Met Lys
1340                1345                1350

Tyr Thr Pro Ser Arg Asp Arg Gln Trp His Ile Tyr Thr Leu Arg
1355                1360                1365

Asn Thr Glu Asn Pro Lys Met Leu His Arg Val Phe Phe Arg Thr
1370                1375                1380

Leu Val Arg Gln Pro Ser Ala Gly Asn Arg Phe Thr Ser Asp His
1385                1390                1395

Ile Thr Asp Val Glu Val Gly His Ala Glu Glu Pro Leu Ser Phe
1400                1405                1410

Thr Ser Ser Ser Ile Leu Lys Ser Leu Lys Ile Ala Lys Glu Glu
1415                1420                1425

Leu Glu Leu His Ala Ile Arg Thr Gly His Ser His Met Tyr Leu
1430                1435                1440

Cys Ile Leu Lys Glu Gln Lys Leu Leu Asp Leu Val Pro Val Ser
1445                1450                1455

Gly Asn Thr Val Val Asp Val Gly Gln Asp Glu Ala Thr Ala Cys
1460                1465                1470

Ser Leu Leu Lys Glu Met Ala Leu Lys Ile His Glu Leu Val Gly
1475                1480                1485

Ala Arg Met His His Leu Ser Val Cys Gln Trp Glu Val Lys Leu
1490                1495                1500

Lys Leu Val Ser Asp Gly Pro Ala Ser Gly Ser Trp Arg Val Val
1505                1510                1515

Thr Thr Asn Val Thr Gly His Thr Cys Thr Val Asp Ile Tyr Arg
1520                1525                1530

Glu Val Glu Asp Thr Glu Ser Gln Lys Leu Val Tyr His Ser Thr
1535                1540                1545

Ala Leu Ser Ser Gly Pro Leu His Gly Val Ala Leu Asn Thr Ser
1550                1555                1560

Tyr Gln Pro Leu Ser Val Ile Asp Leu Lys Arg Cys Ser Ala Arg
1565                1570                1575

Asn Asn Lys Thr Thr Tyr Cys Tyr Asp Phe Pro Leu Thr Phe Glu
1580                1585                1590

Ala Ala Val Gln Lys Ser Trp Ser Asn Ile Ser Ser Glu Asn Asn
1595                1600                1605

Gln Cys Tyr Val Lys Ala Thr Glu Leu Val Phe Ala Glu Lys Asn
1610                1615                1620

Gly Ser Trp Gly Thr Pro Ile Ile Pro Met Gln Arg Ala Ala Gly
1625                1630                1635

Leu Asn Asp Ile Gly Met Val Ala Trp Ile Leu Asp Met Ser Thr
1640                1645                1650

Pro Glu Phe Pro Ser Gly Arg Gln Ile Ile Val Ile Ala Asn Asp
1655                1660                1665

Ile Thr Phe Arg Ala Gly Ser Phe Gly Pro Arg Glu Asp Ala Phe
1670                1675                1680

Phe Glu Ala Val Thr Asn Leu Ala Cys Glu Lys Lys Leu Pro Leu
1685                1690                1695

Ile Tyr Leu Ala Ala Asn Ser Gly Ala Arg Ile Gly Ile Ala Asp
1700                1705                1710
```

```
Glu Val Lys Ser Cys Phe Arg Val Gly Trp Thr Asp Asp Ser Ser
1715                1720                1725

Pro Glu Arg Gly Phe Arg Tyr Ile Tyr Met Thr Asp Glu Asp His
1730                1735                1740

Asp Arg Ile Gly Ser Ser Val Ile Ala His Lys Met Gln Leu Asp
1745                1750                1755

Ser Gly Glu Ile Arg Trp Val Ile Asp Ser Val Val Gly Lys Glu
1760                1765                1770

Asp Gly Leu Gly Val Glu Asn Ile His Gly Ser Ala Ala Ile Ala
1775                1780                1785

Ser Ala Tyr Ser Arg Ala Tyr Glu Glu Thr Phe Thr Leu Thr Phe
1790                1795                1800

Val Thr Gly Arg Thr Val Gly Ile Gly Ala Tyr Leu Ala Arg Leu
1805                1810                1815

Gly Ile Arg Cys Ile Gln Arg Ile Asp Gln Pro Ile Ile Leu Thr
1820                1825                1830

Gly Phe Ser Ala Leu Asn Lys Leu Leu Gly Arg Glu Val Tyr Ser
1835                1840                1845

Ser His Met Gln Leu Gly Gly Pro Lys Ile Met Ala Thr Asn Gly
1850                1855                1860

Val Val His Leu Thr Val Pro Asp Asp Leu Glu Gly Val Ser Asn
1865                1870                1875

Ile Leu Arg Trp Leu Ser Tyr Val Pro Ala Asn Ile Gly Gly Pro
1880                1885                1890

Leu Pro Ile Thr Lys Ser Leu Asp Pro Ile Asp Arg Pro Val Ala
1895                1900                1905

Tyr Ile Pro Glu Asn Thr Cys Asp Pro Arg Ala Ala Ile Ser Gly
1910                1915                1920

Ile Asp Asp Ser Gln Gly Lys Trp Leu Gly Gly Met Phe Asp Lys
1925                1930                1935

Asp Ser Phe Val Glu Thr Phe Glu Gly Trp Ala Lys Thr Val Val
1940                1945                1950

Thr Gly Arg Ala Lys Leu Gly Gly Ile Pro Val Gly Val Ile Ala
1955                1960                1965

Val Glu Thr Gln Thr Met Met Gln Leu Val Pro Ala Asp Pro Gly
1970                1975                1980

Gln Pro Asp Ser His Glu Arg Ser Val Pro Arg Ala Gly Gln Val
1985                1990                1995

Trp Phe Pro Asp Ser Ala Thr Lys Thr Ala Gln Ala Met Leu Asp
2000                2005                2010

Phe Asn Arg Glu Gly Leu Pro Leu Phe Ile Leu Ala Asn Trp Arg
2015                2020                2025

Gly Phe Ser Gly Gly Gln Arg Asp Leu Phe Glu Gly Ile Leu Gln
2030                2035                2040

Ala Gly Ser Thr Ile Val Glu Asn Leu Arg Thr Tyr Asn Gln Pro
2045                2050                2055

Ala Phe Val Tyr Ile Pro Lys Ala Ala Glu Leu Arg Gly Gly Ala
2060                2065                2070

Trp Val Val Ile Asp Ser Lys Ile Asn Pro Asp Arg Ile Glu Cys
2075                2080                2085

Tyr Ala Glu Arg Thr Ala Lys Gly Asn Val Leu Glu Pro Gln Gly
2090                2095                2100
```

| | | | | | | | | | | | |
|---|---|---|---|---|---|---|---|---|---|---|---|
|Leu|Ile|Glu|Ile|Lys|Phe|Arg|Ser|Glu|Glu|Leu|Lys|Glu|Cys|Met|
| |2105| | | |2110| | | |2115| | | | | |

Leu Ile Glu Ile Lys Phe Arg Ser Glu Glu Leu Lys Glu Cys Met
    2105            2110              2115

Gly Arg Leu Asp Pro Glu Leu Ile Asp Leu Lys Ala Arg Leu Gln
    2120            2125            2130

Gly Ala Asn Gly Ser Leu Ser Asp Gly Glu Ser Leu Gln Lys Ser
    2135            2140            2145

Ile Glu Ala Arg Lys Lys Gln Leu Leu Pro Leu Tyr Thr Gln Ile
    2150            2155            2160

Ala Val Arg Phe Ala Glu Leu His Asp Thr Ser Leu Arg Met Ala
    2165            2170            2175

Ala Lys Gly Val Ile Arg Lys Val Val Asp Trp Glu Asp Ser Arg
    2180            2185            2190

Ser Phe Phe Tyr Lys Arg Leu Arg Arg Arg Leu Ser Glu Asp Val
    2195            2200            2205

Leu Ala Lys Glu Ile Arg Gly Val Ile Gly Glu Lys Phe Pro His
    2210            2215            2220

Lys Ser Ala Ile Glu Leu Ile Lys Lys Trp Tyr Leu Ala Ser Glu
    2225            2230            2235

Ala Ala Ala Ala Gly Ser Thr Asp Trp Asp Asp Asp Ala Phe
    2240            2245            2250

Val Ala Trp Arg Glu Asn Pro Glu Asn Tyr Lys Glu Tyr Ile Lys
    2255            2260            2265

Glu Leu Arg Ala Gln Arg Val Ser Arg Leu Leu Ser Asp Val Ala
    2270            2275            2280

Gly Ser Ser Ser Asp Leu Gln Ala Leu Pro Gln Gly Leu Ser Met
    2285            2290            2295

Leu Leu Asp Lys Met Asp Pro Ser Lys Arg Ala Gln Phe Ile Glu
    2300            2305            2310

Glu Val Met Lys Val Leu Lys
    2315            2320

<210> SEQ ID NO 28
<211> LENGTH: 1542
<212> TYPE: DNA
<213> ORGANISM: Oryza sativa

<400> SEQUENCE: 28

```
atggataacg cctacattat tgccattctc tctgtagcta tcctcttctt gctccactac      60
tacctcctcg gccgcggcaa tggcggggcg gcgcggctgc cgccgggtcc accggccgtc     120
ccgatcctgg acacctcca cctcgtcaag aagccgatgc acgccaccat gtcccgcctc     180
gccgagcggt acgggccggt gttctcgctg cgcctcgggt cgcggcgtgc cgtggtggtg     240
tcgtcgccgg ggtgcgccag ggagtgcttc accgagcacg acgtgacctt cgcgaaccgg     300
cccaggttcg agtcgcagct gctggtctcg ttcaacggcg ccgcgctcgc cacggcgagc     360
tacggcgcgc actggcgcaa cctccgccgg atcgtcgccg tgcagctgct ctccgcgcac     420
cgcgtcggcc tcatgtcggg gctcatcgcc ggcgaggtcc gcgccatggt gcggaggatg     480
taccgcgccg cggccgcgtc ccccgccggc gccgcgcgca tccagctgaa gcggaggctg     540
ttcgaggtct ccctcagcgt gctcatggag accatcgccc acaccaaggc gacccgcccc     600
gagacggacc cggacaccga catgtccgtg aagcccagg agtttaagca ggtcgtcgac     660
gagatcatcc gcacatcgg cgcggccaac ctgtgggact acttgccggc gctccggtgg     720
ttcgacgtgt tcggcgtcag gaggaagatc ctcgccgctg taagccggag ggacgcgttc     780
```

-continued

```
cttcgccgcc tgatcgacgc ggagcggcgg aggctggacg acggcgacga gggcgagaag    840
aagagcatga tcgccgtgct gctcactctg cagaagacag agccggaggt gtacaccgat    900
aacatgatca cagctctaac ggcgaacttg ttcggagcag aacagagac aacctcgacg    960 acatcagaat gggcgatgtc gctactgctg aaccaccccg acacactcaa gaaagcgcaa   1020
gccgagatcg acgcatccgt cggcaactct cgcctgatca ccgccgacga cgtgactcgc   1080
ctcggctacc tccagtgcat cgtcagggag acgctccgcc tgtacccgc cgcgccgatg    1140 ctcctcccgc acgagtcctc cgccgactgc aaggtcggcg gctacaacat cccgcgcggg   1200
tcgatgttgc tcatcaacgc gtacgccatc accgtgacc cggcggtgtg ggaggagccg    1260
gagaagttca tgccggagag gttcgaggac ggcgggtgcg acggcaatct cttgatgccg    1320
ttcgggatgg ggaggcggag gtgccccggc gagacgctgg cgctgcgcac agtggggttg    1380
gtgctgggca cgctgatcca gtgcttcgac tgggagaggg tcgacggcgt ggaggtcgac   1440
atgactgaag gtggcgggct caccatcccc aaggtcgtgc cgttggaggc catgtgcagg   1500
ccgcgcgacg ccatgggtgg tgttcttcgc gagctcgtct ga                      1542
```

<210> SEQ ID NO 29
<211> LENGTH: 513
<212> TYPE: PRT
<213> ORGANISM: Oryza sativa

<400> SEQUENCE: 29

```
Met Asp Asn Ala Tyr Ile Ile Ala Ile Leu Ser Val Ala Ile Leu Phe
1               5                   10                  15

Leu Leu His Tyr Tyr Leu Leu Gly Arg Gly Asn Gly Gly Ala Ala Arg
            20                  25                  30

Leu Pro Pro Gly Pro Pro Ala Val Pro Ile Leu Gly His Leu His Leu
        35                  40                  45

Val Lys Lys Pro Met His Ala Thr Met Ser Arg Leu Ala Glu Arg Tyr
    50                  55                  60

Gly Pro Val Phe Ser Leu Arg Leu Gly Ser Arg Arg Ala Val Val Val
65                  70                  75                  80

Ser Ser Pro Gly Cys Ala Arg Glu Cys Phe Thr Glu His Asp Val Thr
                85                  90                  95

Phe Ala Asn Arg Pro Arg Phe Glu Ser Gln Leu Leu Val Ser Phe Asn
            100                 105                 110

Gly Ala Ala Leu Ala Thr Ala Ser Tyr Gly Ala His Trp Arg Asn Leu
        115                 120                 125

Arg Arg Ile Val Ala Val Gln Leu Leu Ser Ala His Arg Val Gly Leu
    130                 135                 140

Met Ser Gly Leu Ile Ala Gly Glu Val Arg Ala Met Val Arg Arg Met
145                 150                 155                 160

Tyr Arg Ala Ala Ala Ser Pro Ala Gly Ala Arg Ile Gln Leu
                165                 170                 175

Lys Arg Arg Leu Phe Glu Val Ser Leu Ser Val Leu Met Glu Thr Ile
            180                 185                 190

Ala His Thr Lys Ala Thr Arg Pro Glu Thr Asp Pro Asp Thr Asp Met
        195                 200                 205

Ser Val Glu Ala Gln Glu Phe Lys Gln Val Val Asp Glu Ile Ile Pro
    210                 215                 220

His Ile Gly Ala Ala Asn Leu Trp Asp Tyr Leu Pro Ala Leu Arg Trp
225                 230                 235                 240
```

Phe Asp Val Phe Gly Val Arg Arg Lys Ile Leu Ala Ala Val Ser Arg
                245                 250                 255

Arg Asp Ala Phe Leu Arg Arg Leu Ile Asp Ala Glu Arg Arg Arg Leu
            260                 265                 270

Asp Asp Gly Asp Glu Gly Glu Lys Lys Ser Met Ile Ala Val Leu Leu
        275                 280                 285

Thr Leu Gln Lys Thr Glu Pro Glu Val Tyr Thr Asp Asn Met Ile Thr
    290                 295                 300

Ala Leu Thr Ala Asn Leu Phe Gly Ala Gly Thr Glu Thr Thr Ser Thr
305                 310                 315                 320

Thr Ser Glu Trp Ala Met Ser Leu Leu Leu Asn His Pro Asp Thr Leu
                325                 330                 335

Lys Lys Ala Gln Ala Glu Ile Asp Ala Ser Val Gly Asn Ser Arg Leu
            340                 345                 350

Ile Thr Ala Asp Asp Val Thr Arg Leu Gly Tyr Leu Gln Cys Ile Val
        355                 360                 365

Arg Glu Thr Leu Arg Leu Tyr Pro Ala Ala Pro Met Leu Leu Pro His
    370                 375                 380

Glu Ser Ser Ala Asp Cys Lys Val Gly Gly Tyr Asn Ile Pro Arg Gly
385                 390                 395                 400

Ser Met Leu Leu Ile Asn Ala Tyr Ala Ile His Arg Asp Pro Ala Val
                405                 410                 415

Trp Glu Glu Pro Glu Lys Phe Met Pro Glu Arg Phe Glu Asp Gly Gly
            420                 425                 430

Cys Asp Gly Asn Leu Leu Met Pro Phe Gly Met Gly Arg Arg Arg Cys
        435                 440                 445

Pro Gly Glu Thr Leu Ala Leu Arg Thr Val Gly Leu Val Leu Gly Thr
    450                 455                 460

Leu Ile Gln Cys Phe Asp Trp Glu Arg Val Asp Gly Val Glu Val Asp
465                 470                 475                 480

Met Thr Glu Gly Gly Gly Leu Thr Ile Pro Lys Val Val Pro Leu Glu
                485                 490                 495

Ala Met Cys Arg Pro Arg Asp Ala Met Gly Gly Val Leu Arg Glu Leu
            500                 505                 510

Val

<210> SEQ ID NO 30
<211> LENGTH: 2199
<212> TYPE: DNA
<213> ORGANISM: Oryza sativa

<400> SEQUENCE: 30
atggcgttct tgggatgggc ggtcgacatc gcccgcgact ccggcgcgtc gagctccgtc     60
gtgctcacct gcgacggcta cggctcggcg ctctacttct cgccgtggga cagtgtcccg    120
cttccggcga cagcttcccc cgacgacggc ttcctgctgc cgcgtttccc ggacgtctgc    180
gtgcagcgct cgcaattcac caaccacctc gcgccggcca acggcactgg cggcggcggc    240
tcaagaacgg cgtcaagga ggaagcgagc gaggtgttgt cctggccacc gacttcgaag    300
caatctgtgc gccggttgga ggtggcgag cactggtacc gactctacaa gacggacaat    360
caacggctgt ctcctgatag tcaacaggtc tcggtcctcg cagagtcgca ctgcgatttg    420
gcctctggaa actggaaaga gatctcgatc caccacaaga aaatgccaag cagcacgacg    480
acgaagacga caacgccttc cagagatgcc tggattgtct ccgcaagatc tgatccattt    540

| | |
|---|---|
| catctccttc tagaagcaca agcgccgctc ggtataaagg cagacgcatt gtcacaaata | 600 |
| gctgcagtgc accagagtca cagaaacaca tcacacattc gtgagctcag cttagccatg | 660 |
| gataacgcct acattattgc cattctctct gtagctatcc tcttcttgct ccactactac | 720 |
| ctcctcggcc gcggcaatgg cggggcggcg cggctgccgc cgggtccacc ggccgtcccg | 780 |
| atcctgggac acctccacct cgtcaagaag ccgatgcacg ccaccatgtc ccgcctcgcc | 840 |
| gagcggtacg ggccggtgtt ctcgctgcgc ctcgggtcgc ggcgtgccgt ggtggtgtcg | 900 |
| tcgccgggt gcgccaggga gtgcttcacc gagcacgacg tgaccttcgc gaaccggccc | 960 |
| aggttcgagt cgcagctgct ggtctcgttc aacggcgccg cgctcgccac ggcgagctac | 1020 |
| ggcgcgcact ggcgcaacct ccgccggatc gtcgccgtgc agctgctctc cgcgcaccgc | 1080 |
| gtcggcctca tgtcggggct catcgccggc gaggtccgcg ccatggtgcg gaggatgtac | 1140 |
| cgcgccgcgg ccgcgtcccc cgccggcgcc gcgcgcatcc agctgaagcg gaggctgttc | 1200 |
| gaggtctccc tcagcgtgct catggagacc atcgcccaca ccaaggcgac ccgccccgag | 1260 |
| acggacccgg acaccgacat gtccgtggaa gcccaggagt ttaagcaggt cgtcgacgag | 1320 |
| atcatcccgc acatcggcgc ggccaacctg tgggactact tgccggcgct ccggtggttc | 1380 |
| gacgtgttcg gcgtcaggag gaagatcctc gccgctgtaa gccggaggga cgcgttcctt | 1440 |
| cgccgcctga tcgacgcgga gcggcggagg ctggacgacg gcgacgaggg cgagaagaag | 1500 |
| agcatgatcg ccgtgctgct cactctgcag aagacagagc cggaggtgta caccgataac | 1560 |
| atgatcacag ctctaacggc gaacttgttc ggagcaggaa cagagacaac ctcgacgaca | 1620 |
| tcagaatggg cgatgtcgct actgctgaac caccccgaca cactcaagaa agcgcaagcc | 1680 |
| gagatcgacg catccgtcgg caactctcgc ctgatcaccg ccgacgacgt gactcgcctc | 1740 |
| ggctacctcc agtgcatcgt cagggagacg ctccgcctgt accccgccgc gccgatgctc | 1800 |
| ctcccgcacg agtcctccgc cgactgcaag gtcggcggct acaacatccc gcgcgggtcg | 1860 |
| atgttgctca tcaacgcgta cgccatccac cgtgacccgg cggtgtggga ggagccggag | 1920 |
| aagttcatgc cggagaggtt cgaggacggc gggtgcgacg gcaatctctt gatgccgttc | 1980 |
| gggatgggga ggcggaggtg ccccggcgag acgctggcgc tgcgcacagt ggggttggtg | 2040 |
| ctgggcacgc tgatccagtg cttcgactgg gagagggtcg acggcgtgga ggtcgacatg | 2100 |
| actgaaggtg gcgggctcac catccccaag gtcgtgccgt tggaggccat gtgcaggccg | 2160 |
| cgcgacgcca tgggtggtgt tcttcgcgag ctcgtctga | 2199 |

<210> SEQ ID NO 31
<211> LENGTH: 1569
<212> TYPE: DNA
<213> ORGANISM: Sorghum bicolor

<400> SEQUENCE: 31

| | |
|---|---|
| atggataagg cctatgtcgc cgttttatcc ttcgccttct tattcgtatt acattatttg | 60 |
| gttggaagag caggcggtaa tggtagaaaa ggtaataatg gaaaaggtaa tgccgctcaa | 120 |
| cagagattgc ctccaagtcc acctgccgtc cctttcttag acatttgca tttagtaaag | 180 |
| actccttttc atgaggcctt agcaggctta gcagctaggc atggcccagt attctctatg | 240 |
| agaatgggat caagaggagc tgttgttgta tcttcacctg agtgtgctaa ggaatgtttc | 300 |
| actgaacatg acgtggcttt cgctaataga ccaaggtttg caacccaaga attagtatcc | 360 |
| ttcggtggcg cagcattagc tactgccagt tatggcccat actggagaaa cttaaggaga | 420 |
| gtcgccgcag ttcaattgtt atcagcccac agagttgctt gtatgagttc agttatatca | 480 |

```
gctgaggtga gagctatggt tagaagaatg tcaagggctg ctgctgctgc tcccgatggt    540
gcagcaagag ttcagttaaa gaggagatta ttcgaggtct cattatcagt attaatggag    600
actattgctc aaacaaagac atctaggaca gaagcagatg ccgacaccga tatgtctcca    660
gaagcacatg aatttaagca aattgtagat gaaattgttc cacatttggg aactgctaat    720
ttgtgggact acttaccagt cttgcagtgg ttcgacgtct ttggagtgag aaacaaaatt    780
atggcagcag tctccaggag agatgctttc ttaagaaggt taatcgacgc agagagaaga    840
aggatggatg acggaggtga ttctgacaag aagtctatga tagctgtatt attgtctttg    900
cagaaatctg aaccagaatt gtataccgat actatgataa tggctttgtg cggtaattta    960
tttggagccg aactgaaac cacatcttct actactgagt gggccatgtc tttattgttg     1020
aatcaccctg aagccttgaa gaaagctcag gccgaaattg atgccgttgt cggtaacagt    1080
agattgatca ctgccgaaga cgttcctaga ttaggatatt tacaatgtgt tatcaacgaa    1140
actttgagaa tgtacccagc agcacctttg ttgttgccac acgagagtgc tgctgattgc    1200
aaggtaggtg gctacgatgt accaagaggc acattattaa tagttaacgc ttatgctatt    1260
cacagagatc cagcagtctg ggaggaccct gcagaattta gaccagaaag gtttgaagat    1320
ggtaaggctg aaggtagatt gttgatgcct tttggtatgg gtagaagaaa gtgccctggt    1380
gaaacattgg cattaaggac agtgggttta gttttaggta cattgattca atgtatcgac    1440
tgggatagag tggatggttt ggaaattgat atgacagctg gtggtggttt gaccatgcct    1500
agggctgtgc ccttggaagc tacctgtaaa cccagggcag ctatgaggga tgtgttgatg    1560
gaattgtaa                                                             1569
```

<210> SEQ ID NO 32
<211> LENGTH: 522
<212> TYPE: PRT
<213> ORGANISM: Sorghum bicolor

<400> SEQUENCE: 32

```
Met Asp Lys Ala Tyr Val Ala Val Leu Ser Phe Ala Phe Leu Phe Val
1               5                   10                  15

Leu His Tyr Leu Val Gly Arg Ala Gly Gly Asn Gly Arg Lys Gly Asn
            20                  25                  30

Asn Gly Lys Gly Asn Ala Ala Gln Gln Arg Leu Pro Pro Ser Pro Pro
        35                  40                  45

Ala Val Pro Phe Leu Gly His Leu His Leu Val Lys Thr Pro Phe His
    50                  55                  60

Glu Ala Leu Ala Gly Leu Ala Ala Arg His Gly Pro Val Phe Ser Met
65                  70                  75                  80

Arg Met Gly Ser Arg Gly Ala Val Val Ser Ser Pro Glu Cys Ala
                85                  90                  95

Lys Glu Cys Phe Thr Glu His Asp Val Ala Phe Ala Asn Arg Pro Arg
            100                 105                 110

Phe Ala Thr Gln Glu Leu Val Ser Phe Gly Gly Ala Ala Leu Ala Thr
        115                 120                 125

Ala Ser Tyr Gly Pro Tyr Trp Arg Asn Leu Arg Val Ala Ala Val
    130                 135                 140

Gln Leu Leu Ser Ala His Arg Val Ala Cys Met Ser Ser Val Ile Ser
145                 150                 155                 160

Ala Glu Val Arg Ala Met Val Arg Arg Met Ser Arg Ala Ala Ala Ala
                165                 170                 175
```

Ala Pro Asp Gly Ala Ala Arg Val Gln Leu Lys Arg Arg Leu Phe Glu
            180                 185                 190

Val Ser Leu Ser Val Leu Met Glu Thr Ile Ala Gln Thr Lys Thr Ser
        195                 200                 205

Arg Thr Glu Ala Asp Ala Asp Thr Asp Met Ser Pro Glu Ala His Glu
    210                 215                 220

Phe Lys Gln Ile Val Asp Glu Ile Val Pro His Leu Gly Thr Ala Asn
225                 230                 235                 240

Leu Trp Asp Tyr Leu Pro Val Leu Gln Trp Phe Asp Val Phe Gly Val
                245                 250                 255

Arg Asn Lys Ile Met Ala Val Ser Arg Arg Asp Ala Phe Leu Arg
            260                 265                 270

Arg Leu Ile Asp Ala Glu Arg Arg Met Asp Asp Gly Gly Asp Ser
        275                 280                 285

Asp Lys Lys Ser Met Ile Ala Val Leu Leu Ser Leu Gln Lys Ser Glu
    290                 295                 300

Pro Glu Leu Tyr Thr Asp Thr Met Ile Met Ala Leu Cys Gly Asn Leu
305                 310                 315                 320

Phe Gly Ala Gly Thr Glu Thr Thr Ser Ser Thr Thr Glu Trp Ala Met
                325                 330                 335

Ser Leu Leu Leu Asn His Pro Glu Ala Leu Lys Lys Ala Gln Ala Glu
            340                 345                 350

Ile Asp Ala Val Val Gly Asn Ser Arg Leu Ile Thr Ala Glu Asp Val
        355                 360                 365

Pro Arg Leu Gly Tyr Leu Gln Cys Val Ile Asn Glu Thr Leu Arg Met
    370                 375                 380

Tyr Pro Ala Ala Pro Leu Leu Leu Pro His Glu Ser Ala Ala Asp Cys
385                 390                 395                 400

Lys Val Gly Gly Tyr Asp Val Pro Arg Gly Thr Leu Leu Ile Val Asn
                405                 410                 415

Ala Tyr Ala Ile His Arg Asp Pro Ala Val Trp Glu Asp Pro Ala Glu
            420                 425                 430

Phe Arg Pro Glu Arg Phe Glu Asp Gly Lys Ala Glu Gly Arg Leu Leu
        435                 440                 445

Met Pro Phe Gly Met Gly Arg Arg Lys Cys Pro Gly Glu Thr Leu Ala
    450                 455                 460

Leu Arg Thr Val Gly Leu Val Leu Gly Thr Leu Ile Gln Cys Ile Asp
465                 470                 475                 480

Trp Asp Arg Val Asp Gly Leu Glu Ile Asp Met Thr Ala Gly Gly Gly
                485                 490                 495

Leu Thr Met Pro Arg Ala Val Pro Leu Glu Ala Thr Cys Lys Pro Arg
            500                 505                 510

Ala Ala Met Arg Asp Val Leu Met Glu Leu
        515                 520

<210> SEQ ID NO 33
<211> LENGTH: 1503
<212> TYPE: DNA
<213> ORGANISM: Oryza sativa

<400> SEQUENCE: 33
atggacgccc tcctcgtgga aaggtcctc ctgggcctgt tcgtggcggc ggtgctggcc     60
ctagtggtgg ccaagctcac cgggaagagg ctccgcctcc cgcccggccc cgccggcgct    120
cccatcgtcg gcaactggct ccaggtcggc gacgacctca accaccgcaa cctgatggcg    180

```
ctggcgcggc ggttcggcga catcctcctc ctccgcatgg gcgtccgcaa cctggtggtg      240
gtgtccagcc cggacctcgc caaggaggtg ctccacaccc agggcgtcga gttcggctcc      300
cgcacccgca acgtggtgtt cgacatcttc accgggaagg ggcaggacat ggtgttcacc      360
gtgtacggcg accactggcg caagatgcgg cggatcatga cggtgcccet cttcaccaac      420 aaggtggtgg cccagaaccg cgcgggttgg gaggaggagg cgaggctggt ggtggaggac      480
gtccgccgcg accccgccgc ggcgacctcc ggcgtggtga tccggcgaag gttgcagctg      540
atgatgtaca acgacatgtt ccgcatcatg ttcgaccgcc gtttcgacag cgtggacgac      600
ccgctcttca acaagctcaa ggccttcaac gcggagcgca gccgcctctc gcagagcttc      660
gagtacaact acggtgactt catccccgtc ctccgcccct cctccgccg ctacctcgca       720 cgctgccacc agctcaagtc ccagcgcatg aagctcttcg aggaccactt cgtccaggaa      780
cgcaagagag tgatggaaca gactggtgag atccggtgcg ccatggacca catcctcgag      840
gccgagagga agggcgagat caaccacgac aacgtcctct acatcgtcga aacatcaac       900 gttgctgcta tcgagacgac gctgtggtcg atcgaatggg gaatcgcgga gctggtgaac      960
cacccgagca tccagtcgaa ggtgcgggag gagatggcgt cggtgctggg cggcgcggcg      1020
gtgacggagc cggacctgga gcggctgccg taccttcagg cggtggtgaa ggagacgctg      1080
cggttgcgca tggcgatccc gctgctggtg ccgcacatga acctcgccga cggcaagctc      1140
gccggctacg acatccccgc cgagtccaag atcctggtga acgcgtggtt cctcgccaac      1200
gaccccaagc ggtgggtgcg ccccgacgag tttaggccgg agaggttcct ggaggaggag      1260
aaggccgtgg aggcgcacgg caacgacttc cgcttcgtgc ccttcggcgt cggccgccgc      1320
agctgccccg ggatcatcct cgcgctgccc atcatcggga tcacgctcgg ccgcctcgtc      1380
cagagcttcg acctgctgcc gccgcccggg atggacaagg tggacaccac cgagaagccc      1440
ggccagttca gcaaccagat cctcaagcac gccaccgtcg tctgcaagcc catcgacgcc      1500
tag                                                                   1503

<210> SEQ ID NO 34
<211> LENGTH: 518
<212> TYPE: PRT
<213> ORGANISM: Oryza sativa

<400> SEQUENCE: 34

Met Val Lys Ala Tyr Ile Ala Ile Phe Ser Ile Ala Val Leu Leu Leu
1               5                   10                  15

Ile His Phe Leu Phe Arg Arg Arg Gly Arg Ser Asn Gly Met Pro Leu
            20                  25                  30

Pro Pro Ser Pro Pro Ala Ile Pro Phe Phe Gly His Leu His Leu Ile
        35                  40                  45

Asp Lys Pro Phe His Ala Ala Leu Ser Arg Leu Ala Glu Arg His Gly
    50                  55                  60

Pro Val Phe Ser Leu Arg Leu Gly Ser Arg Asn Ala Val Val Val Ser
65                  70                  75                  80

Ser Pro Glu Cys Ala Arg Glu Cys Phe Thr Asp Asn Asp Val Cys Phe
                85                  90                  95

Ala Asn Arg Pro Arg Phe Pro Ser Gln Met Leu Ala Thr Phe Asn Gly
            100                 105                 110

Thr Ser Leu Gly Ser Ala Asn Tyr Gly Pro His Trp Arg Asn Leu Arg
        115                 120                 125
```

```
Arg Ile Ala Thr Val His Leu Leu Ser Ser His Arg Val Ser Gly Met
        130                 135                 140
Ser Gly Ile Ile Ser Gly Gln Ala Arg His Met Val Arg Arg Met Tyr
145                 150                 155                 160
Arg Ala Ala Thr Ala Ser Ala Ala Gly Val Ala Arg Val Gln Leu Asn
                165                 170                 175
Arg Arg Leu Phe Glu Leu Ser Leu Ser Val Leu Met Glu Ala Ile Ala
            180                 185                 190
Gln Ser Lys Thr Thr Arg Arg Glu Ala Pro Asp Ala Asp Thr Asp Met
        195                 200                 205
Ser Met Glu Ala Gln Glu Leu Arg His Val Leu Asp Glu Leu Asn Pro
210                 215                 220
Leu Ile Gly Ala Ala Asn Leu Trp Asp Tyr Leu Pro Ala Leu Arg Trp
225                 230                 235                 240
Phe Asp Val Phe Gly Val Lys Arg Lys Ile Val Ala Ala Val Asn Arg
                245                 250                 255
Arg Asn Ala Phe Met Arg Arg Leu Ile Asp Ala Glu Arg Gln Arg Met
                260                 265                 270
Asp Asn Asn Asp Val Asp Gly Gly Asp Asp Gly Glu Lys Lys Ser Met
            275                 280                 285
Ile Ser Val Leu Leu Thr Leu Gln Lys Thr Gln Pro Glu Val Tyr Thr
        290                 295                 300
Asp Thr Leu Ile Met Thr Leu Cys Ala Pro Leu Phe Gly Ala Gly Thr
305                 310                 315                 320
Glu Thr Thr Ser Thr Thr Ile Glu Trp Ala Met Ser Leu Leu Leu Asn
                325                 330                 335
His Pro Glu Ile Leu Lys Lys Ala Gln Ala Glu Ile Asp Met Ser Val
            340                 345                 350
Gly Asn Ser Arg Leu Ile Ser Val Val Asp Val His Arg Leu Gly Tyr
        355                 360                 365
Leu Gln Cys Ile Ile Asn Glu Thr Leu Arg Met Tyr Pro Ala Ala Pro
370                 375                 380
Leu Leu Leu Pro His Glu Ser Ser Ala Asp Cys Lys Val Gly Gly Tyr
385                 390                 395                 400
His Ile Pro Ser Gly Ala Met Leu Leu Val Asn Val Ala Ala Ile Gln
                405                 410                 415
Arg Asp Pro Val Ile Trp Lys Glu Pro Ser Glu Phe Lys Pro Glu Arg
                420                 425                 430
Phe Glu Asn Gly Arg Phe Glu Gly Leu Phe Met Ile Pro Phe Gly Met
            435                 440                 445
Gly Arg Arg Arg Cys Pro Gly Glu Met Leu Ala Leu Gln Thr Ile Gly
        450                 455                 460
Leu Val Leu Gly Thr Met Ile Gln Cys Phe Asp Trp Gly Arg Val Asp
465                 470                 475                 480
Asp Ala Met Val Asp Met Thr Gln Ser Asn Gly Leu Thr Ser Leu Lys
                485                 490                 495
Val Ile Pro Leu Glu Ala Met Cys Lys Pro Arg Glu Ala Met Cys Asp
            500                 505                 510
Val Leu Arg Lys Phe Met
            515
```

```
<210> SEQ ID NO 35
<211> LENGTH: 474
<212> TYPE: PRT
<213> ORGANISM: Oryza sativa

<400> SEQUENCE: 35

Met Asp Lys Ala Tyr Ile Ala Val Phe Ser Ile Val Ile Leu Phe Leu
1               5                   10                  15

Leu Val Asp Tyr Leu Arg Arg Leu Arg Gly Gly Gly Thr Ser Asn Gly
            20                  25                  30

Lys Asn Lys Gly Met Arg Leu Pro Pro Gly Leu Pro Ala Val Pro Ile
        35                  40                  45

Ile Gly His Leu His Leu Val Lys Lys Pro Met His Ala Thr Leu Ser
    50                  55                  60

Arg Leu Ala Ala Arg His Gly Pro Val Phe Ser Leu Arg Leu Gly Ser
65                  70                  75                  80

Arg Arg Ala Val Val Val Ser Ser Pro Gly Cys Ala Arg Glu Cys Phe
                85                  90                  95

Thr Glu His Asp Val Ala Phe Ala Asn Arg Pro Arg Phe Glu Ser Gln
            100                 105                 110

Leu Leu Met Ser Phe Asp Gly Thr Ala Leu Ala Met Ala Ser Tyr Gly
        115                 120                 125

Pro His Trp Arg Asn Leu Arg Arg Val Ala Ala Val Gln Leu Leu Ser
    130                 135                 140

Ala Arg Arg Val Gly Leu Met Ser Gly Leu Ile Ala Gly Glu Ser Lys
145                 150                 155                 160

Ala Thr Arg Pro Glu Thr Thr Asp Thr Asp Thr Asp Met Ser Met Glu
                165                 170                 175

Ala Gln Glu Tyr Lys Gln Val Val Glu Glu Ile Leu Glu Arg Ile Gly
            180                 185                 190

Thr Gly Asn Leu Cys Asp Tyr Leu Pro Ala Leu Arg Trp Phe Asp Val
        195                 200                 205

Phe Gly Val Arg Asn Arg Ile Leu Ala Ala Val Ser Arg Arg Asp Ala
    210                 215                 220

Phe Leu Arg Arg Leu Ile Tyr Ala Ala Arg Trp Arg Met Asp Asp Gly
225                 230                 235                 240

Glu Lys Lys Ser Met Ile Ala Val Leu Leu Thr Leu Gln Lys Thr Gln
                245                 250                 255

Pro Glu Val Tyr Thr Asp Asn Met Ile Thr Ala Leu Cys Ser Asn Leu
            260                 265                 270

Leu Gly Ala Gly Thr Glu Thr Thr Ser Thr Thr Ile Glu Trp Ala Met
        275                 280                 285

Ser Leu Leu Leu Asn His Pro Glu Thr Leu Lys Lys Ala Gln Ala Glu
    290                 295                 300

Ile Asp Ala Ser Val Gly Asn Ser Arg Leu Ile Thr Ala Asp Val
305                 310                 315                 320

Pro Arg Ile Thr Tyr Leu Gln Cys Ile Val Arg Glu Thr Leu Arg Leu
                325                 330                 335

Tyr Pro Ala Ala Pro Met Leu Ile Pro His Glu Ser Ser Ala Asp Cys
            340                 345                 350

Glu Val Gly Gly Tyr Ser Val Pro Arg Gly Thr Met Leu Leu Val Asn
        355                 360                 365

Ala Tyr Ala Ile His Arg Asp Pro Ala Ala Trp Glu Glu Pro Glu Arg
    370                 375                 380
```

```
Phe Val Pro Glu Arg Phe Glu Gly Gly Cys Asp Gly Asn Leu Ser
385                 390                 395                 400

Met Pro Phe Gly Met Gly Arg Arg Cys Pro Gly Glu Thr Leu Ala
            405                 410                 415

Leu His Thr Val Gly Leu Val Leu Gly Thr Leu Ile Gln Cys Phe Asp
            420                 425                 430

Trp Glu Arg Val Asp Gly Val Glu Val Asp Met Ala Glu Gly Gly
        435                 440                 445

Leu Thr Met Pro Lys Val Val Pro Leu Glu Ala Val Cys Arg Pro Arg
    450                 455                 460

Asp Ala Met Gly Gly Val Leu Arg Glu Leu
465             470

<210> SEQ ID NO 36
<211> LENGTH: 527
<212> TYPE: PRT
<213> ORGANISM: Oryza sativa

<400> SEQUENCE: 36

Met Asp Lys Ala Tyr Ile Ala Val Phe Ser Ile Ala Ile Leu Phe Leu
1               5                   10                  15

Leu Val Asp Tyr Phe Arg Cys Arg Arg Arg Gly Ser Gly Ser Asn
            20                  25                  30

Asn Gly Glu Asn Lys Gly Met Leu Gln Leu Pro Pro Ser Pro Pro Ala
        35                  40                  45

Ile Pro Phe Phe Gly His Leu His Leu Ile Asp Lys Pro Leu His Ala
    50                  55                  60

Ala Leu Ser Arg Leu Ala Glu Arg His Gly Pro Val Phe Ser Leu Arg
65              70                  75                  80

Leu Gly Ser Arg Asn Ala Val Val Val Ser Ser Pro Glu Cys Ala Arg
            85                  90                  95

Glu Cys Phe Thr Asp Asn Asp Val Cys Phe Ala Asn Arg Pro Gln Phe
            100                 105                 110

Pro Ser Gln Met Pro Ala Thr Phe Tyr Gly Ala Gly Phe Gly Phe Ala
        115                 120                 125

Asn Tyr Gly Ala His Trp Arg Asn Leu Arg Arg Ile Ala Thr Val His
    130                 135                 140

Leu Leu Ser Ala His Arg Val Arg Gly Met Ala Gly Val Val Ser Gly
145             150                 155                 160

Glu Ile Arg Pro Met Val Gln Arg Met Tyr Arg Ala Ala Ala Ala
            165                 170                 175

Gly Val Gly Val Ala Arg Val Gln Leu Lys Arg Leu Phe Glu Leu
        180                 185                 190

Ser Leu Ser Val Leu Met Glu Ala Ile Ala Gln Thr Lys Thr Thr Arg
    195                 200                 205

Pro Glu Ala Asp Asp Ala Asp Thr Asp Met Ser Val Glu Ala Gln Glu
    210                 215                 220

Phe Lys Asn Val Leu Asp Glu Leu Asn Pro Leu Leu Gly Ala Ala Asn
225                 230                 235                 240

Leu Trp Asp Tyr Leu Pro Ala Leu Arg Val Phe Asp Val Leu Gly Val
            245                 250                 255

Lys Arg Lys Ile Ala Thr Leu Ala Asn Arg Arg Asp Ala Phe Val Arg
        260                 265                 270

Arg Leu Ile Asp Ala Glu Arg Gln Arg Met Asp Asn Gly Val Asp Gly
    275                 280                 285
```

```
Gly Asp Asp Gly Glu Lys Lys Ser Val Ile Ser Val Leu Leu Ser Leu
    290                 295                 300

Gln Lys Thr Glu Pro Glu Val Tyr Lys Asp Ile Val Ile Val Asn Leu
305                 310                 315                 320

Cys Ala Ala Leu Phe Ala Ala Gly Thr Glu Thr Thr Ala Met Thr Ile
                325                 330                 335

Glu Trp Ala Met Ser Leu Leu Leu Asn His Pro Lys Ile Leu Lys Lys
                340                 345                 350

Ala Lys Ala Glu Ile Asp Ala Ser Val Gly Asn Ser Arg Leu Ile Asn
            355                 360                 365

Gly Asp Asp Met Pro His Leu Ser Tyr Leu Gln Cys Ile Ile Asn Glu
370                 375                 380

Thr Leu Arg Leu Tyr Pro Val Ala Pro Leu Leu Ile Pro His Glu Ser
385                 390                 395                 400

Ser Ala Asp Cys Lys Val Asn Gly Tyr His Ile Pro Ser Gly Thr Met
                405                 410                 415

Leu Leu Val Asn Val Ile Ala Ile Gln Arg Asp Pro Met Val Trp Lys
                420                 425                 430

Glu Pro Asn Glu Phe Lys Pro Glu Arg Phe Glu Asn Gly Glu Ser Glu
                435                 440                 445

Gly Leu Phe Met Ile Pro Phe Gly Met Gly Arg Arg Lys Cys Pro Gly
        450                 455                 460

Glu Thr Met Ala Leu Gln Thr Ile Gly Leu Val Leu Gly Ala Leu Ile
465                 470                 475                 480

Gln Cys Phe Asp Trp Asp Arg Val Asp Gly Ala Glu Val Asp Met Thr
                485                 490                 495

Gln Gly Ser Gly Leu Thr Asn Pro Arg Ala Val Pro Leu Glu Ala Met
            500                 505                 510

Cys Lys Pro Arg Glu Ala Met Ser Asp Val Phe Arg Glu Leu Leu
                515                 520                 525

<210> SEQ ID NO 37
<211> LENGTH: 520
<212> TYPE: PRT
<213> ORGANISM: Oryza sativa

<400> SEQUENCE: 37

Met Lys Tyr Ser Thr Ser Val Thr Met Asp Lys Ala Tyr Ile Ala Val
1               5                   10                  15

Phe Ser Ile Val Ile Leu Phe Leu Val Asp Tyr Leu Arg Arg Leu
                20                  25                  30

Arg Gly Gly Gly Thr Ser Asn Gly Lys Asn Lys Gly Met Arg Leu Pro
            35                  40                  45

Pro Gly Leu Pro Ala Val Pro Ile Ile Gly His Leu His Leu Val Lys
        50                  55                  60

Lys Pro Met His Ala Thr Leu Ser Arg Leu Ala Ala Arg His Gly Pro
65                  70                  75                  80

Val Phe Ser Leu Arg Leu Gly Ser Arg Ala Val Val Val Ser Ser
                85                  90                  95

Pro Gly Cys Ala Arg Glu Cys Phe Thr Glu His Asp Val Ala Phe Ala
                100                 105                 110

Asn Arg Pro Arg Phe Glu Ser Gln Leu Leu Met Ser Phe Asp Gly Thr
            115                 120                 125

Ala Leu Ala Met Ala Ser Tyr Gly Pro His Trp Arg Asn Leu Arg Arg
130                 135                 140
```

```
Val Ala Ala Val Gln Leu Leu Ser Ala Arg Arg Val Gly Leu Met Ser
145                 150                 155                 160

Gly Leu Ile Ala Gly Glu Val Arg Ala Met Val Arg Ser Leu Cys Arg
            165                 170                 175

Arg Pro Ala Ala Ala Pro Val Gln Leu Lys Arg Arg Leu Phe Glu
        180                 185                 190

Leu Ser Leu Ser Val Leu Met Glu Thr Ile Ala Gln Ser Lys Ala Thr
        195                 200                 205

Arg Pro Glu Thr Thr Asp Thr Asp Thr Asp Met Ser Met Glu Ala Gln
210                 215                 220

Glu Tyr Lys Gln Val Val Glu Glu Ile Leu Glu Arg Ile Gly Thr Gly
225                 230                 235                 240

Asn Leu Cys Asp Tyr Leu Pro Ala Leu Arg Trp Phe Asp Val Phe Gly
            245                 250                 255

Val Arg Asn Arg Ile Leu Ala Ala Val Ser Arg Arg Asp Ala Phe Leu
            260                 265                 270

Arg Arg Leu Ile Tyr Ala Ala Arg Trp Arg Met Asp Asp Gly Glu Lys
            275                 280                 285

Lys Ser Met Ile Ala Val Leu Leu Thr Leu Gln Lys Thr Gln Pro Glu
290                 295                 300

Val Tyr Thr Asp Asn Met Ile Thr Ala Leu Cys Ser Asn Leu Leu Gly
305                 310                 315                 320

Ala Gly Thr Glu Thr Thr Ser Thr Thr Ile Glu Trp Ala Met Ser Leu
                325                 330                 335

Leu Leu Asn His Pro Glu Thr Leu Lys Lys Ala Gln Ala Glu Ile Asp
            340                 345                 350

Ala Ser Val Gly Asn Ser Arg Leu Ile Thr Ala Asp Val Pro Arg
        355                 360                 365

Ile Thr Tyr Leu Gln Cys Ile Val Arg Glu Thr Leu Arg Leu Tyr Pro
    370                 375                 380

Ala Ala Pro Met Leu Ile Pro His Glu Ser Ser Ala Asp Cys Glu Val
385                 390                 395                 400

Gly Gly Tyr Ser Val Pro Arg Gly Thr Met Leu Leu Val Asn Ala Tyr
                405                 410                 415

Ala Ile His Arg Asp Pro Ala Ala Trp Glu Glu Pro Glu Arg Phe Val
            420                 425                 430

Pro Glu Arg Phe Glu Gly Gly Gly Cys Asp Gly Asn Leu Ser Met Pro
        435                 440                 445

Phe Gly Met Gly Arg Arg Cys Pro Gly Glu Thr Leu Ala Leu His
450                 455                 460

Thr Val Gly Leu Val Leu Gly Thr Leu Ile Gln Cys Phe Asp Trp Glu
465                 470                 475                 480

Arg Val Asp Gly Val Glu Val Asp Met Ala Glu Gly Gly Leu Thr
        485                 490                 495

Met Pro Lys Val Val Pro Leu Glu Ala Val Cys Arg Pro Arg Asp Ala
            500                 505                 510

Met Gly Gly Val Leu Arg Glu Leu
            515                 520

<210> SEQ ID NO 38
<211> LENGTH: 512
<212> TYPE: PRT
<213> ORGANISM: Oryza sativa
```

```
<400> SEQUENCE: 38

Met Asp Lys Ala Tyr Ile Ala Val Phe Ser Ile Val Ile Leu Phe Leu
1               5                   10                  15

Leu Val Asp Tyr Leu Arg Arg Leu Arg Gly Gly Gly Thr Ser Asn Gly
            20                  25                  30

Lys Asn Lys Gly Met Arg Leu Pro Pro Gly Leu Pro Ala Val Pro Ile
        35                  40                  45

Ile Gly His Leu His Leu Val Lys Lys Pro Met His Ala Thr Leu Ser
    50                  55                  60

Arg Leu Ala Ala Arg His Gly Pro Val Phe Ser Leu Arg Leu Gly Ser
65                  70                  75                  80

Arg Arg Ala Val Val Val Ser Ser Pro Gly Cys Ala Arg Glu Cys Phe
                85                  90                  95

Thr Glu His Asp Val Ala Phe Ala Asn Arg Pro Arg Phe Glu Ser Gln
            100                 105                 110

Leu Leu Met Ser Phe Asp Gly Thr Ala Leu Ala Met Ala Ser Tyr Gly
        115                 120                 125

Pro His Trp Arg Asn Leu Arg Arg Val Ala Ala Val Gln Leu Leu Ser
    130                 135                 140

Ala Arg Arg Val Gly Leu Met Ser Gly Leu Ile Ala Gly Glu Val Arg
145                 150                 155                 160

Ala Met Val Arg Ser Leu Cys Arg Arg Pro Ala Ala Ala Pro Val
                165                 170                 175

Gln Leu Lys Arg Arg Leu Phe Glu Leu Ser Leu Ser Val Leu Met Glu
            180                 185                 190

Thr Ile Ala Gln Ser Lys Ala Thr Arg Pro Glu Thr Thr Asp Thr Asp
        195                 200                 205

Thr Asp Met Ser Met Glu Ala Gln Glu Tyr Lys Gln Val Val Glu Glu
    210                 215                 220

Ile Leu Glu Arg Ile Gly Thr Gly Asn Leu Cys Asp Tyr Leu Pro Ala
225                 230                 235                 240

Leu Arg Trp Phe Asp Val Phe Gly Val Arg Asn Arg Ile Leu Ala Ala
                245                 250                 255

Val Ser Arg Arg Asp Ala Phe Leu Arg Arg Leu Ile Tyr Ala Ala Arg
            260                 265                 270

Trp Arg Met Asp Asp Gly Glu Lys Lys Ser Met Ile Ala Val Leu Leu
        275                 280                 285

Thr Leu Gln Lys Thr Gln Pro Glu Val Tyr Thr Asp Asn Met Ile Thr
    290                 295                 300

Ala Leu Cys Ser Asn Leu Leu Gly Ala Gly Thr Glu Thr Thr Ser Thr
305                 310                 315                 320

Thr Ile Glu Trp Ala Met Ser Leu Leu Leu Asn His Pro Glu Thr Leu
                325                 330                 335

Lys Lys Ala Gln Ala Glu Ile Asp Ala Ser Val Gly Asn Ser Arg Leu
            340                 345                 350

Ile Thr Ala Asp Asp Val Pro Arg Ile Thr Tyr Leu Gln Cys Ile Val
        355                 360                 365

Arg Glu Thr Leu Arg Leu Tyr Pro Ala Ala Pro Met Leu Ile Pro His
    370                 375                 380

Glu Ser Ser Ala Asp Cys Glu Val Gly Gly Tyr Ser Val Pro Arg Gly
385                 390                 395                 400

Thr Met Leu Leu Val Asn Ala Tyr Ala Ile His Arg Asp Pro Ala Ala
                405                 410                 415
```

```
Trp Glu Glu Pro Glu Arg Phe Val Pro Glu Arg Phe Glu Gly Gly
                420                 425                 430

Cys Asp Gly Asn Leu Ser Met Pro Phe Gly Met Gly Arg Arg Cys
            435                 440                 445

Pro Gly Glu Thr Leu Ala Leu His Thr Val Gly Leu Val Leu Gly Thr
450                     455                 460

Leu Ile Gln Cys Phe Asp Trp Glu Arg Val Asp Gly Val Glu Val Asp
465                 470                 475                 480

Met Ala Glu Gly Gly Leu Thr Met Pro Lys Val Val Pro Leu Glu
                485                 490                 495

Ala Val Cys Arg Pro Arg Asp Ala Met Gly Gly Val Leu Arg Glu Leu
            500                 505                 510

<210> SEQ ID NO 39
<211> LENGTH: 518
<212> TYPE: PRT
<213> ORGANISM: Sorghum bicolor

<400> SEQUENCE: 39

Met Asp Lys Ala Tyr Ile Ala Val Leu Ser Gly Ala Phe Leu Phe Leu
1               5                   10                  15

Leu His Tyr Leu Val Gly Arg Ala Gly Ser Gly Gly Lys Gly Lys Gly
                20                  25                  30

Lys Gly Ser Gln Gln Leu Pro Pro Ser Pro Pro Ala Ile Pro Phe Leu
            35                  40                  45

Gly His Leu Tyr Leu Val Lys Ala Pro Phe His Ala Ala Leu Ala Arg
        50                  55                  60

Leu Ala Ala Arg His Gly Pro Val Phe Ser Leu Arg Met Gly Ser Arg
65                  70                  75                  80

Arg Ala Val Val Val Ser Ser Pro Glu Cys Ala Lys Glu Cys Phe Thr
                85                  90                  95

Glu His Asp Leu Asn Phe Ala Asn Arg Pro Leu Phe Pro Ser Leu Arg
            100                 105                 110

Leu Val Ser Phe Asn Gly Ala Met Phe Ser Val Ala Ser Tyr Gly Pro
        115                 120                 125

Tyr Trp Arg Asn Leu Arg Arg Val Ala Ala Thr Gln Leu Leu Ser Ala
130                 135                 140

His Arg Val Ala Cys Met Thr Pro Thr Ile Ala Gly Glu Val Arg Ala
145                 150                 155                 160

Met Val Gln Arg Met Asp His Ala Ala Ala Ala Pro Gly Gly Ala
                165                 170                 175

Ala Arg Ile Gln Leu Lys Arg Arg Leu Phe Glu Leu Ser Leu Ser Val
            180                 185                 190

Leu Met Glu Thr Ile Ala Gln Thr Lys Thr Ser Arg Thr Glu Ala Asn
        195                 200                 205

Ala Asp Thr Asp Met Ser Pro Glu Ala His Glu Phe Lys Gln Ile Ile
    210                 215                 220

Asp Glu Leu Val Pro Tyr Leu Gly Thr Ala Asn Arg Trp Asp Tyr Leu
225                 230                 235                 240

Pro Val Leu Arg Trp Phe Asp Val Phe Gly Val Arg Asn Lys Ile Leu
                245                 250                 255

Asp Ala Val Ser Arg Arg Asp Ala Phe Leu Arg Arg Leu Ile Asp Gly
            260                 265                 270

Glu Arg Arg Arg Leu Asp Asp Gly Ser Glu Ser Glu Val Lys Ser Met
        275                 280                 285
```

```
Ile Ala Val Leu Leu Thr Met Gln Lys Ser Glu Pro Glu Val Tyr Thr
            290                 295                 300

Asp Thr Val Ile Ile Ala Leu Cys Ala Asn Leu Phe Leu Ala Gly Thr
305                 310                 315                 320

Glu Thr Thr Ser Thr Thr Thr Glu Trp Ala Met Ser Leu Leu Leu Asn
                325                 330                 335

His Pro Glu Val Leu Lys Lys Ala Gln Ala Glu Ile Asp Ala Ala Val
            340                 345                 350

Gly Thr Ser Arg Leu Val Thr Ala Asp Asp Val Ser Arg Leu Thr Tyr
            355                 360                 365

Leu Gln Cys Ile Ile Asn Glu Thr Leu Arg Leu His Pro Ala Ala Pro
    370                 375                 380

Leu Leu Leu Pro His Glu Ser Ser Ala Asp Cys Lys Val Gly Gly Tyr
385                 390                 395                 400

Asp Val Pro Arg Gly Thr Met Leu Leu Val Asn Val His Ala Val His
                405                 410                 415

Arg Asp Pro Val Val Trp Glu Glu Pro Ser Arg Phe Met Pro Glu Arg
            420                 425                 430

Phe Glu Asp Gly Lys Gln Ala Glu Gly Arg Leu Leu Met Pro Phe Gly
            435                 440                 445

Met Gly Arg Arg Lys Cys Pro Gly Glu Ala Leu Ala Leu Arg Thr Val
    450                 455                 460

Gly Leu Val Leu Gly Thr Leu Ile Gln Cys Phe Asp Trp Asp Arg Val
465                 470                 475                 480

Asp Gly Val Glu Val Asp Met Ala Glu Ser Gly Gly Leu Thr Met Pro
                485                 490                 495

Arg Ala Val Pro Leu Glu Ala Leu Cys Lys Pro Arg Ala Ala Met Arg
            500                 505                 510

Asp Val Leu Gln Lys Leu
            515

<210> SEQ ID NO 40
<211> LENGTH: 512
<212> TYPE: PRT
<213> ORGANISM: Sorghum bicolor

<400> SEQUENCE: 40

Met Asp Lys Ala Tyr Val Ala Ile Leu Ser Val Thr Phe Leu Phe Leu
1               5                   10                  15

Leu His Tyr Leu Met Gly His Ala Ala Val Gly Gly Lys Arg Lys Arg
            20                  25                  30

Leu Pro Pro Ser Pro Leu Ala Ile Pro Phe Ile Gly His Leu His Leu
        35                  40                  45

Val Lys Thr Pro Phe His Ser Ala Leu Val Arg Leu Ala Ala Arg His
    50                  55                  60

Gly Pro Val Phe Ser Met Arg Met Gly His Arg Arg Ala Val Val Val
65                  70                  75                  80

Ser Ser Pro Glu Cys Ala Lys Ala Cys Phe Thr Glu Tyr Asp Gln Ser
                85                  90                  95

Phe Ala Asn Arg Pro His Phe Gln Ser Met Arg Leu Val Ser Phe Asp
            100                 105                 110

Gly Ala Met Leu Ser Val Ser Ser Tyr Gly Pro Tyr Trp Arg Asn Leu
        115                 120                 125

Arg Arg Val Ala Ala Val Gln Leu Leu Ser Ala His Arg Val Ala Cys
    130                 135                 140
```

Met Ser Pro Val Ile Ala Ala Glu Val Arg Ala Met Val Arg Arg Met
145                 150                 155                 160

Asn Arg Leu Ala Ala Thr Ser Pro Gly Gly Ala Ala Arg Val Gln Leu
            165                 170                 175

Arg Arg Arg Leu Phe Glu Leu Ser Leu Ser Val Leu Met Glu Thr Ile
            180                 185                 190

Ala Gln Thr Lys Thr Ser Arg Ser Glu Ala Tyr Ala Asp Thr Asp Ile
            195                 200                 205

Ser Pro Glu Ala Asn Glu Leu Thr Gln Ile Ser Gln Glu Ile Met Pro
            210                 215                 220

Tyr Leu Gly Thr Ala Asn Leu Trp Asp Tyr Leu Pro Phe Leu Arg Trp
225                 230                 235                 240

Phe Asp Val Phe Gly Val Arg Asn Lys Leu Met Ala Ala Val Arg Trp
            245                 250                 255

Arg Asp Ala Phe Leu Arg Arg Leu Ile Asp Ala Glu Arg Arg Arg Leu
            260                 265                 270

Asp Asp Ala Gly Asp Ser Glu Lys Lys Ser Met Leu Ala Val Leu Leu
            275                 280                 285

Ser Leu Gln Lys Ser Glu Pro Glu Leu Tyr Thr Asp Thr Met Ile Met
290                 295                 300

Ala Leu Cys Gly Asp Met Phe Gly Ala Gly Thr Glu Thr Thr Ser Ser
305                 310                 315                 320

Thr Thr Glu Trp Ala Met Ser Leu Leu Leu Asn His Pro Glu Ala Leu
            325                 330                 335

Asn Lys Ala Arg Ala Glu Ile Asp Ala Val Val Gly Ser Ser Arg Leu
            340                 345                 350

Ile Thr Pro Asp Asp Val Pro Arg Leu Gly Tyr Leu His Cys Val Ile
            355                 360                 365

Asn Glu Thr Leu Arg Met Tyr Pro Ala Ala Pro Leu Leu Leu Pro His
            370                 375                 380

Glu Ser Ser Ala Asp Cys Asn Val Gly Gly Tyr Asp Val Pro Arg Gly
385                 390                 395                 400

Thr Leu Leu Ile Val Asn Ala Tyr Ala Ile His Arg Asp Pro Ala Val
            405                 410                 415

Trp Glu Asp Pro Ala Glu Phe Arg Pro Glu Arg Phe Glu Asp Gly Lys
            420                 425                 430

Ala Glu Gly Arg Leu Leu Met Pro Phe Gly Met Gly Arg Arg Lys Cys
            435                 440                 445

Pro Gly Glu Thr Leu Ala Leu Arg Thr Val Gly Leu Val Leu Gly Thr
            450                 455                 460

Leu Ile Gln Cys Phe Asp Trp Asp Arg Val Asp Gly Val Glu Ile Asp
465                 470                 475                 480

Met Thr Glu Ala Gly Gly Leu Thr Met Pro Arg Ala Val Pro Leu Glu
            485                 490                 495

Ala Thr Cys Lys Pro Arg Ala Ala Val Ser Asp Val Leu Lys Gln Leu
            500                 505                 510

<210> SEQ ID NO 41
<211> LENGTH: 522
<212> TYPE: PRT
<213> ORGANISM: Sorghum bicolor

```
<400> SEQUENCE: 41

Met Asp Lys Ala Tyr Val Ala Val Leu Ser Phe Ala Phe Leu Phe Val
1               5                   10                  15

Leu His Tyr Leu Val Gly Arg Ala Gly Gly Asn Gly Arg Lys Gly Asn
            20                  25                  30

Asn Gly Lys Gly Asn Ala Ala Gln Gln Arg Leu Pro Pro Ser Pro Pro
        35                  40                  45

Ala Val Pro Phe Leu Gly His Leu His Leu Val Lys Thr Pro Phe His
    50                  55                  60

Glu Ala Leu Ala Gly Leu Ala Ala Arg His Gly Pro Val Phe Ser Met
65                  70                  75                  80

Arg Met Gly Ser Arg Gly Ala Val Val Ser Ser Pro Glu Cys Ala
                85                  90                  95

Lys Glu Cys Phe Thr Glu His Asp Val Ala Phe Ala Asn Arg Pro Arg
            100                 105                 110

Phe Ala Thr Gln Glu Leu Val Ser Phe Gly Ala Ala Leu Ala Thr
            115                 120                 125

Ala Ser Tyr Gly Pro Tyr Trp Arg Asn Leu Arg Arg Val Ala Ala Val
    130                 135                 140

Gln Leu Leu Ser Ala His Arg Val Ala Cys Met Ser Ser Val Ile Ser
145                 150                 155                 160

Ala Glu Val Arg Ala Met Val Arg Arg Met Ser Arg Ala Ala Ala Ala
                165                 170                 175

Ala Pro Asp Gly Ala Ala Arg Val Gln Leu Lys Arg Arg Leu Phe Glu
            180                 185                 190

Val Ser Leu Ser Val Leu Met Glu Thr Ile Ala Gln Thr Lys Thr Ser
            195                 200                 205

Arg Thr Glu Ala Asp Ala Asp Thr Asp Met Ser Pro Glu Ala His Glu
210                 215                 220

Phe Lys Gln Ile Val Asp Glu Ile Val Pro His Leu Gly Thr Ala Asn
225                 230                 235                 240

Leu Trp Asp Tyr Leu Pro Val Leu Gln Trp Phe Asp Val Phe Gly Val
            245                 250                 255

Arg Asn Lys Ile Met Ala Ala Val Ser Arg Arg Asp Ala Phe Leu Arg
            260                 265                 270

Arg Leu Ile Asp Ala Glu Arg Arg Met Asp Asp Gly Gly Asp Ser
        275                 280                 285

Asp Lys Lys Ser Met Ile Ala Val Leu Leu Ser Leu Gln Lys Ser Glu
        290                 295                 300

Pro Glu Leu Tyr Thr Asp Thr Met Ile Met Ala Leu Cys Gly Asn Leu
305                 310                 315                 320

Phe Gly Ala Gly Thr Glu Thr Thr Ser Ser Thr Thr Glu Trp Ala Met
                325                 330                 335

Ser Leu Leu Leu Asn His Pro Glu Ala Leu Lys Lys Ala Gln Ala Glu
            340                 345                 350

Ile Asp Ala Val Val Gly Asn Ser Arg Leu Ile Thr Ala Glu Asp Val
            355                 360                 365

Pro Arg Leu Gly Tyr Leu Gln Cys Val Ile Asn Glu Thr Leu Arg Met
370                 375                 380

Tyr Pro Ala Ala Pro Leu Leu Pro His Glu Ser Ala Ala Asp Cys
385                 390                 395                 400

Lys Val Gly Gly Tyr Asp Val Pro Arg Gly Thr Leu Leu Ile Val Asn
            405                 410                 415
```

Ala Tyr Ala Ile His Arg Asp Pro Ala Val Trp Glu Asp Pro Ala Glu
            420                 425                 430

Phe Arg Pro Glu Arg Phe Glu Asp Gly Lys Ala Glu Gly Arg Leu Leu
        435                 440                 445

Met Pro Phe Gly Met Gly Arg Arg Lys Cys Pro Gly Glu Thr Leu Ala
    450                 455                 460

Leu Arg Thr Val Gly Leu Val Leu Gly Thr Leu Ile Gln Cys Ile Asp
465                 470                 475                 480

Trp Asp Arg Val Asp Gly Leu Glu Ile Asp Met Thr Ala Gly Gly Gly
                485                 490                 495

Leu Thr Met Pro Arg Ala Val Pro Leu Glu Ala Thr Cys Lys Pro Arg
            500                 505                 510

Ala Ala Met Arg Asp Val Leu Met Glu Leu
        515                 520

<210> SEQ ID NO 42
<211> LENGTH: 519
<212> TYPE: PRT
<213> ORGANISM: Sorghum bicolor

<400> SEQUENCE: 42

Met Glu Pro Ala Tyr Val Ala Ile Leu Ser Phe Val Phe Leu Phe Leu
1               5                   10                  15

Leu His Arg Leu Phe Gly Arg His Arg Arg Ile Asn Gly Lys Asn
            20                  25                  30

Asn Arg Ala Gln Leu Pro Pro Ser Pro Pro Ala Ile Pro Val Leu Gly
        35                  40                  45

His Leu His Leu Leu Gly Lys Lys Pro Ile His Ala Ala Leu Ala Arg
    50                  55                  60

Leu Ala Glu Arg Tyr Gly Pro Val Phe Ser Leu Arg Leu Gly Ser Arg
65                  70                  75                  80

Glu Ala Val Val Val Ser Ser Ala Ala Cys Ala Thr Glu Cys Phe Thr
                85                  90                  95

Glu Asn Asp Val Cys Phe Ala Asn Arg Pro Arg Phe Pro Thr Leu Leu
            100                 105                 110

Leu Val Ser Phe Gly Gly Ala Thr Leu Pro Met Cys Arg Tyr Gly Pro
        115                 120                 125

Tyr Trp Arg Ser Ile Arg Arg Val Ala Thr Val His Leu Leu Ser Ala
    130                 135                 140

His Arg Val Ser Cys Met Leu Pro Val Ile Ser Ala Glu Val Arg Ala
145                 150                 155                 160

Met Ala Arg Arg Met Tyr Arg Ser Ala Ala Gly Gly Ala Ala Arg
                165                 170                 175

Val Glu Leu Lys Arg Arg Leu Phe Glu Leu Ser Leu Ser Ala Leu Met
            180                 185                 190

Glu Thr Ile Ala Arg Thr Lys Met Ser Arg Ala Val Ala Asp Asp Asp
        195                 200                 205

Thr Asp Met Ser Pro Glu Ala Gln Glu Phe Met Lys Ala Leu Asp Val
    210                 215                 220

Leu Leu Arg Leu Leu Ser Ala Ala Asn Ser Trp Asp Tyr Leu Pro Val
225                 230                 235                 240

Leu Arg Trp Leu Asp Met Phe Gly Val Arg Asn Lys Ile Leu Ala Ala
                245                 250                 255

Val Ser Ala Arg Asp Ala Phe Leu Arg Arg Leu Ile Asp Ala Glu Arg
            260                 265                 270

Arg Arg Leu Glu Glu Gly Gly Glu Asn Asp Glu Lys Lys Ser
        275                 280                 285

Met Ile Gly Val Leu Leu Ser Leu Gln Lys Ser Glu Pro Glu Val Tyr
    290                 295                 300

Thr Asp Thr Thr Ile Met Ala Leu Cys Ser Ser Met Phe Ala Gly Gly
305                 310                 315                 320

Ser Glu Thr Thr Ala Thr Thr Ala Glu Trp Ala Met Ser Leu Leu Leu
                325                 330                 335

Ser His Pro Asp Val Leu Lys Lys Ala Gln Ala Glu Ile Asp Ala Ser
            340                 345                 350

Val Gly His Ser Arg Leu Leu Gly Ala Asp Asp Val Pro Arg Leu Gly
        355                 360                 365

Tyr Leu Gln Cys Ile Val Thr Glu Thr Leu Arg Leu Tyr Pro Val Val
    370                 375                 380

Pro Thr Leu Val Pro His Glu Ser Thr Ala Asp Cys Thr Val Gly Gly
385                 390                 395                 400

His His Val Pro Ser Gly Thr Met Leu Leu Val Asn Val Tyr Ala Ile
                405                 410                 415

His Arg Asp Pro Ala Thr Trp Ala Asp Pro Ala Ala Phe Arg Pro Glu
            420                 425                 430

Arg Phe Glu Asp Gly Gly Arg Ala Gln Gly Leu Phe Met Met Pro Phe
        435                 440                 445

Gly Met Gly Arg Arg Lys Cys Pro Gly Glu Ala Leu Ala Leu Arg Thr
    450                 455                 460

Leu Gly Leu Val Leu Gly Thr Leu Ile Gln Cys Phe Asp Trp Glu Thr
465                 470                 475                 480

Val Gly Gly Ala Glu Val Asp Met Ala Glu Gly Val Gly Ile Thr Leu
                485                 490                 495

Pro Arg Ala Val Pro Leu Glu Ala Ile Cys Lys Pro Arg His Ala Met
            500                 505                 510

Leu Glu Val Leu Lys Gly Leu
        515

<210> SEQ ID NO 43
<211> LENGTH: 513
<212> TYPE: PRT
<213> ORGANISM: Zea mays

<400> SEQUENCE: 43

Met Asp Lys Ala Tyr Val Ala Val Leu Ser Val Ala Phe Leu Phe Leu
1               5                   10                  15

Val His Tyr Leu Val Gly Arg Ala Ala Ala Gly Gly Lys Gly Arg
            20                  25                  30

Lys Arg Leu Pro Pro Ser Pro Leu Ala Ile Pro Phe Leu Gly His Leu
        35                  40                  45

His Leu Val Lys Thr Pro Phe His Ser Ala Leu Gly Arg Leu Ala Glu
    50                  55                  60

Arg His Gly Pro Val Phe Ser Leu Arg Met Gly Cys Arg Arg Ala Val
65                  70                  75                  80

Val Val Ser Ser Pro Glu Cys Ala Arg Ala Cys Phe Thr Glu His Asp
                85                  90                  95

Gln Ser Phe Ala Asn Arg Pro Arg Phe Glu Ser Met Arg Leu Val Ser
            100                 105                 110

Phe Asp Gly Ala Met Leu Ser Val Ser Ser Tyr Gly Pro Tyr Trp Arg
        115                 120                 125

```
Thr Leu Arg Arg Val Ala Ala Val Gln Leu Leu Ser Ala His Arg Val
    130                 135                 140

Ala Cys Met Ser Pro Val Ile Cys Ala Glu Val Arg Ala Met Val Arg
145                 150                 155                 160

Arg Met Ala Arg Leu Ala Ala Gly Gly Ala Ala Arg Val Gln Leu Arg
                165                 170                 175

Arg Arg Leu Phe Glu Leu Ser Leu Gly Val Leu Met Glu Thr Ile Ala
            180                 185                 190

Arg Thr Lys Thr Ser Arg Ser Glu Ala Cys Ala Ala Asp Thr Asp Val
        195                 200                 205

Ser Pro Glu Ala Ser Glu Leu Thr Arg Ile Ser Glu Glu Ile Met Pro
210                 215                 220

Tyr Leu Gly Thr Ala Asn Leu Trp Asp Tyr Leu Pro Phe Leu Arg Trp
225                 230                 235                 240

Phe Asp Val Phe Gly Val Arg Lys Lys Leu Met Ala Ala Val Arg Trp
                245                 250                 255

Arg Asp Ala Phe Leu Arg Arg Leu Ile Asp Ala Glu Arg Arg Arg Met
            260                 265                 270

Asp Gly Asp Gly Asp Gly Glu Lys Lys Ser Met Ile Ala Val Leu Leu
        275                 280                 285

Ser Leu Gln Lys Ser Glu Pro Glu Leu Tyr Thr Glu Thr Met Ile Met
290                 295                 300

Ala Leu Cys Gly Asp Leu Phe Gly Ala Gly Thr Glu Thr Thr Ser Val
305                 310                 315                 320

Thr Thr Glu Trp Ala Met Ser Leu Leu Leu Asn His Pro Glu Ala Leu
                325                 330                 335

Lys Lys Ala Gln Ala Glu Ile Asp Ala Val Val Gly Asn Ser Arg Arg
            340                 345                 350

Leu Ile Thr Ala Asp Asp Val Pro Arg Leu Gly Tyr Leu His Cys Val
        355                 360                 365

Ile Asn Glu Thr Leu Arg Met Tyr Pro Ala Ala Pro Leu Leu Leu Pro
370                 375                 380

His Glu Ser Ala Ala Asp Cys Lys Val Gly Gly Tyr Asp Val Pro Arg
385                 390                 395                 400

Gly Thr Leu Leu Ile Val Asn Ala Tyr Ala Ile His Arg Asp Pro Ala
                405                 410                 415

Val Trp Glu Asp Pro Gly Arg Phe Val Pro Glu Arg Phe Glu Asp Gly
            420                 425                 430

Lys Ala Glu Gly Arg Leu Leu Met Pro Phe Gly Met Gly Arg Arg Lys
        435                 440                 445

Cys Pro Gly Glu Thr Leu Ala Leu Arg Thr Val Gly Leu Val Leu Ala
450                 455                 460

Thr Leu Leu Gln Cys Phe Asp Trp Asp Thr Val Asp Gly Ala Gln Val
465                 470                 475                 480

Asp Met Thr Glu Ser Gly Gly Leu Thr Met Pro Arg Ala Val Pro Leu
                485                 490                 495

Glu Ala Met Cys Lys Pro Arg Ala Ala Met Cys Asp Val Leu Arg Glu
            500                 505                 510

Leu

<210> SEQ ID NO 44
<211> LENGTH: 517
<212> TYPE: PRT
<213> ORGANISM: Zea mays
```

```
<400> SEQUENCE: 44

Met Asp Lys Ala Tyr Ile Ala Ala Leu Ser Ala Ala Ala Leu Phe Leu
1               5                   10                  15

Leu His Tyr Leu Leu Gly Arg Arg Ala Gly Gly Glu Gly Lys Thr Lys
            20                  25                  30

Gly Ser Gln Arg Arg Leu Pro Pro Ser Pro Pro Ala Ile Pro Phe Leu
        35                  40                  45

Gly His Leu His Leu Val Lys Ala Pro Phe His Ala Ala Leu Ala Arg
    50                  55                  60

Leu Ala Ala Arg His Gly Pro Val Phe Ser Met Arg Leu Gly Thr Arg
65                  70                  75                  80

Arg Ala Val Val Val Ser Ser Pro Asp Cys Ala Arg Glu Cys Phe Thr
                85                  90                  95

Glu His Asp Val Asn Phe Ala Asn Arg Pro Leu Phe Pro Ser Met Arg
            100                 105                 110

Leu Ala Ser Phe Asp Gly Ala Met Leu Ser Val Ser Ser Tyr Gly Pro
        115                 120                 125

Tyr Trp Arg Asn Leu Arg Arg Val Ala Ala Val Gln Leu Leu Ser Ala
    130                 135                 140

His Arg Val Ala Cys Met Ala Pro Ala Ile Glu Ala Gln Val Arg Ala
145                 150                 155                 160

Met Val Arg Arg Met Asp Arg Ala Ala Ala Gly Gly Gly Gly Gly Ala
                165                 170                 175

Ala Arg Val Gln Leu Lys Arg Arg Leu Phe Glu Leu Ser Leu Ser Val
            180                 185                 190

Leu Met Glu Thr Ile Ala His Thr Lys Thr Ser Arg Ala Glu Ala Asp
        195                 200                 205

Ala Asp Ser Asp Met Ser Pro Glu Ala His Glu Phe Lys Gln Ile Val
    210                 215                 220

Asp Glu Leu Val Pro Tyr Ile Gly Thr Ala Asn Arg Trp Asp Tyr Leu
225                 230                 235                 240

Pro Val Leu Arg Trp Phe Asp Val Phe Gly Val Arg Asn Lys Ile Leu
                245                 250                 255

Asp Ala Val Gly Arg Arg Asp Ala Phe Leu Arg Arg Leu Ile Asp Gly
            260                 265                 270

Glu Arg Arg Arg Leu Asp Ala Gly Asp Ser Glu Ser Lys Ser Met
        275                 280                 285

Ile Ala Val Leu Leu Thr Leu Gln Lys Ser Glu Pro Glu Val Tyr Thr
    290                 295                 300

Asp Thr Val Ile Thr Ala Leu Cys Ala Asn Leu Phe Gly Ala Gly Thr
305                 310                 315                 320

Glu Thr Thr Ser Thr Thr Thr Glu Trp Ala Met Ser Leu Leu Leu Asn
                325                 330                 335

His Arg Glu Ala Leu Lys Lys Ala Gln Ala Glu Ile Asp Ala Ala Val
            340                 345                 350

Gly Thr Ser Arg Leu Val Thr Ala Asp Val Pro His Leu Thr Tyr
        355                 360                 365

Leu Gln Cys Ile Val Asp Glu Thr Leu Arg Leu His Pro Ala Ala Pro
    370                 375                 380

Leu Leu Leu Pro His Glu Ser Ala Ala Asp Cys Thr Val Gly Gly Tyr
385                 390                 395                 400

Asp Val Pro Arg Gly Thr Met Leu Leu Val Asn Val His Ala Val His
                405                 410                 415
```

```
Arg Asp Pro Ala Val Trp Asp Pro Asp Arg Phe Val Pro Glu Arg
            420                 425                 430

Phe Glu Gly Gly Lys Ala Glu Gly Arg Leu Leu Met Pro Phe Gly Met
        435                 440                 445

Gly Arg Arg Lys Cys Pro Gly Glu Thr Leu Ala Leu Arg Thr Val Gly
    450                 455                 460

Leu Val Leu Gly Thr Leu Leu Gln Cys Phe Asp Trp Asp Thr Val Asp
465                 470                 475                 480

Gly Ala Gln Val Asp Met Lys Ala Ser Gly Gly Leu Thr Met Pro Arg
                485                 490                 495

Ala Val Pro Leu Glu Ala Met Cys Arg Pro Arg Thr Ala Met Arg Asp
            500                 505                 510

Val Leu Lys Arg Leu
            515

<210> SEQ ID NO 45
<211> LENGTH: 523
<212> TYPE: PRT
<213> ORGANISM: Brachypodium distachyon

<400> SEQUENCE: 45

Met Asp Asn Ala Tyr Ile Ala Ala Leu Ser Leu Ala Phe Val Phe Leu
1               5                   10                  15

Leu His Tyr Leu Leu Lys Gly Lys Arg Ser Asn Gly Gly Asn Leu Pro
            20                  25                  30

Pro Ser Pro Pro Ala Ile Pro Ile Leu Gly His Leu His Leu Val Glu
        35                  40                  45

Lys Pro Leu His Ala Ala Leu Trp Arg Leu Ala Gly Arg Leu Gly Pro
    50                  55                  60

Val Phe Ser Leu Arg Leu Gly Ser Arg Pro Val Val Val Ser Ser
65                  70                  75                  80

Pro Glu Leu Ala Lys Glu Cys Phe Thr Glu His Asp Val Thr Phe Ala
                85                  90                  95

Asp Arg Pro Gln Phe Pro Ser Gln Leu Leu Val Ser Phe Gly Gly Thr
            100                 105                 110

Ala Leu Ala Thr Ala Ser Tyr Gly Pro His Trp Arg Asn Leu Arg Arg
        115                 120                 125

Val Ala Ala Val His Leu Leu Ser Ala His Arg Val Ala Ala Met Ser
    130                 135                 140

Ser Gly Val Ile Ser Ala Glu Val Arg Ala Met Ala Arg Arg Leu Phe
145                 150                 155                 160

Arg Ala Ser Ala Asp Gly Ser Gly Gly Ala Arg Val Gln Leu Lys Arg
                165                 170                 175

Arg Leu Phe Glu Leu Ser Leu Ser Val Leu Met Glu Ala Ile Ala Gln
            180                 185                 190

Thr Lys Ala Thr Arg Pro Asp Asp Ala Asp Gly Asp Thr Asp Met
        195                 200                 205

Ser Val Glu Ala Gln Glu Phe Lys Lys Val Val Asp Glu Ile Ile Pro
    210                 215                 220

His Leu Gly Thr Ala Asn Leu Trp Asp Tyr Leu Pro Val Leu Arg Trp
225                 230                 235                 240

Phe Asp Val Phe Gly Val Arg Asn Lys Ile Leu Ala Ala Val Arg Arg
                245                 250                 255

Arg Asp Ala Phe Leu Gly Arg Leu Ile Glu Ala Glu Arg Arg Arg Leu
            260                 265                 270
```

Glu Glu Glu Gly Gly Gly Gly Asp Gln Gln Gly Glu Lys Thr Ser
                275                 280                 285

Met Ile Ala Val Leu Leu Thr Leu Gln Lys Thr Glu Pro Glu Val Tyr
290                 295                 300

Thr Asp Thr Met Ile Thr Ala Leu Cys Ala Asn Leu Phe Gly Ala Gly
305                 310                 315                 320

Thr Glu Thr Thr Ser Thr Thr Thr Glu Trp Ala Met Ser Leu Leu Leu
                325                 330                 335

Asn His Pro Glu Val Leu Lys Lys Ala Gln Ala Glu Met Asp Ala Ser
                340                 345                 350

Val Gly Thr Ser Arg Leu Val Thr Ala Asp Asp Val Ala His Arg Leu
                355                 360                 365

Pro Tyr Leu Gln His Ile Val Ser Glu Thr Leu Arg Leu Tyr Pro Ala
                370                 375                 380

Ala Pro Met Leu Leu Pro His Gln Ser Ser Ala Asp Cys Lys Ile Gly
385                 390                 395                 400

Gly Tyr Thr Val Pro Arg Gly Thr Met Leu Leu Val Asn Ala Tyr Ala
                405                 410                 415

Ile His Arg Asp Pro Ala Ala Trp Gly Pro Ala Pro Glu Glu Phe Arg
                420                 425                 430

Pro Glu Arg Phe Glu Asp Ala Ser Asn Lys Gly Glu Glu Leu Pro Leu
                435                 440                 445

Met Leu Pro Phe Gly Met Gly Arg Arg Lys Cys Pro Gly Glu Thr Leu
450                 455                 460

Ala Leu Arg Thr Val Gly Met Val Leu Gly Thr Leu Val Gln Cys Phe
465                 470                 475                 480

Glu Trp Glu Arg Val Gly Gly Val Glu Val Asp Met Thr Gln Gly Thr
                485                 490                 495

Gly Leu Thr Met Pro Lys Ala Val Pro Leu Glu Ala Val Cys Arg Pro
                500                 505                 510

Arg Ala Ala Met Arg Asp Val Leu Gln Lys Leu
                515                 520

<210> SEQ ID NO 46
<211> LENGTH: 515
<212> TYPE: PRT
<213> ORGANISM: Brachypodium distachyon

<400> SEQUENCE: 46

Met Asp Lys Ala Tyr Ile Ala Val Leu Ser Leu Ala Phe Leu Phe Leu
1               5                   10                  15

Val His Tyr Leu Leu Gly Lys Ile Asn Gly Asn Lys Gln Lys Thr Ser
                20                  25                  30

Lys Leu Gln Leu Pro Ser Pro Pro Ala Ile Pro Phe Leu Gly His
                35                  40                  45

Leu His Leu Val Glu Thr Pro Phe His Leu Ala Leu Arg Arg Leu Ala
                50                  55                  60

Ala Arg His Gly Pro Val Phe Tyr Leu Arg Leu Gly Ser Arg Arg Ala
65                  70                  75                  80

Val Val Val Ser Ser Ala Ala Cys Ala Arg Glu Cys Phe Thr Glu His
                85                  90                  95

Asp Val Thr Phe Ala Asn Arg Pro Gln Phe Pro Ser Gln Gln Leu Val
                100                 105                 110

```
Ser Phe Asp Gly Ala Gly Leu Ala Gln Ser Ser Tyr Gly Pro His Trp
            115                 120                 125

Arg Asn Leu Arg Arg Val Ala Ala Val Gln Leu Leu Ser Ala His Arg
        130                 135                 140

Val Ala Cys Met Ser Gly Val Ile Ser Ala Glu Val Arg Ala Met Ala
145                 150                 155                 160

Arg Arg Leu Phe Arg Ala Ser Ala Ser Ala Pro Ala Arg Val Gln Leu
                165                 170                 175

Lys Arg Arg Leu Phe Glu Leu Ser Leu Ser Val Leu Met Glu Thr Ile
            180                 185                 190

Ala Arg Thr Lys Gly Thr Arg Pro Glu Ala Asp Ala Asp Val Asp Met
        195                 200                 205

Ser Val Glu Ala Gln Glu Phe Lys Lys Leu Val Asp Glu Ile Val Pro
210                 215                 220

His Leu Gly Thr Ala Asn Leu Trp Asp Tyr Leu Pro Leu Leu Arg Trp
225                 230                 235                 240

Phe Asp Val Met Gly Val Arg Asn Lys Ile Leu Lys Leu Val Arg Arg
                245                 250                 255

Arg Asp Val Phe Leu Gly Arg Leu Ile Asp Ala Glu Arg Arg Arg Leu
            260                 265                 270

Asp Glu Gly Gly Asp Gly Asp Asp Lys Lys Ser Met Ile Ser Val Met
        275                 280                 285

Leu Thr Leu Gln Lys Thr Glu Pro Glu Leu Tyr Thr Asp Thr Met Ile
    290                 295                 300

Lys Ser Leu Cys Ala Asn Leu Phe Gly Ala Gly Thr Glu Thr Thr Ser
305                 310                 315                 320

Thr Thr Thr Glu Trp Ala Met Ser Leu Leu Leu Asn His Pro Glu Val
                325                 330                 335

Leu Lys Lys Ala Gln Ala Glu Met Asp Ser Cys Val Gly Thr Ser Arg
            340                 345                 350

Leu Val Ser Phe Asp Asp Val Pro Arg Leu Ala Tyr Leu Gln Cys Val
        355                 360                 365

Leu Ser Glu Thr Leu Arg Leu Tyr Pro Ala Ala Pro Leu Leu Leu Pro
    370                 375                 380

His His Ser Ser Ala Asp Thr Lys Val Gly Gly Tyr Asp Val Pro Ala
385                 390                 395                 400

Asp Thr Met Leu Ile Val Asn Ala Tyr Ala Ile His Arg Glu Pro Ala
                405                 410                 415

Gly Ala Trp Gly Glu Arg Pro Glu Glu Phe Arg Pro Glu Arg Phe Glu
            420                 425                 430

Asp Gly Lys Ala Glu Gly Ala Phe Met Ile Pro Phe Gly Met Gly Arg
        435                 440                 445

Arg Arg Cys Pro Gly Glu Thr Leu Ala Leu Arg Thr Val Gly Met Val
    450                 455                 460

Leu Ala Thr Leu Val Gln Cys Phe Asp Trp Glu Arg Val Asp Gly Leu
465                 470                 475                 480

Glu Val Asp Met Ala Glu Gly Gly Leu Thr Met Pro Lys Val Val
                485                 490                 495

Pro Leu Glu Ala Val Cys Thr Pro Arg Gly Thr Met Leu Arg Val Leu
            500                 505                 510

Arg Glu Leu
    515
```